(12) United States Patent
Failli et al.

(10) Patent No.: US 7,691,848 B2
(45) Date of Patent: Apr. 6, 2010

(54) PYRROLOBENZODIAZEPINE ARYLCARBOXAMIDES AND DERIVATIVES THEREOF AS FOLLICLE-STIMULATING HORMONE RECEPTOR ANTAGONISTS

(75) Inventors: Amedeo A. Failli, Princeton Junction, NJ (US); Dominick Quagliato, Bridgewater, NJ (US); Patrick Andrae, Jamesburg, NJ (US); Gavin D. Heffernan, Florence, NJ (US); Richard D. Coghlan, Phoenixville, PA (US); Emily S. Shen, Westtown, PA (US)

(73) Assignee: Wyeth, Madison, NJ (US)

( * ) Notice: Subject to any disclaimer, the term of this patent is extended or adjusted under 35 U.S.C. 154(b) by 927 days.

(21) Appl. No.: 11/365,035

(22) Filed: Mar. 1, 2006

(65) Prior Publication Data

US 2006/0199806 A1    Sep. 7, 2006

Related U.S. Application Data

(60) Provisional application No. 60/657,931, filed on Mar. 2, 2005.

(51) Int. Cl.
A61P 15/18 (2006.01)
A61K 31/55 (2006.01)
C07D 487/12 (2006.01)

(52) U.S. Cl. ...................... 514/220; 540/561
(58) Field of Classification Search .............. 514/220; 540/561
See application file for complete search history.

(56) References Cited

U.S. PATENT DOCUMENTS

| | | |
|---|---|---|
| 6,200,963 B1 | 3/2001 | Wrobel et al. |
| 6,355,633 B1 | 3/2002 | Wrobel et al. |
| 6,426,357 B1 | 7/2002 | Scheuerman et al. |

FOREIGN PATENT DOCUMENTS

| | | |
|---|---|---|
| WO | WO 00/08015 | 2/2000 |
| WO | WO 00/58277 A | 10/2000 |
| WO | WO 01/47875 | 7/2001 |
| WO | WO 02/09705 | 2/2002 |
| WO | WO 02/09706 | 2/2002 |
| WO | WO 02/070493 | 9/2002 |
| WO | WO 02/083678 | 10/2002 |
| WO | WO 02/083680 | 10/2002 |
| WO | WO 02/083683 | 10/2002 |
| WO | WO 02/083684 | 10/2002 |
| WO | WO 02/085907 | 10/2002 |
| WO | WO 03/004028 | 1/2003 |
| WO | WO 04/056779 A | 7/2004 |
| WO | WO 2004/056780 A2 | 7/2004 |

OTHER PUBLICATIONS

Guo, Small Molecule Agonists and Antagonists for the LH and FSH Receptors, Expert Opinion in Therapeutic Patents, vol. 15, No. 11, pp. 1555-1564, Nov. 2005.*
Schoenberg, et al., "Palladium-catalyzed amidation of aryl, heterocyclic, and vinylic halides," *J. Org. Chem.* (1974) 39(23):3327-3331.
Aittomaki et al., "Mutation in the follicle-stimulating hormone receptor gene causes hereditary hypergonadotropic ovarian failure," *Cell* (1995) 82(6):959-968.
Arey et al., "Identification and Characterization of a Selective, Nonpeptide Follicle-Stimulating Hormone Receptor Antagonist," *Endocrinology* (2002) 143:3822-3829.
Badone et al., "Highly Efficient Palladium-Catalyzed Boronic Acid Coupling Reactions in Water: Scope and Limitations," *J Org Chem* (1997) 62(21):7170-7173.
Coffen et al., "2-Benzazepines. 8. Zerovalent nickel mediated biaryl synthesis of an anxiolytic pyrimido[5,4-d][2]benzazepine," *J Org Chem* (1984) 49(2):296-300.
Danesi et al., "Clinical and experimental evidence of inhibition of testosterone production by suramin," *J Clin Endocrinol Metab* (1996) 81(6):2238-2246.
Daugherty et al., "Suramin inhibits gonadotropin action in rat testis: implications for treatment of advanced prostate cancer," *J Urol* (1992) 147(3):727-732.
Farina et al., "On the Nature of the "Copper Effect" in the Stine Cross-Coupling," *J Org Chem* (1994) 59(20):5905.
George et al., "Evaluation of a CRE-Directed Luciferase Reporter Gene Assay as an Alternative to Measuring cAMP Accumulation," *J Biomol Screening* (1997) 2:235-240.
Giroux et al., "One pot biaryl synthesis via in situ boronate formation," *Tetrahedron Lett* (1997) 38(22):3841-3844.
Guo et al., "Small molecule biaryl FSH receptor agonists. Part 1: Lead discovery via encoded combinatorial synthesis," *Bioorg Med Chem Lett* (2004) 14(7):1713-1720.
Hsueh et al., "Granulosa cells as hormone targets: the role of biologically active follicle-stimulating hormone in reproduction," *Rec Prog Horm Res* (1989) 45:209-227.

(Continued)

Primary Examiner—Brenda L Coleman
(74) Attorney, Agent, or Firm—Pepper Hamilton LLP

(57) ABSTRACT

This invention provides pyrrolobenzodiazepine arylcarboxamides selected from those of Formula (1), which act as follicle stimulating hormone receptor antagonists, as well as pharmaceutical compositions and methods of treatment utilizing these compounds.

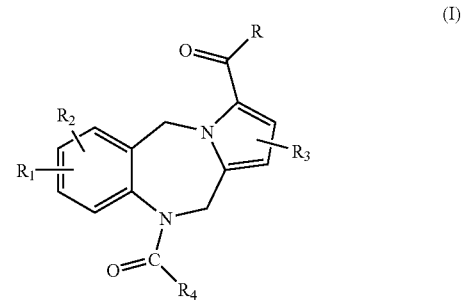

(I)

44 Claims, No Drawings

OTHER PUBLICATIONS

Inanaga et al., "A Rapid Esterification by Means of Mixed Anhydride and Its Application to Largering Lactonization," *Bull Chem Soc Jpn* (1979) 52(7):1989-1993.

Ishiyama et al., "Synthesis of arylboronates via the palladium(0)-catalyzed cross-coupling reaction of tetra(alkoxo)diborons with aryl triflates," *Tetrahedron Lett* (1997) 38(19):3447-3450.

Ishiyama et al., "Palladium(0)-Catalyzed Cross-Coupling Reaction of Alkoxydiboron with Haloarenes: A Direct Procedure for Arylboronic Esters," *J Org Chem* (1995) 60(23):7508-7510.

Kelton et al., "The cloning of the human follicle stimulating hormone receptor and its expression in COS-7, CHO, and Y-1 cells," *Mol Cell Endocrinoly* (1992) 89(1-2):141-151.

Lindstedt et al., "Follitropin (FSH) deficiency in an infertile male due to FSHbeta gene mutation. A syndrome of normal puberty and virilization but underdeveloped testicles with azoospermia, low FSH but high lutropin and normal serum testosterone concentrations," *Clin Chem Lab Med* (1998) 36(8):663-665.

Mukherjee et al., "Gonadotropins induce rapid phosphorylation of the 3',5'-cyclic adenosine monophosphate response element binding protein in ovarian granulosa cells," *Endocrinology* (1996) 137(8):3234-3245.

Quattropani et al., "Discovery and development of a new class of potent, selective, orally active oxytocin receptor antagonists," *J Med Chem* (2005) 48(24):7882-7905.

Serradeil-Le Gal et al., "SSR126768A (4-chloro-3-[(3R)-(+)-5-chloro-1-(2,4-dimethoxybenzyl)-3-methyl-2-oxo-2,3-dihydro-1H-indol-3-yl]-N-ethyl-N-(3-pyridylmethyl)-benzamide, hydrochloride): a new selective and orally active oxytocin receptor antagonist for the prevention of preterm labor," *J Pharmacol Exper Ther* (2004) 309(1):414-424.

Shen "Palladium catalyzed coupling of aryl chlorides with arylboronic acids," *Tetrahedron Letters* (1997) 38(32):5575.

Street et al., "Synthesis and serotonergic activity of 5-(oxadiazolyl)tryptamines: potent agonists for 5-HT1D receptors," *J Med Chem* (1993) 36(11):1529.

Suzuki "New synthetic transformations via organoboron compounds," *Pure & Appl Chem* (1994) 66(2):213-222.

Tilly et al., "Expression of recombinant human follicle-stimulating hormone receptor: species-specific ligand binding, signal transduction, and identification of multiple ovarian messenger ribonucleic acid transcripts," *Endocrinology* (1992) 131(2):799-806.

Wolfe et al., "Highly Active Palladium Catalysts for Suzuki Coupling Reactions," *J Am Chem Soc* (1999) 121(41):9550-9561.

Wrobel et al., "Synthesis of (bis)sulfonic acid, (bis)benzamides as follicle-stimulating hormone (FSH) antagonists," *Bioorg Med Chem* (2002) 10(3):639-656.

Wyatt et al., "Structure-activity relationship investigations of a potent and selective benzodiazepine oxytocin antagonist," *Bioorg Med Chem Letters* (2001) 11(10):1301-1305.

Wyatt et al., "Identification of potent and selective oxytocin antagonists. Part 1: indole and benzofuran derivatives," *Bioorg Med Chem Letters* (2002) 12(10):1399-1404.

Wyatt et al., "Identification of potent and selective oxytocin antagonists. Part 2: further investigation of benzofuran derivatives," *Bioorg Med Chem Letters* (2002) 12(10):1405-1411.

March, *Advanced Organic Chemistry*, $3^{rd}$ ed., pp. 647-648, John Wiley & Sons, New York (1985).

March, *Advanced Organic Chemistry*, $3^{rd}$ ed., p. 788, John Wiley & Sons, New York (1985).

\* cited by examiner

PYRROLOBENZODIAZEPINE ARYLCARBOXAMIDES AND DERIVATIVES THEREOF AS FOLLICLE-STIMULATING HORMONE RECEPTOR ANTAGONISTS

This Application claims benefit of priority under 35 U.S.C. 119(e) to U.S. Provisional Patent Application No. 60/657,931, filed Mar. 2, 2005.

BACKGROUND OF INVENTION

This invention concerns novel pyrrolobenzodiazepine arylcarboxamides, which act as follicle-stimulating hormone receptor antagonists, as well as pharmaceutical compositions and methods of treatment utilizing these compounds.

Reproduction in women depends upon the dynamic interaction of several compartments of the female reproductive system. The hypothalamic-pituitary-gonadal axis orchestrates a series of events affecting the ovaries and the uterine-endometrial compartment that leads to the production of mature ova, ovulation, and ultimately appropriate conditions necessary for fertilization. Specifically, luteinizing hormone-releasing hormone (LHRH), released from the hypothalamus, initiates the release of the gonadotropins, luteneizing hormone (LH) and follicle-stimulating hormone (FSH) from the pituitary. These hormones act directly on the ovary to promote the development of selected follicles by inducing granulosa and theca cell proliferation and differentiation. FSH stimulates aromatization of androgens to estrogens and increases the expression of LH receptors in the theca cells. The follicles, in turn, secrete steroids (estradiol, progesterone) and peptides (inhibin, activin). Estradiol and inhibin levels progressively increase during the follicular phase of the menstrual cycle until ovulation. Inhibin decreases FSH secretion from the pituitary gland, while estradiol acts on the hypothalamus and pituitary to induce the LH surge in midcycle, which results in ovulation. Afterwards, the post-ovulation ruptured follicle forms the corpus luteum, which produces progesterone. Ovarian hormones, in turn, regulate the secretion of gonadotropins through a classical long-loop negative feedback mechanism. The elucidation of these control mechanisms has provided opportunities for the development of effective strategies to control fertility, including both enhancement of fertility and contraception. For recent reviews of FSH action see: "FSH Action and Intraovarian Regulation", B. C. J. M. Fauser, Ed., Parthenon Publishing Group, Vol. 6, 1997 and A. J. Hsueh et. al., *Rec. Prog. Horm. Res.*, 45, 209-227, 1989.

Current hormonal contraception methods are steroidal in nature (progestins and estrogens) and modulate long-loop feedback inhibition of gonadotropin secretion, as well as affecting peripheral mechanisms such as sperm migration and fertilization. The development of specific antagonists of the receptor for FSH (FSH-R) would provide an alternative strategy for hormonal contraception. Such antagonists would block FSH-mediated follicular development leading to a blockade of ovulation, thereby producing the desired contraceptive effect. Support for the effectiveness of this strategy is provided by the mechanism that causes resistant ovary syndrome, which results in infertility in women. The infertility experienced by these women is the result of non-functional FSH receptors (K. Aittomaki et al., *Cell*, 82, 959-968, 1995). This approach to contraception may be applicable to men as well, since idiopathic male infertility seems to be related to a reduction in FSH binding sites. In addition, men with selective FSH deficiency are oligo- or azoospermic with normal testosterone levels and present normal virilization (G. Lindstedt et al., *Clin. Lab. Med.*, 36, 664, 1998). Therefore, low molecular weight FSH antagonists may provide a versatile novel method of contraception. Such an antagonist could be expected to interfere with follicle development and thus ovulation, while maintaining sufficient estrogen production and beneficial effects on bone mass.

FSH actions are mediated by binding of the hormone to a specific transmembrane G protein-coupled receptor exclusively expressed in the ovary, leading to activation of the adenyl cyclase system and elevation of intracellular levels of the second messenger cAMP (A. Mukherjee et al., *Endocrinology*, 137, 3234 1996).

Recently suramin, a sulfonic acid anticancer agent with a wide variety of activities, was shown to inhibit FHS binding to its receptor (R. L. Daugherty et al., *J. Urol.*, 147, 727 (1992). Administration of suramin causes a decrease in testosterone production in rats and humans (R. Danesi et al., *J. Clin. Endocrinol. Metab.* 81, 2238-2246, 1996). Recently, other more selective sulfonic acid-based FSH receptor antagonists were reported by B. J. Arey et al. (*The Endocrine Society*, 82$^{nd}$ Annual Meeting, Toronto, Canada Jun. 21-24, 2000, and *Endocrinology* 143 (10), 3822, 2002). An additional class of stilbene (bis)sulfonic acid competitive inhibitors of FSH at its receptor has also been reported by J. Wrobel et al. (*Bioorg. Med. Chem.* 10, 639-656, 2002).

Thiazolidinone FSH-R agonists and antagonists have been disclosed by R. Scheuerman et al. in WO 02/09705 and WO 02/09706 (2002) and in U.S. Pat. No. 6,426,357 (2002), respectively. Cyclic and acyclic alpha- and beta-aminocarboxamides as FSH-R agonists are disclosed by El Tayer et al. in WO 00/08015 (2000). Substituted aminoalkylamide derivative FSH-R antagonists have been disclosed by Coats et al. in WO 01/47875 (2001); aryl sulfonic acids and derivatives FSH-R antagonists have been disclosed by Wrobel et al. in U.S. Pat. No. 6,200,963 (2001) and U.S. Pat. No. 6,355,633 (2002). Tetrahydroquinoline derivatives have been disclosed as FSH-R modulators to control fertility by Van Straten et al. in WO 03/004028 (2003). Bisaryl derivatives with FSH-R modulatory activity have been disclosed by T. Guo et al. in WO 02/070493A1. Encoded combinatorial and parallel synthesis approaches to bisaryl FSH-R agonists have also been reported by T. Guo et al. in *Bioorg. Med. Chem. Lett.* 14, 1713-1716, 2004 and 1717-1720, 2004, respectively. Failli et al. in WO 02/083683 (2002) have disclosed a subset of pyrrolobenzodiazepines as tocolytic oxytocin receptor binding antagonists.

It can be seen that there is a great need for FSH receptor binding antagonists that can be used for contraception. This invention is directed to these, as well as other, important ends.

SUMMARY OF THE INVENTION

The present invention relates to pyrrolobenzodiazepines arylcarboxamides and derivatives having antagonist activity on the FSH receptor, and to their use as contraceptives.

In accordance with this invention are novel compounds represented by the structure of Formula (I):

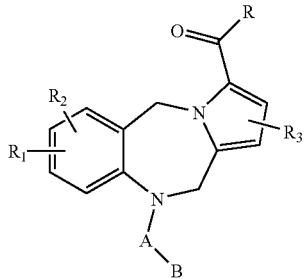

(I)

wherein
$R_1$ and $R_2$ are selected independently from the group consisting of hydrogen, ($C_1$-$C_6$) alkyl, halogen, trifluoromethyl, hydroxyl, ($C_1$-$C_6$) alkoxy, —$OCF_3$, carboxy, —CONH[($C_1$-$C_6$)alkyl], —CON[($C_1$-$C_6$) alkyl]$_2$, amino, ($C_1$-$C_6$) alkylamino and —NHCO[($C_1$-$C_6$) alkyl];

$R_3$ is selected from the group consisting of hydrogen, ($C_1$-$C_6$) alkyl, ($C_1$-$C_6$) alkoxy, hydroxyl, amino, ($C_1$-$C_6$) alkylamino, —C(O)—($C_1$-$C_6$)alkyl and halogen;

A is —C=O;

B is selected independently from the group consisting of (a)

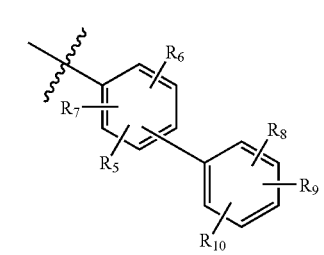

(b)

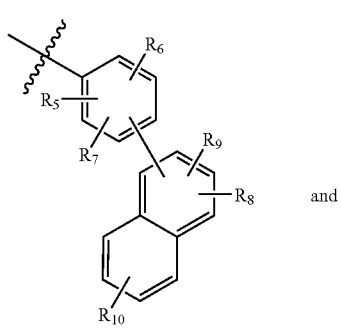

(c)

wherein $R_5$, $R_6$, $R_7$, $R_8$, $R_9$ and $R_{10}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{13}$, —$SO_2N(R_{13})_2$, —$(CH_2)_pCN$,
—$(CH_2)_pCOOR_{14}$, —$(CH_2)_pNR_{51}R_{52}$, —$(CH_2)_pCONR_{51}R_{52}$, —CH=NOH, —CH=NO—($C_1$-$C_6$) alkyl,

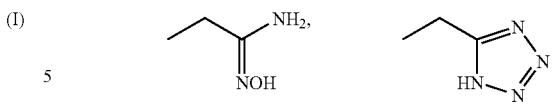

and —C(O) aryl wherein the aryl is optionally substituted by alkyl;

$R_{11}$ and $R_{12}$ are selected independently from the group consisting of hydrogen, alkyl and halogen;

W is O or S;

$R_{13}$ and $R_{14}$ are each independently hydrogen or alkyl;

$R_{51}$ and $R_{52}$ are each independently hydrogen or alkyl;

or $R_{51}$ and $R_{52}$ can be taken together with the nitrogen to which they are attached to form a 4-6 membered saturated ring optionally containing one or more O, S or N atoms;

p is 0 or 1;

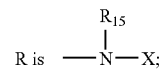

$R_{15}$ is hydrogen or alkyl;

X is —F-G or

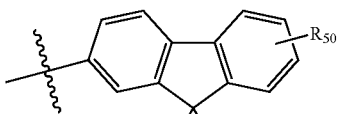

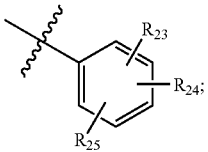

F is selected from the group consisting of

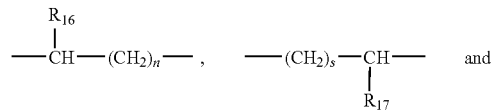

aryl optionally substituted by alkyl;

n is an integer from 0 to 3;

s is an integer from 1 to 3;

$R_{16}$ is selected from the group consisting of hydrogen, alkyl, and hydroxyalkyl;

$R_{17}$ is selected from the group consisting of hydroxy, dialkylamino and aryl;

G is

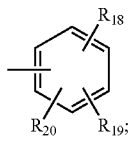

or F and G taken together can form a cycloalkyl group having an aryl group fused thereto;

and $R_{18}$, $R_{19}$ and $R_{20}$ are selected independently from the group consisting of hydrogen, alkyl, alkoxy, halogen, trifluoromethyl, hydroxy, trifluoromethoxy, aryloxy, —(CO) aryl, carboxy, carbalkoxy, amino, aminoalkyl, alkylamino, dialkylamino and aryl optionally substituted by alkyl; or when $R_{18}$ is hydrogen and $R_{19}$ and $R_{20}$ are on adjacent carbon atoms, then $R_{19}$ and $R_{20}$ can together form —O(—CH$_2$)$_n$—O— wherein n is 1 or 2;

$R_{21}$ and $R_{22}$ are each independently hydrogen or hydroxyl; or $R_{21}$ and $R_{22}$ taken together with the carbon to which they are attached can form a carbonyl group;

$R_{23}$, $R_{24}$ and $R_{25}$ are selected independently from the group consisting of hydrogen, alkyl, alkoxy, carbalkoxy and dialkylamino; and $R_{50}$ is H or halogen; or a salt thereof.

The compounds of the present invention are useful for inhibiting the fertility of a mammal. The compounds are useful also for preventing conception and for blocking follicular development that is mediated by follicle-stimulating hormone in a mammal.

DETAILED DESCRIPTION OF THE INVENTION

The present invention discloses novel, non-peptidic, low molecular weight FSH receptor binding antagonists of unique structure. None of the aforementioned compounds is disclosed to be follicle-stimulating hormone receptor (FSH-R) antagonists or contraceptive agents. The compounds of the present invention differ from these previously described compounds in that they do not contain a pyridine carboxamide moiety, are active as FSH-R antagonists and useful as contraceptive agents.

The present invention comprises the compounds of Formula (I):

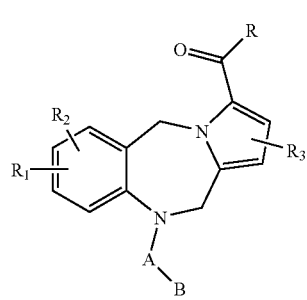

wherein $R_1$ and $R_2$ are selected independently from the group consisting of hydrogen, (C$_1$-C$_6$) alkyl, halogen, trifluoromethyl, hydroxyl, (C$_1$-C$_6$) alkoxy, —OCF$_3$, carboxy, —CONH[(C$_1$-C$_6$)alkyl], —CON[(C$_1$-C$_6$) alkyl]$_2$, amino, (C$_1$-C$_6$) alkylamino and —NHCO[(C$_1$-C$_6$) alkyl];

$R_3$ is selected from the group consisting of hydrogen, (C$_1$-C$_6$) alkyl, (C$_1$-C$_6$) alkoxy, hydroxyl, amino, (C$_1$-C$_6$) alkylamino, —C(O)—(C$_1$-C$_6$)-alkyl and halogen;

A is —C=O;

B is selected independently from the group consisting of

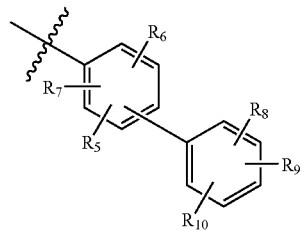

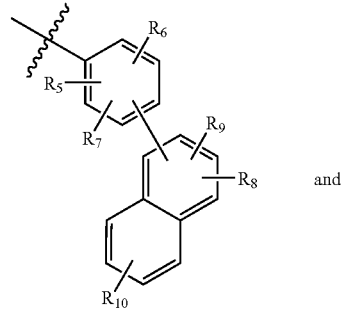

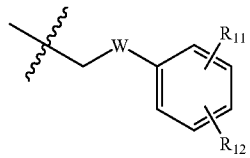

wherein $R_5$, $R_6$, $R_7$, $R_8$, $R_9$ and $R_{10}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —SO$_2$alkyl, —SO$_2$NHR$_{13}$, —SO$_2$N(R$_{13}$)$_2$, —(CH$_2$)$_p$CN,
—(CH$_2$)$_p$COOR$_{14}$, —(CH$_2$)$_p$NR$_{51}$R$_{52}$, —(CH$_2$)$_p$CONR$_{51}$R$_{52}$, —CH=NOH, —CH=NO—(C$_1$-C$_6$) alkyl, and —C(O)aryl wherein the aryl is optionally substituted by alkyl;

$R_{11}$ and $R_{12}$ are selected independently from the group consisting of hydrogen, alkyl and halogen;

W is O or S;

$R_{13}$ and $R_{14}$ are each independently hydrogen or alkyl;

$R_{51}$ and $R_{52}$ are each independently hydrogen or alkyl;

or $R_{51}$ and $R_{52}$ can be taken together with the nitrogen to which they are attached to form a 4-6 membered saturated ring optionally containing one or more O, S or N atoms;

p is 0 or 1;

R is —N(R$_{15}$)—X;

$R_{15}$ is hydrogen or alkyl;

X is —F-G or

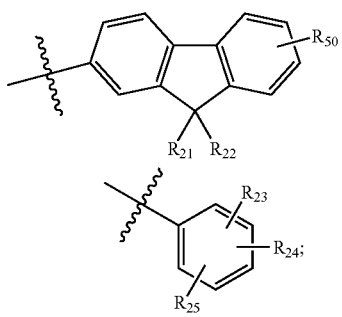

F is selected from the group consisting of

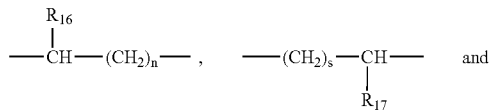

aryl optionally substituted by alkyl;
n is an integer from 0 to 3;
s is an integer from 1 to 3;
$R_{16}$ is selected from the group consisting of hydrogen, alkyl, and hydroxyalkyl;
$R_{17}$ is selected from the group consisting of hydroxy, dialkylamino and aryl;
G is

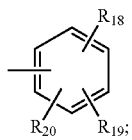

or F and G taken together can form a cycloalkyl group having an aryl group fused thereto; and
$R_{18}$, $R_{19}$ and $R_{20}$ are selected independently from the group consisting of hydrogen, alkyl, alkoxy, halogen, trifluoromethyl, hydroxy, trifluoromethoxy, aryloxy, —(CO)aryl, carboxy, carbalkoxy, amino, aminoalkyl, alkylamino, dialkylamino and aryl optionally substituted by alkyl; or when $R_{18}$ is hydrogen and $R_{19}$ and $R_{20}$ are on adjacent carbon atoms, then $R_{19}$ and $R_{20}$ can together form —O(—CH$_2$)$_m$—O— wherein m is 1 or 2;
$R_{21}$ and $R_{22}$ are each independently hydrogen or hydroxyl; or $R_{21}$ and $R_{22}$ taken together with the carbon to which they are attached can form a carbonyl group;
$R_{23}$, $R_{24}$ and $R_{25}$ are selected independently from the group consisting of hydrogen, alkyl, alkoxy, carbalkoxy and dialkylamino; and
$R_{50}$ is H or halogen; or a salt thereof.

In some embodiments of the invention, $R_1$, $R_2$, $R_3$ and $R_{15}$ are each hydrogen.

In some embodiments, the compounds of the invention have the structure X, wherein X is F-G. In some such embodiments, F is selected from the group consisting of —CH$_2$—, —(CH$_2$)$_2$—, —(CH$_2$)$_3$—, —(CH$_2$)$_4$—, —CH$_2$CH(phenyl)-, —CH(CH$_3$)—, —(CH$_2$)$_2$CH(phenyl)-, —CH(CH$_3$)(CH$_2$)$_2$—, —CH$_2$CH(OH)—, —CH(CH$_2$OH)—, —CH$_2$CH(N(CH$_3$)$_2$)— and phenyl optionally substituted with methyl. In some such embodiments, each of said $R_{18}$, $R_{19}$ and $R_{20}$ of said G is selected independently from the group consisting of hydrogen, —CH$_3$, —CF$_3$, —OCH$_3$, —OCF$_3$, halogen, —CO-phenyl, OH, —N(CH$_3$)$_2$, —COOCH$_3$, phenoxy, —NH$_2$ and —CH$_2$NH$_2$; or when $R_{18}$ is hydrogen and $R_{19}$ and $R_{20}$ are on adjacent carbon atoms then $R_{19}$ and $R_{20}$ can together form a structure of the formula —O(—CH$_2$)$_m$—O— wherein m is 1 or 2, e.g.,

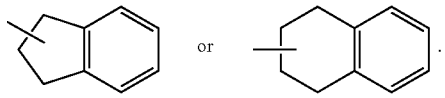

In further such embodiments, F is selected from the group consisting of —CH$_2$—, —(CH$_2$)$_2$—, —(CH$_2$)$_3$—, —(CH$_2$)$_4$—, —CH$_2$CH(phenyl)-, —CH(CH$_3$)—, —(CH$_2$)$_2$CH(phenyl)-, —CH(CH$_3$)(CH$_2$)$_2$—, —CH$_2$CH(OH)—, —CH(CH$_2$OH)—, —CH$_2$CH(N(CH$_3$)$_2$)— and phenyl optionally substituted with methyl; and each of said $R_{18}$, $R_{19}$ and $R_{20}$ of said G is selected independently from the group consisting of hydrogen —CH$_3$, —CF$_3$, —OCH$_3$, —OCF$_3$, halogen, —CO-phenyl, OH, —N(CH$_3$)$_2$, —COOCH$_3$, phenoxy, —NH$_2$ and —CH$_2$NH$_2$; or when $R_{18}$ is hydrogen and $R_{19}$ and $R_{20}$ are on adjacent carbon atoms then $R_{19}$ and $R_{20}$ can together form a structure of the formula —O(—CH$_2$)$_n$—O—, wherein n is 1 or 2. In some embodiments of the invention, F and G are taken together to form a cycloalkyl group having an aryl group fused thereto such as

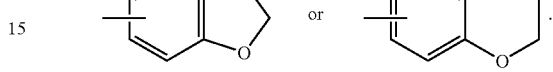

In further embodiments of the compounds of the invention, X is:

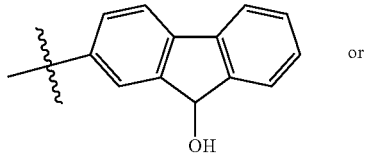

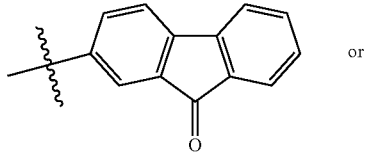

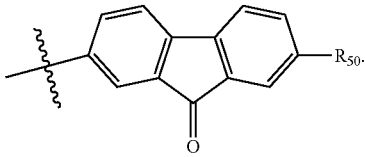

In still further embodiments, X is

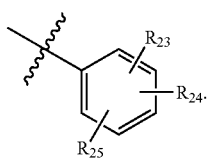

In some such embodiments, the $R_{23}$, $R_{24}$ and $R_{25}$ substituents of X are each independently selected from the group consisting of —$OCH_3$, —$COOCH_3$, —$COOCH_2CH_3$, —$C(CH_3)_3$, $NH_2$ and phenyl optionally substituted with —$CH_3$.

In some embodiments of the compounds of the invention, B has the structure (a). In some such embodiments, the $R_5$, $R_6$, $R_7$, $R_8$, $R_9$ and $R_{10}$ substituents of structure (a) are each independently selected from H, alkyl, halogen and alkoxy. In further such embodiments, $R_5$, $R_6$, $R_7$, $R_8$, $R_9$ and $R_{10}$ of structure (a) are each independently selected from H, methyl, methoxy and fluorine.

In some embodiments of the compounds of the invention, B is 2,2'-dimethyl-1,1'-biphenyl-4-yl or 2-methoxy-2'-methyl-1,1'-biphenyl-4-yl and X is F-G wherein F is —$CH_2$— or —$(CH_2)_2$—, and G is

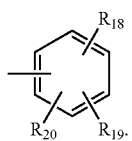

In some such embodiments, each of the $R_{18}$, $R_{19}$ and $R_{20}$ substituents of G is selected from the group consisting of hydrogen, —$CH_3$, —$CF_3$, —$OCH_3$, F and OH; when $R_{18}$ is hydrogen and $R_{19}$ and $R_{20}$ are on adjacent carbon atoms then $R_{19}$ and $R_{20}$ can together form a structure of the formula —O(—$CH_2$)$_m$—O— wherein m is 1 or 2 such as

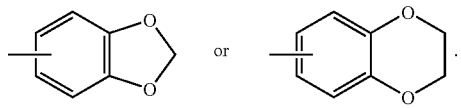

In some such embodiments, G is selected from the group consisting of 4-methylphenyl-1-yl, 2-trifluoromethylphenyl-1-yl, phenyl, 4-hydroxyphenyl-1-yl, 4-fluorophenyl-1-yl, 3-methoxyphenyl-1-yl and

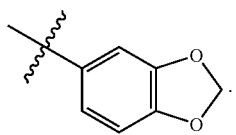

In some embodiments of the compounds of the invention, B has the structure of (a) or (b). In other embodiments, B has the structure of (c). In some embodiments, the present invention provides the compounds 10-[(2,2'-Dimethyl-1,1'-biphenyl-4-yl)carbonyl]-N-(3-methoxybenzyl)-10,11-dihydro-5H-pyrrolo[2,1-c][1,4]benzodiazepine-3-carboxamide, 10-[(2,2'-Dimethyl-1,1'-biphenyl-4-yl)carbonyl]-N-(4-methylbenzyl)-10,11-dihydro-5H-pyrrolo[2,1-c][1,4]benzodiazepine-3-carboxamide, N-(1,3-Benzodioxol-5-ylmethyl)-10-[(2,2'-dimethyl-1,1'-biphenyl-4-yl)carbonyl]-10,11-dihydro-5H-pyrrolo[2,1-c][1,4]benzodiazepine-3-carboxamide, 10-[(2,2'-Dimethyl-1,1'-biphenyl-4-yl)carbonyl]-N-[2-(4-hydroxyphenyl)ethyl]-10,11-dihydro-5H-pyrrolo[2,1-c][1,4]benzodiazepine-3-carboxamide, 10-[(2-Methoxy-2'-methyl-1,1'-biphenyl-4-yl)carbonyl]-N-(4-methylbenzyl)-10,11-dihydro-5H-pyrrolo[2,1-c][1,4]benzodiazepine-3-carboxamide, N-(1,3-Benzodioxol-5-ylmethyl)-10-[(2-methoxy-2'-methyl-1,1'-biphenyl-4-yl)carbonyl]-10,11-dihydro-5H-pyrrolo[2,1-c][1,4]benzodiazepine-3-carboxamide, N-Benzyl-10-[(2-methoxy-2'-methyl-1,1'-biphenyl-4-yl)carbonyl]-10,11-dihydro-5H-pyrrolo[2,1-c][1,4]benzodiazepine-3-carboxamide, and N-(4-Fluorobenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide.

In further embodiments, the present invention provides the compounds described as Examples 1-104, hereinbelow.

Also provided in accordance with the invention are compositions comprising a pharmaceutically effective amount of a compound according to the invention, and a pharmaceutically acceptable carrier or excipient.

The present invention also provides methods for using the compounds disclosed herein. In some embodiments, the invention provides methods of inhibiting fertility comprising administering to a mammal, e.g., a human, an effective amount of a compound of the invention. In some embodiments, the invention provides methods for preventing conception, which comprises administering to a mammal an effective amount of a compound of the invention. In some such embodiments, the mammal can be a female; in other embodiments, the mammal is male. When the mammal of such method is female, the onset of pregnancy is prevented in the female mammal, while when the mammal is male, onset of pregnancy is prevented in a second mammal that is female.

In further embodiments of the methods of the invention, FSH-mediated follicular development is blocked by the administration to a mammal of an effective amount of a compound of the invention.

The invention is to be understood as embracing all simultaneous, sequential or separate use of any combination of the compounds of the invention with any pharmaceutical composition useful in the methods described herein.

In some embodiments, the present invention provides methods of inhibiting fertility. In some embodiments, the methods include administering to a mammal an effective amount of at least one compound as described herein, or a pharmaceutically acceptable salt thereof. In some embodiments, the methods further comprise identifying a mammal in need of contraception.

In some embodiments, the methods include administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt or free acid forms; i.e., includes the administration of such compounds each in the acid form, or each in the salt form, or one or more in the acid form and one or more in the salt form, in any proportion of the compounds and/or salts.

As used herein, the term "effective amount" when applied to a compound of the invention, is intended to denote an amount sufficient to cause the intended biological effect. In some embodiments, the methods of the invention provide for administration of combinations of compounds. In such instances, the "effective amount" is the amount of the combination sufficient to cause the intended biological effect.

The term "alkyl", employed alone or as part of a group, is defined herein, unless otherwise stated, as either a straight-chain or branched saturated hydrocarbon of 1 to 10 carbon atoms. In some embodiments, the alkyl moiety contains 1 to 10, 1 to 8, 1 to 6, 1 to 4, 1 to 3 or 1 carbon atoms. Where the term "alkyl" appears herein without a carbon atom range it means a range of $C_1$-$C_{10}$. Examples of saturated hydrocarbon alkyl moieties include, but are not limited to, chemical groups such as methyl, ethyl, n-propyl, isopropyl, n-butyl, tert-butyl, isobutyl, sec-butyl, n-pentyl, n-hexyl, and the like.

The term "alkoxy", employed alone or in combination with other terms, is defined herein, unless otherwise stated, as —O-alkyl. Examples of alkoxy moieties include, but are not limited to, chemical groups such as methoxy, ethoxy, isopropoxy, sec-butoxy, tert-butoxy, and homologs, isomers, and the like.

As used herein, the term "cycloalkyl," employed alone or in combination with other terms, is defined herein, unless otherwise stated, as a cyclized alkyl group having from 3 to 8 ring carbon atoms.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, and the like.

The term "aryloxy" employed alone or in combination with other terms, is defined herein, unless otherwise stated, as a group of formula —O-aryl, where the term "aryl" has the definition as previously described herein.

The term "arylalkyl" or "aralkyl" employed alone or in combination with other terms, is defined herein, unless otherwise stated, as an alkyl, as herein before defined, substituted with an aryl moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "acyl" employed alone or in combination with other terms, is defined herein, unless otherwise stated, as groups of formula —C(O)-alkyl of 2 to 7 carbon atoms.

The term "alkoxyalkyl" employed alone or in combination with other terms, is defined herein, unless otherwise stated, as -alkyl-alkoxy where the terms "alkyl" and "alkoxy" have the definitions as previously described herein.

The term "carbalkoxy" employed alone or in combination with other terms, is defined herein, unless otherwise stated, as alkoxycarbonyl, e.g., —COOCH$_3$.

The term "aminoalkyl" employed alone or in combination with other terms, is defined herein, unless otherwise stated, as alkyl-amino, wherein the term "alkyl" has the definition as previously described herein and the term "amino" is —NH$_2$ or —NH—.

The term "alkylamino" employed alone or in combination with other terms, is defined herein, unless otherwise stated, as —NH-alkyl, wherein the term "alkyl" has the definition as previously described herein.

The terms "inhibit," "inhibiting," "block," or "blocking" as used herein mean to retard, arrest, restrain, impede or obstruct the progress of a system, condition or state.

The terms "prevent" or "preventing" as used herein mean to keep from happening or existing.

The term "administering" as used herein means either directly administering the compounds of the present invention, or administering a prodrug, derivative, or analog of the the compounds of the present invention that will form an effective amount of the compounds of the present invention within a mammal.

The compositions of the present invention may be adapted to any mode of administration, including intravenous administration such as subcutaneous, intraperitoneal, or intramuscular, bolus and infusion, and oral administration.

The compounds of the present invention can be used in the form of salts derived from non toxic pharmaceutical acceptable acids or bases. These salts include without limitation the following: salts with inorganic acids, e.g., hydrochloric acid, hydrobromic acid, sulfuric acid, nitric acid, phosphoric acid, and organic acids such as acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium or magnesium, or with organic bases, including quaternary ammonium salts.

The compounds of the present invention can also be used in the form of esters, carbamates and other conventional prodrug forms, which generally will be functional derivatives of the compounds of this invention that are readily converted to the active moiety in vivo. Also included are metabolites of the compounds of the present invention defined as active species produced upon introduction of these compounds into a biological system.

When the compounds of this invention are employed as described above, they may be combined with one or more pharmaceutically acceptable excipients or carriers, e.g, solvents, diluents and the like. Such pharmaceutical preparations may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such preparations may contain, for example, from about 25 to about 90% of the active ingredient in combination with the carrier, more usually between about 5% and 60% by weight. The effective dosage of active ingredients employed may vary depending on the particular compound or salt employed, the mode of administration, age, weight, sex and medical condition of the patient, and the severity of the condition being treated. The selection of the appropriate administration and dosage forms for an individual mammal will be apparent to those skilled in the art. Such determinations are routine to a physician, veterinarian or clinician of ordinary skill in the art (see for example, *Harrison's Principles of Internal Medicine* (1998), edited by Anthony Fauci et al., 14$^{th}$ edition, published by McGraw Hill). Further, the dosage regimen may be adjusted to provide the optimal therapeutic response. For example, several divided doses may be administered daily or the dose may be proportionally reduced as indicated by the needs of the therapeutic situation.

These active compounds of the present invention may be administered orally as well as by intravenous, intramuscular, or subcutaneous routes. Solid carriers, for example, starch, lactose, dicalcium phosphate, microcrystalline cellulose, sucrose and kaolin, liquid carriers, for example, sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Examples of adjuvants include flavoring agents, coloring agents, preserving agents, and antioxidants, such as vitamin E, ascorbic acid, BHT and BHA.

These active compounds also may be administered parenterally or intraperitoneally. Solutions or suspensions of these active compounds as a free base or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations shall contain a preservative to prevent the growth of microorganisms under ordinary conditions of storage and use.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol, polyol (e. g., glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally, e.g., using transdermal skin patches known to those ordinarily skilled in the art. Transdermal administration further include all administrations across the surface of the body and the inner linings of bodily passages including epithelial and mucosal tissues, using carrier systems such as lotions, creams, foams, patches, suspensions, solutions, and suppositories (rectal and vaginal). When using a transdermal delivery system, the dosage administration will be continuous rather than in a single or divided daily doses. The compounds of the present invention can also be administered in the form of a liposome delivery system wherein the liposomal lipid bilayer are formed from a variety of phospholipids.

Compounds of the present invention may be delivered by the use of carriers such as monoclonal antibodies to which the active compounds are coupled. The compounds of the present invention also may be coupled to soluble polymers as drug carriers or to biodegradable polymers useful in achieving controlled release of the active agent.

It is understood by those practicing the art that some of the compounds of this invention depending on the definition of R, $R_1$, $R_2$, $R_3$, and B may contain one or more asymmetric centers, and thus may give rise to enantiomers and diastereomers. The present invention includes all stereoisomers including individual diastereomers and resolved, enantiomerically pure R and S stereoisomers, as well as racemates, and all other mixtures of R and S stereoisomers and pharmaceutically acceptable salts thereof, which possess the indicated activity. Optical isomers may be obtained in pure form by standard procedures known to those skilled in the art, and include, but are not limited to, diastereomeric salt formation, kinetic resolution, and asymmetric synthesis. It is also understood that this invention encompasses all possible regioisomers, E-Z isomers, endo-exo isomers, and mixtures thereof that possess the indicated activity. Such isomers can be obtained in pure form by standard procedures known to those skilled in the art, and include, but are not limited to, column chromatography, thin-layer chromatography, and high-performance liquid chromatography. It is understood by those practicing the art that some of the compounds of this invention depending on the definition of B may be chiral due to hindered rotation, and give rise to atropisomers, which can be resolved and obtained in pure form by standard procedures known to those skilled in the art. Also included in this invention are all polymorphs and hydrates of the compounds of the present invention.

Also according to the present invention there are provided processes for producing the compounds of the present invention.

PROCESS OF THE INVENTION

The compounds of the present invention may be prepared according to one of the general processes outlined below.

The compounds of general formula (I), wherein A is —C=O and B is (a), (b), or (c) as defined hereinbefore, can be conveniently prepared as shown in Scheme I.

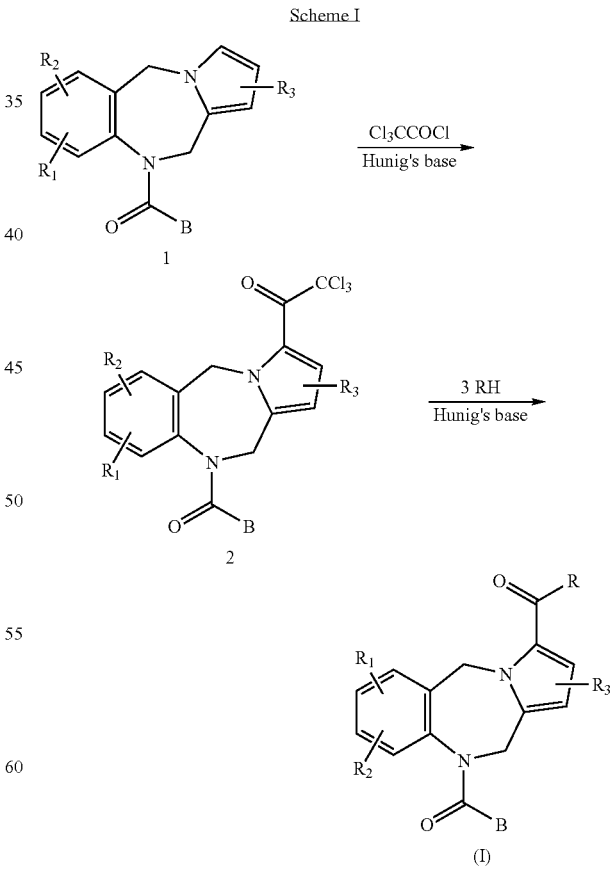

According to Scheme 1, a tricyclic diazepine of formula (1) wherein $R_1$, $R_2$, $R_3$ and B are defined hereinbefore, is reacted with a perhaloalkanoyl halide, for example, trichloroacetyl chloride, in the presence of an organic base such as N,N-diisopropylethyl amine (Hünig's base) in an aprotic organic solvent such as dichloromethane or 1,4-dioxane, at temperatures ranging from −10° C. to ambient to provide the desired trichloroacetyl intermediate of formula (2). Subsequent reaction of (2) with an appropriately substituted primary or secondary amine of formula (3) in refluxing 1,4-dioxane or with dimethylsulfoxide optionally in the presence of an organic base such as triethylamine in a solvent such as acetonitrile, at temperatures ranging from ambient to the refluxing temperature of the solvent, yields the desired compound of formula (I) wherein $R_1$, $R_2$, $R_3$, and B are as defined hereinbefore.

The compounds of formula (I) can be also prepared by the process shown in Scheme II below.

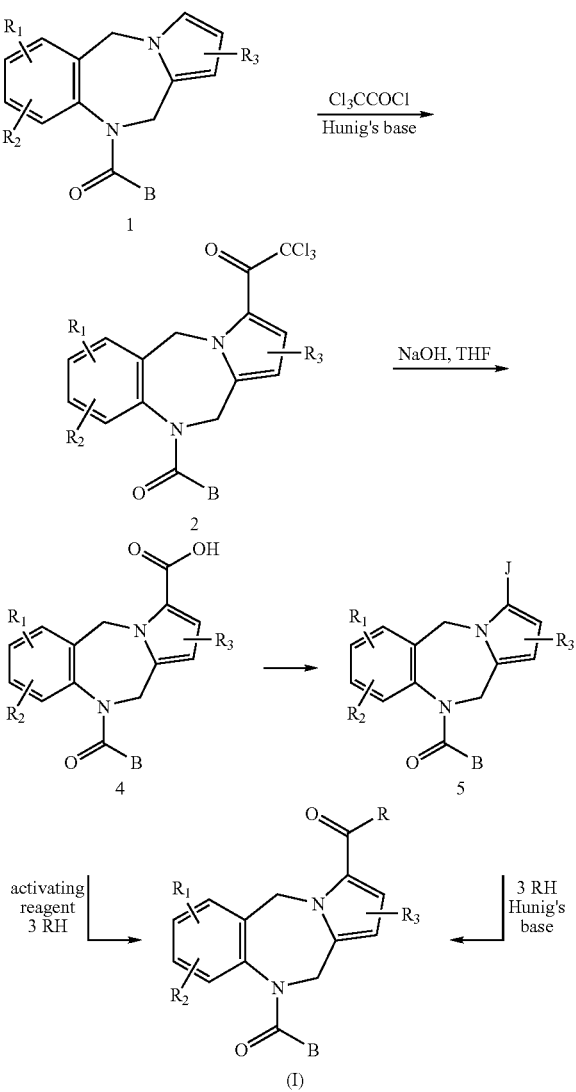

According to Scheme II the trichloroacetyl intermediate of formula (2) is hydrolyzed with aqueous base such as sodium hydroxide, in an organic solvent such as tetrahydrofuran or acetone, at temperatures ranging from −10° C. to ambient, to yield the intermediate acid of formula (4). The required activation of the carboxylic acid (4) for the subsequent coupling with a primary or secondary amine of formula (3) can be accomplished in several ways. Thus, (4) can be converted to an acid halide such as a chloride or bromide of formula (5, J=COCl or COBr by reaction with thionyl chloride (or bromide) or oxalyl chloride (or bromide) or similar reagents known in the art, either neat or in the presence of an inorganic base such as potassium carbonate, or in the presence of an organic base such as pyridine, 4-(dimethylamino)pyridine, or a tertiary amine such as triethylamine, in an aprotic solvent such as dichloromethane, N,N-dimethylformamide or tetrahydrofuran, at temperatures ranging from −5° C. to 50° C., to yield the intermediate acylated derivative (5). Subsequent coupling of the acid chloride (or bromide) (5, J=COCl or COBr) with an appropriately substituted primary or secondary amine of formula (3) in the presence of a stoichiometric amount of Hünig's base, in an aprotic solvent such as dichloromethane, N,N-dimethylformamide or tetrahydrofuran, at temperatures ranging from ambient to the reflux temperature of the solvent, provides the desired compounds of formula (I) wherein $R_1$, $R_2$, $R_3$ and B are as defined hereinbefore.

Alternatively, the acylating species can be a mixed anhydride of the corresponding carboxylic acid, such as that prepared by treating the acid of formula (4) with 2,4,6-trichlorobenzoyl chloride, in an aprotic organic solvent, such as dichloromethane, according to the procedure of Inanaga et al., in Bull. Chem. Soc. Jpn. 52, 1989 (1979). Treatment of said mixed anhydride of formula (5) with an appropriately substituted primary or secondary amine of formula (3) in an aprotic solvent such as dichloromethane, at temperatures ranging from ambient to the reflux temperature of the solvent, provides the desired compounds of formula (I) wherein $R_1$, $R_2$, $R_3$ and B are as defined hereinbefore.

Alternatively, amidation of the carboxylic acids of formula (4) can be effectively carried out by treatment of said acid with triphosgene in an aprotic solvent such as dichloromethane followed by reaction of the activated intermediate with an appropriately substituted primary or secondary amine of formula (3) in the presence of an organic base such as Hünig's base, at temperatures ranging from −10° C. to ambient.

Another process for the preparation of the compounds of the present invention of formula (I) consists of treating the acid of formula (4) with an activating reagent, such as N,N-dicyclohexylcarbodiimide or 1-ethyl-3-(3-dimethylaminopropyl) carbodiimide hydrochloride, in the presence of 1-hydroxybenzotriazole followed by reaction of the activated intermediate with an appropriately substituted primary or secondary amine of formula (3). In some embodiments of this process, the reaction of the activated intermediate with an appropriately substituted primary or secondary amine of formula (3) is performed in the presence of an organic base such as Hünig's base and a catalytic amount of 4-(dimethylamino) pyridine in an aprotic solvent such as dichloromethane, N,N-dimethylformamide or tetrahydrofuran, at temperatures ranging from −10° C. to ambient.

In another process for the preparation of the compounds of the present invention, the acid (4) can be activated by treatment with other activating agents such as N,N′-carbonyldiimidazole, in an aprotic solvent such as dichloromethane or tetrahydrofuran, at temperatures ranging from −10° C. to the reflux temperature of the solvent. Subsequent reaction of the activated intermediate imidazolide with an appropriately substituted primary or secondary amine of formula (3) provides the desired compounds of formula (I), wherein $R_1$, $R_2$, $R_3$ and B are as defined hereinbefore.

Alternatively, the coupling of the appropriately substituted primary or secondary amine of formula (3) with the acid of formula (4) can be effectively carried out by using hydroxybenzotriazole tetramethyluronium hexafluorophosphate as the coupling reagent in the presence of an organic base such as Hünig's base, and in a solvent such as N,N-dimethylformamide, at temperatures ranging from −10° C. to ambient, to provide in good isolated yield and purity the desired compounds of formula (I), wherein $R_1$, $R_2$, $R_3$ and B are as defined hereinbefore.

Related coupling reagents such as diphenylphosphoryl azide, diethyl cyano phosphonate, benzotriazol-1-yl-oxy-tris-(dimethylamino) phosphonium hexafluorophosphate and all other reagents known in the literature that have been used in the formation of amide bonds in peptide synthesis can also be used for the preparation of compounds of formula (I), as described hereinbefore.

The method of choice for the preparation of compounds of formula (I) from the intermediate carboxylic acid (4) is ultimately chosen on the basis of its compatibility with the $R_1$, $R_2$, $R_3$ and B groups, and its reactivity with the tricyclic diazepine of formula (1).

Another process for the preparation of compounds of formula (I)) of Scheme I is shown in Scheme III. A tricyclic diazepine of formula (1) is reacted with diphosgene in an aprotic solvent such as dichloromethane, and in some embodiments of this process, in the presence of an organic base such as triethylamine, followed by reaction of the resulting acylated intermediate with an appropriately substituted primary or secondary amine of formula (3), to provide the desired compounds of formula (I) wherein $R_1$, $R_2$, $R_3$ and B are as defined hereinbefore.

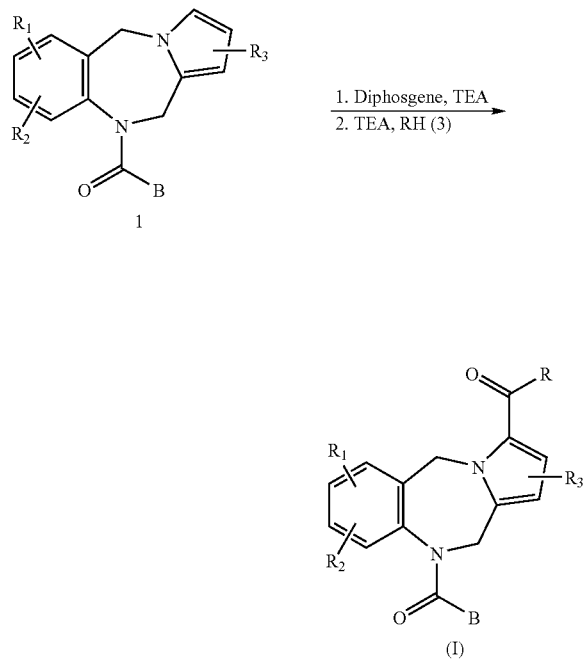

The tricyclic diazepines of formula (1) of Scheme I, wherein A is —C═O and B is defined hereinbefore, can be conveniently prepared as shown in Scheme IV.

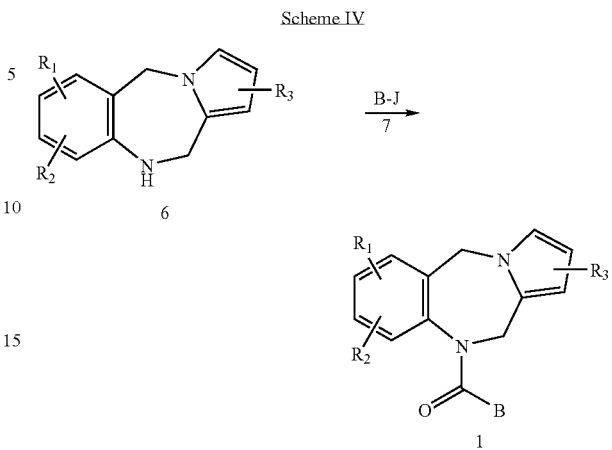

Thus, a tricyclic diazepine of formula (6) is treated with an appropriately substituted acylating agent, such as an appropriately substituted acyl chloride (or bromide) of formula (7, J═COCl or COBR) wherein B is ultimately chosen on the basis of its compatibility with the present reaction scheme, in the presence of an inorganic base such as potassium carbonate, or in the presence of an organic base such as. pyridine, 4-(dimethylamino)pyridine, or a tertiary amine such as triethylamine, N,N-diisopropylethyl amine or N,N-dimethylaniline, in an aprotic solvent such as dichloromethane, N,N-dimethylformamide, tetrahydrofuran or 1,4-dioxane, at temperatures ranging from −5° C. to 50° C. to provide intermediates of general formula (1).

Alternatively, the acylating species of formula (7) can be a mixed anhydride of the corresponding carboxylic acid, such as that prepared by treating the acid with 2,4,6-trichlorobenzoyl chloride, in an aprotic organic solvent such as dichloromethane according to the procedure of Inanaga et al., in *Bull. Chem. Soc. Jpn.*, 52, 1989 (1979). Treatment of said mixed anhydride of general formula (7) with a tricyclic diazepine of formula (6) in a solvent such as dichloromethane and in the presence of an organic base such as 4-(dimethylamino) pyridine, at temperatures ranging from 0° C. to the reflux temperature of the solvent, yields the intermediate acylated derivative (1) of Scheme IV.

The acylating intermediate of formula (7) is ultimately chosen on the basis of its compatibility with the B group and its reactivity with the tricyclic diazepine of formula (6).

The desired intermediates of formula (7) of Scheme IV wherein B is (a) can be conveniently prepared by a process shown in Scheme V. Thus, an appropriately substituted aryl iodide (bromide, chloride, or trifluoromethane sulfonate) of formula (8, wherein P is a carboxylic acid protecting group, for example, P=alkyl or benzyl, M═I, Br, Cl, OTf, and $R_5$, $R_6$ and $R_7$ are defined hereinbefore), is reacted with an aryl tri(alkyl)tin(IV) derivative of formula (9, T═Sn(alkyl)$_3$, for example, Sn(n-Bu)$_3$), wherein $R_8$, $R_9$ and $R_{10}$ are defined hereinbefore, in the presence of a Pd(0) catalyst, and in the presence or absence of inorganic salts (e.g. LiCl or copper(I) salts), to provide the intermediate ester (10). Subsequent unmasking of the carboxylic acid by hydrolysis, hydrogenolysis or similar methods known in the art, followed by activation of the intermediate acid (11), provides the desired intermediates of formula (7), wherein $R_5$, $R_6$, $R_7$, $R_8$, $R_9$ and $R_{10}$ are hereinbefore defined, which are suitable for coupling with the tricyclic diazepine of formula (6).

Scheme V

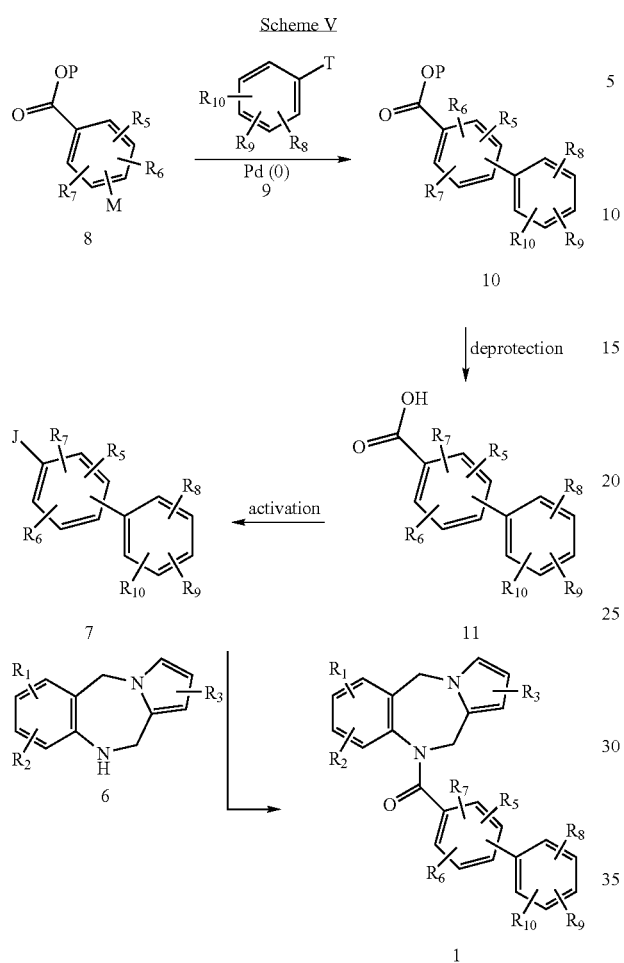

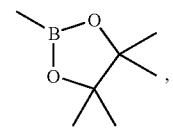

bromide (8, M=Br) and the boronic acid (9) in a solvent such as dioxane in the presence of potassium phosphate and a Pd(0) catalyst.

Alternatively, a palladium-catalyzed cross coupling reaction of an aryl halide (or trifluoromethanesulfonate) of formula (9, T=Br, I, OTf) with a pinacolato boronate [boronic acid, or trialkyl tin(IV)] derivative of formula (8, M=

B(OH)$_2$, or SnBu$_3$) yields the desired intermediate of formula (10), which is converted to (1) in the manner of Scheme V.

The desired intermediates of formula (10) of Scheme V wherein B is (b) can be prepared in analogous fashion by replacing intermediates of formula (9) with appropriately substituted naphthyl intermediates.

The required appropriately substituted aryl halides of formula (8, M=Br or I) of Scheme V are either available commercially, or are known in the art, or can be readily accessed in quantitative yields and high purity by diazotization of the corresponding substituted anilines (8, P=H, alkyl or benzyl, M=NH$_2$) followed by reaction of the intermediate diazonium salt with iodine and potassium iodide in aqueous acidic medium, essentially according to the procedures of Street et al,. *J. Med. Chem.* 36, 1529 (1993) and Coffen et al., *J. Org. Chem.* 49, 296 (1984), respectively, or with copper(I) bromide (March, *Advanced Organic Chemistry*, 3$^{rd}$ ed., p. 647-648, John Wiley & Sons, New York (1985)).

The desired intermediates of formula (7) of Scheme IV wherein B is (b) can be prepared by a process analogous to that exemplified in Scheme V by replacing intermediates of formula (9) with appropriately substituted naphthyl intermediates.

Alternatively, the desired intermediates of formula (10) of Scheme V wherein B is (a) can be prepared by coupling of the iodide (bromide, chloride, or trifluoromethanesulfonate) (8, M=I, Br, Cl, or OTf) with an appropriately substituted aryl boron derivative of formula (9, e.g., T=B(OH)$_2$) in the presence of a palladium catalyst such as palladium(II) acetate or tetrakis(triphenylphosphine) palladium(0) and an organic base such as triethylamine or an inorganic base such as sodium (potassium or cesium) carbonate, with or without added tetrabutylammonium bromide (iodide), in a mixture of solvents such as toluene-ethanol-water, acetone-water, water or water-acetonitrile, at temperatures ranging from ambient to the reflux temperature of the solvent (Suzuki, *Pure & Appl. Chem.* 66, 213-222 (1994), Badone et al., *J. Org. Chem.* 62, 7170-7173 (1997); Wolfe et al. *J. Am. Chem. Soc.* 121, 9559 (1999); Shen, *Tetr. Letters* 38, 5575 (1997)). The exact conditions for the Suzuki coupling of the halide and the boronic acid intermediates are chosen on the basis of the nature of the substrate and the substituents. The desired intermediate of formula (10) of Scheme V similarly can be prepared from the Alternatively, the desired intermediates of formula (11) of Scheme V wherein B is (a) can be conveniently prepared as shown in Scheme VI by a cross-coupling reaction of an appropriately substituted pinacolato boronate of formula (13), wherein R$_8$, R$_9$ and R$_{10}$ are hereinbefore defined, with an aryl triflate or an aryl halide of formula (14, Q=OTf, Br, I), wherein R$_5$, R$_6$ and R$_7$ are defined hereinbefore, according to the general procedures of Ishiyama et al., *Tetr. Lett.* 38, 3447-3450 (1997) and Giroux et al. *Tetr. Lett.* 38, 3841-3844 (1997), followed by basic or acidic hydrolysis of the intermediate nitrile of formula (15) (cf. March, *Advanced Organic Chemistry*, 3$^{rd}$ ed., John Wiley & Sons, New York, p. 788 (1985)).

Scheme VI

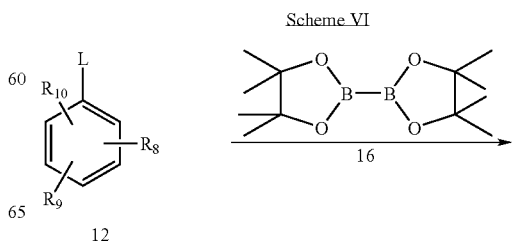

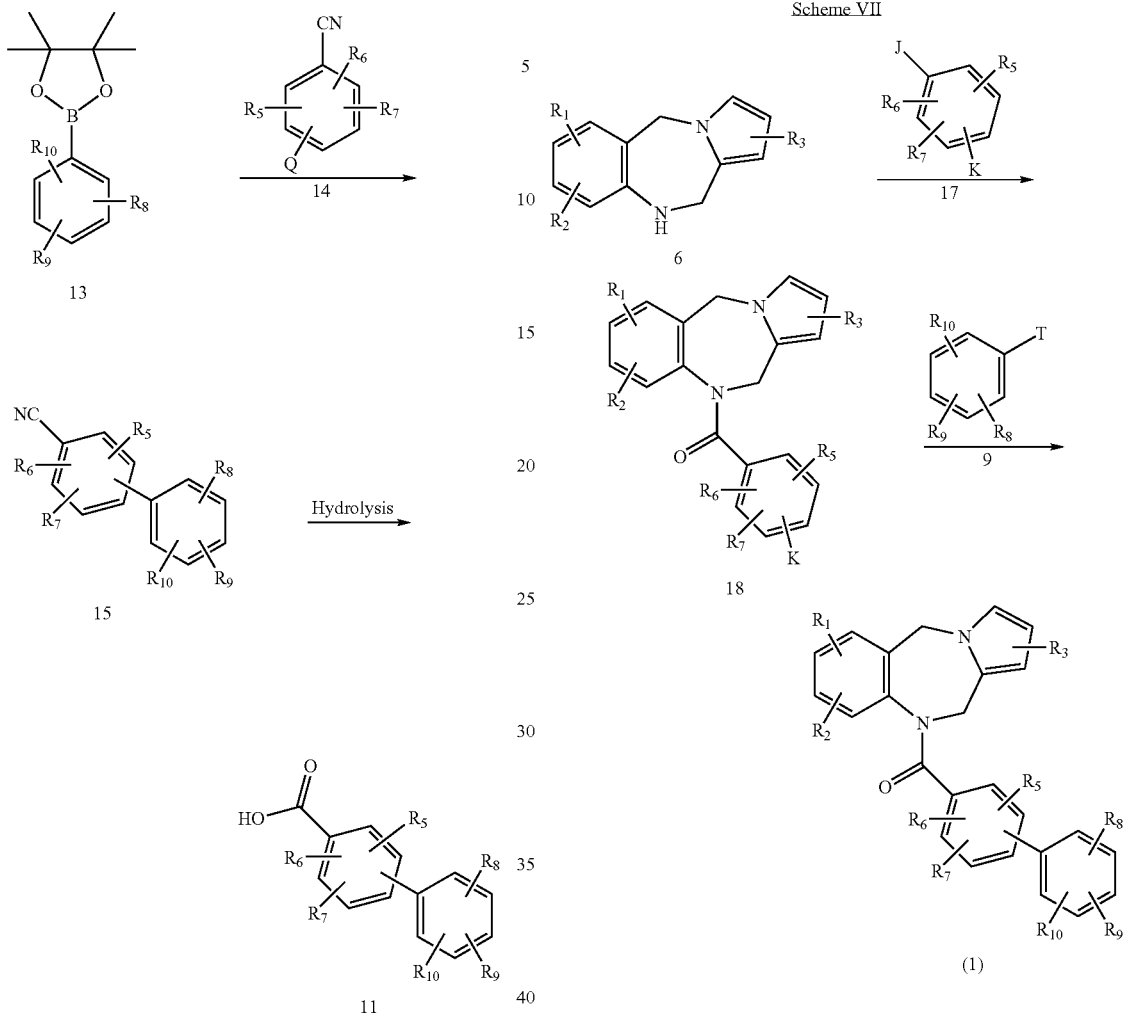

Alternatively, reaction of an iodide (bromide, chloride, or trifluoromethanesulfonate) of formula (12, L=Br, Cl, I, or OTf) with a boronic acid [or trialkyl tin(IV)] derivative of formula (14, Q=B(OH)$_2$, or SnBu$_3$) yields the desired intermediate of formula (15), which is converted to (11) in the manner of Scheme VI.

The desired intermediates of formula (15) of Scheme VI wherein B is (b) can be prepared in analogous fashion by replacing intermediates of formulas (13) with appropriately substituted naphthyl intermediates.

The desired phenyl boronic esters of formula (13) of Scheme VI can be conveniently prepared by the palladium-catalyzed cross-coupling reaction of bis(pinacolato)diboron (16) with an appropriately substituted aryl halide such as a bromide or iodide (12, L=Br, I) or aryl triflate (12, L=OTf, according to the described procedures of Ishiyama et al., *J. Org. Chem.* 60, 7508-7510 (1995) and Giroux et al., *Tetr. Lett.* 38, 3841-3844 (1997).

The desired compounds of formula (1) of Scheme IV wherein A is —C═O and B is (a) can be alternatively prepared by a process shown in Scheme VII.

Thus, a tricyclic diazepine of formula (6) is treated with an appropriately substituted acylating agent such as a halo aroyl halide, for example, an iodo (bromo) aroyl chloride (bromide) of formula (17, J=COCl or COBr; K=I, Br), wherein R$_5$, R$_6$ and R$_7$ are hereinbefore defined, using any of the procedures hereinbefore described, to provide the acylated intermediate of general formula (18) of Scheme VII.

Alternatively, the acylating species of formula (17) can be a mixed anhydride of the corresponding carboxylic acid. Treatment of said mixed anhydride of general formula (17) with a tricyclic diazepine of formula (6) according to the procedure described hereinbefore yields the intermediate acylated derivative (18).

The acylating intermediate of formula (17) is ultimately chosen on the basis of its compatibility with the R$_5$, R$_6$ and R$_7$ groups, and its reactivity with the tricyclic diazepine of formula (6).

A Stille coupling reaction of (18, K═I) with an appropriately substituted organotin reagent such as a trialkyltin(IV) derivative, e.g., a tri-n-butyltin(IV) derivative of formula (9, T=SnBu$_3$), wherein R$_8$, R$_9$ and R$_{10}$ are hereinbefore defined, in the presence of a catalyst such as tetrakis(triphenylphosphine) palladium (0), in an aprotic organic solvent such as toluene and N,N-dimethylformamide, at temperatures ranging from ambient to 150° C. (cf. Farina et al., *J. Org. Chem,* 59, 5905 (1994) and references cited therein) affords the desired compounds of formula (1), wherein $R_1$, $R_2$, $R_3$, $R_5$, $R_6$, $R_7$, $R_8$, $R_9$ and $R_{10}$ are as defined hereinbefore.

Alternatively, the reaction of a compound of formula (18, K=Cl, Br or I) with an appropriately substituted aryl boronic acid of formula (9, T=B(OH)$_2$), wherein $R_5$, $R_6$, $R_7$, $R_8$, $R_9$ and $R_{10}$ are hereinbefore defined, in a mixture of solvents such as toluene-ethanol-water, in the presence of a Pd(0) catalyst and a base such as sodium carbonate, at temperatures ranging from ambient to the reflux temperature of the solvent, yields the desired compounds of formula (1), wherein $R_1$, $R_2$, $R_3$, $R_5$, $R_6$, $R_7$, $R_8$, $R_9$ and $R_{10}$ are as defined hereinbefore.

The substituted aroyl chlorides (or bromides) of formula (17) of Scheme VII (K=I, Br; J=COCl or COBr), wherein $R_5$, $R_6$ and $R_7$ are as defined hereinbefore, are either available commercially, or are known in the art, or can be readily prepared by procedures analogous to those in the literature for the known compounds.

The intermediates of formula (9, T=Sn(alkyl)$_3$; e.g, alkyl=n-butyl) of Scheme VII are either commercially available, or can be conveniently prepared as shown in Scheme VIII from the corresponding bromo starting materials of formula (19), wherein $R_8$, $R_9$, and $R_{10}$ are hereinbefore defined, by first reacting them with n-butyl lithium followed by reaction of the intermediate lithiated species with a trialkyl (e.g., trimethyl or tri-n-butyl) tin(IV) chloride.

Scheme VIII

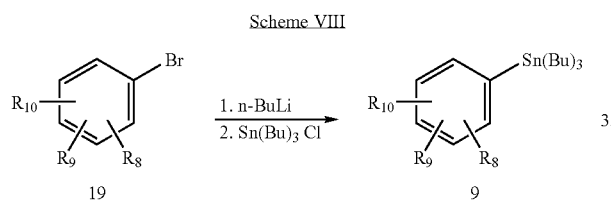

The substituted aryl boronic acids of formula (9, T=B(OH)$_2$) are either available commercially, or are known in the art, or can be readily prepared by procedures analogous to those in the literature for the known compounds.

The desired compounds of formula (1) of Scheme VII wherein A is —C=O and B is (b) can be prepared in analogous fashion by replacing intermediates of formula (9) with appropriately substituted naphthyl intermediates.

Alternatively, as shown in Scheme IX, the appropriately substituted aroyl halides, such as aroyl chlorides of formula (20, J=COCl), wherein $R_5$, $R_6$, and $R_7$ are hereinbefore defined, are reacted with a tricyclic diazepine of formula (6) to provide the intermediate bromides of formula (21). Subsequent reaction of (21) with an hexa alkyl-di-tin (e.g., hexa-n-butyl-di-tin(IV)) in the presence of a Pd(0) catalyst such as tetrakis(tri-phenylphosphine)palladium(0) and lithium chloride or copper(I) salts provides the stannane intermediate of formula (22). Further reaction of the tri-n-butyl tin(IV) derivative (22) with the appropriately substituted aryl halide of formula (23, M=bromo or iodo), wherein $R_8$, $R_9$, and $R_{10}$ are hereinbefore defined, in the presence of a Pd(0) catalyst such as tetrakis(triphenylphosphine) palladium(0), yields the desired compounds of formula (1), wherein $R_1$, $R_2$, $R_3$, $R_5$, $R_6$, $R_7$, $R_8$, $R_9$ and $R_{10}$ are defined hereinbefore.

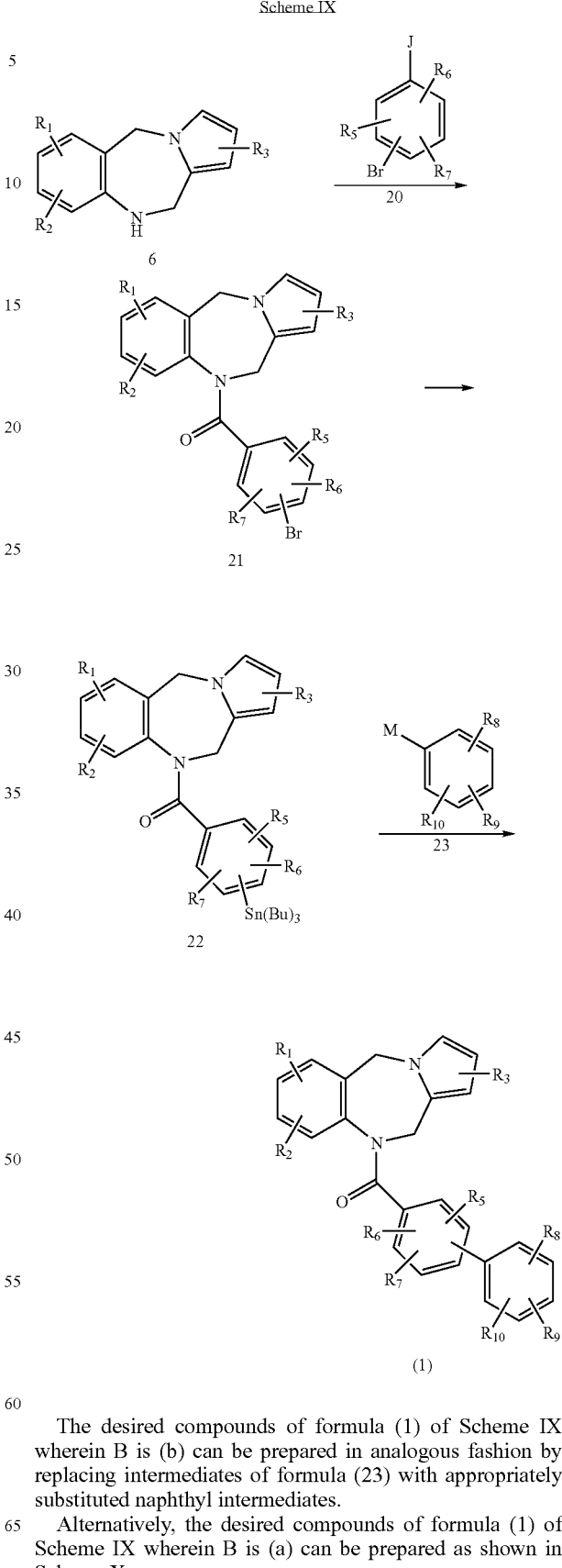

The desired compounds of formula (1) of Scheme IX wherein B is (b) can be prepared in analogous fashion by replacing intermediates of formula (23) with appropriately substituted naphthyl intermediates.

Alternatively, the desired compounds of formula (1) of Scheme IX wherein B is (a) can be prepared as shown in Scheme X.

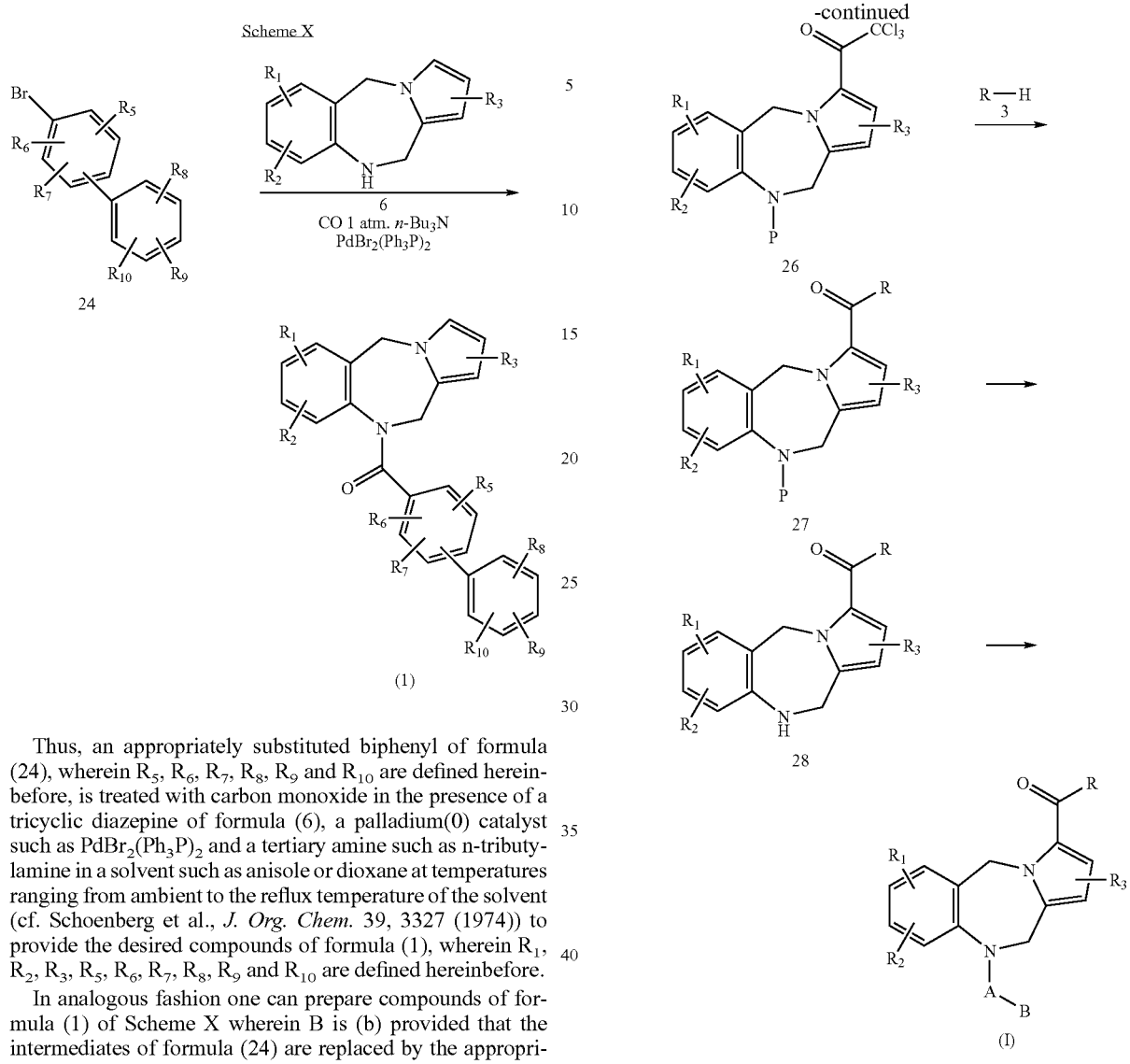

Thus, an appropriately substituted biphenyl of formula (24), wherein $R_5$, $R_6$, $R_7$, $R_8$, $R_9$ and $R_{10}$ are defined hereinbefore, is treated with carbon monoxide in the presence of a tricyclic diazepine of formula (6), a palladium(0) catalyst such as $PdBr_2(Ph_3P)_2$ and a tertiary amine such as n-tributylamine in a solvent such as anisole or dioxane at temperatures ranging from ambient to the reflux temperature of the solvent (cf. Schoenberg et al., *J. Org. Chem.* 39, 3327 (1974)) to provide the desired compounds of formula (1), wherein $R_1$, $R_2$, $R_3$, $R_5$, $R_6$, $R_7$, $R_8$, $R_9$ and $R_{10}$ are defined hereinbefore.

In analogous fashion one can prepare compounds of formula (1) of Scheme X wherein B is (b) provided that the intermediates of formula (24) are replaced by the appropriately substituted naphthyl intermediates.

Another process for the preparation of the desired compounds of general formula (I) Scheme I wherein A is —C═O and B is as defined hereinbefore, is shown in Scheme XI.

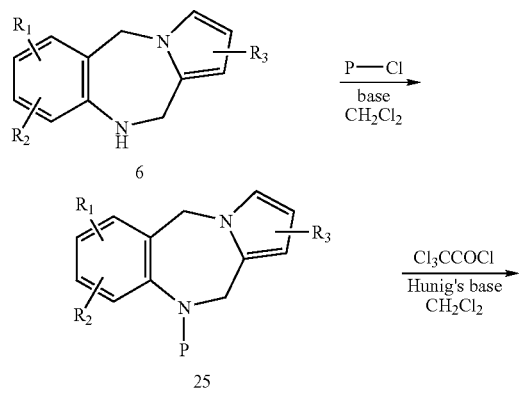

Thus, a tricyclic diazepine of formula (25), wherein $R_1$, $R_2$ and $R_3$ are defined hereinbefore, carrying a protecting group such as a fluorenylalkoxycarbonyl group, e.g., a fluorenylmethyloxycarbonyl (P═Fmoc) group, or an alkoxycarbonyl protecting group such as a tert-butyloxycarbonyl (P═Boc) group, is reacted with a perhaloalkanoyl halide, e.g., trichloroacetyl chloride, in the presence of an organic base such as N,N-diisopropylethyl amine (Hünig's base) or a tertiary amine such as triethylamine, optionally in the presence of catalytic amounts of 4-(dimethylamino)pyridine, in an aprotic organic solvent such as dichloromethane, at temperatures ranging from −10° C. to ambient to provide the desired trichloroacetyl intermediate of formula (26). Subsequent reaction with a primary or secondary amine of formula (3) under the conditions of Scheme I yields the intermediate amide of formula (27, P═Boc), which is then deprotected (intermediate 28) and acylated to the desired product of formula (I). Alternatively, the conversion of (26) to (28) can be carried out in a single step by treatment of (26, P═Fmoc) with a primary amine in the presence of dimethylsulfoxide in an aprotic solvent such as acetonitrile, at the reflux temperature of the solvent.

Alternatively, hydrolysis of the trichloroacetate intermediate (26) with aqueous base such as sodium hydroxide in an organic solvent such as acetone, at temperatures ranging from −10° C. to ambient, is accompanied by simultaneous removal of the protecting group (P=Fmoc) and yields the intermediate acid of formula (29), as shown in Scheme XII. The required amidation of the carboxylic acid (29) can be effectively accomplished by treating (29) with an activating reagent such as N,N-dicyclohexylcarbodiimide or 1-ethyl-3-(3-dimethylaminopropyl) carbodiimide hydrochloride in the presence of 1-hydroxybenzotriazole, followed by reaction of the activated intermediate with an appropriately substituted primary or secondary amine of formula (3), optionally in the presence of Hunig's base or a catalytic amount of 4-(dimethylamino)pyridine, in an aprotic solvent such as dichloromethane, N,N-dimethylformamide or tetrahydrofuran, at temperatures ranging from −10° C. to ambient. Subsequent acylation of the amide (28) under the conditions of Scheme IV provides the desired compounds of formula (I).

base such as N,N-diisopropylethyl amine, in an aprotic solvent such as N,N-dimethylformamide, followed by basic hydrolysis of the intermediate bis-trifluoroacetyl (trichloroacetyl) intermediate of formula (30), optionally with aqueous sodium hydroxide in a protic organic solvent such as ethanol, at temperatures ranging from ambient to the reflux temperature of the solvent, as exemplified in Scheme XIII.

Scheme XIII

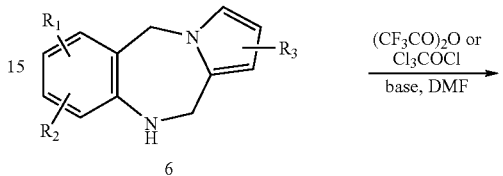

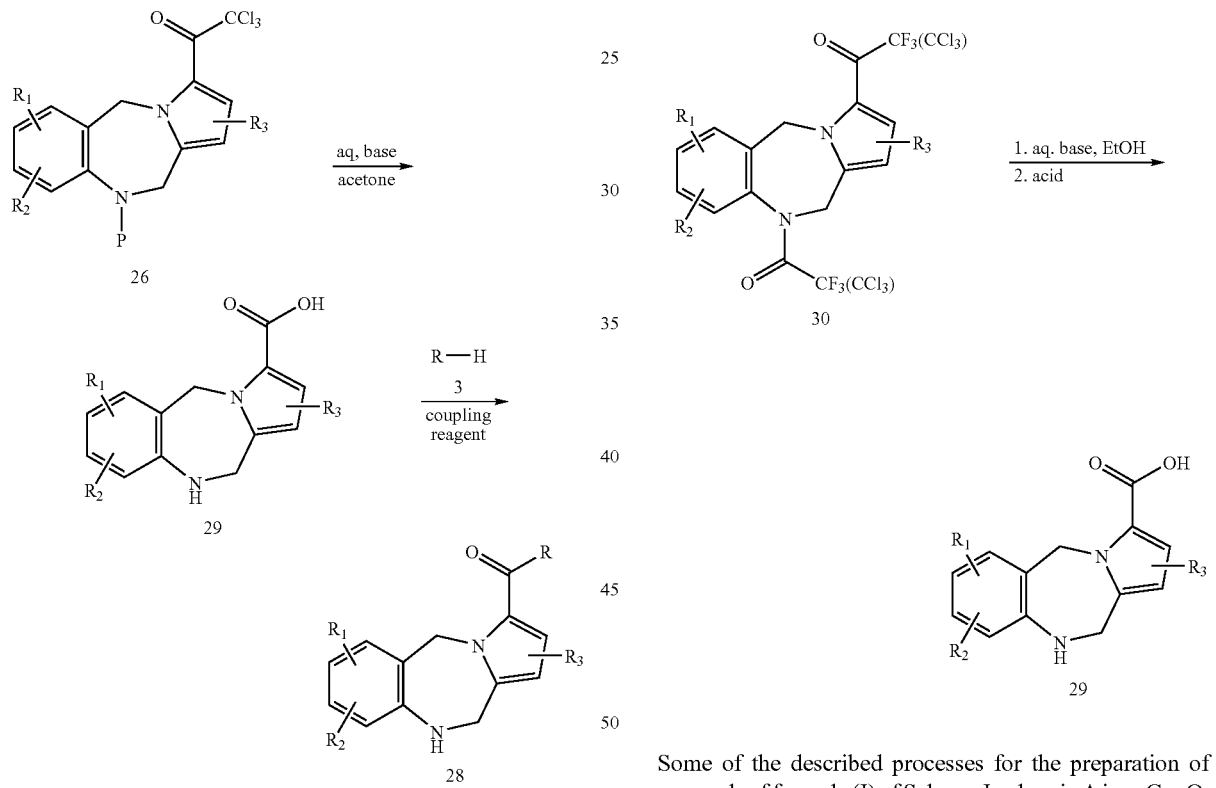

Other coupling reagents known in the literature that have been used in the formation of amide bonds in peptide synthesis also can be used for the preparation of compounds of formula (28). The method of choice for the preparation of compounds of formula (28) from the intermediate carboxylic acid (29) is ultimately chosen on the basis of its compatibility with the $R_1$, $R_2$ and $R_3$ groups.

Alternatively, the intermediate acids of formula (29) of Scheme XII, wherein $R_1$, $R_2$ and $R_3$ are defined hereinbefore, can be obtained by reacting a tricyclic diazepine of formula (6) with an excess of acylating agent such as trifluoroacetic anhydride or trichloroacetyl chloride in the presence of an inorganic base such as potassium carbonate or an organic Some of the described processes for the preparation of compounds of formula (I) of Scheme I, wherein A is —C═O, B is (a), and $R_1$, $R_2$, $R_3$, $R_5$, $R_6$, $R_7$, $R_8$, $R_9$, and $R_{10}$ are defined hereinbefore, also utilize acylation of the amide intermediate (28) of Scheme XII with an acylating agent of formula (17) of Scheme VII, as shown in Scheme XIV. Subsequent coupling of the intermediate (31, K═Br or I) with an appropriately substituted aryl boronic acid (9, T═B(OH)$_2$) in a mixture of solvents such as dimethoxyethane and water or acetonitrile and water, in the presence of a Pd(0) catalyst such as tetrakis(triphenylphosphine)palladium(0) or a Pd(II) catalyst such as [1.1'-bis(diphenylphosphino)ferrocene]dichloro palladium (II), and a base such as potassium or sodium carbonate, at temperatures ranging from ambient to reflux, yields the desired compound (I).

Scheme XIV

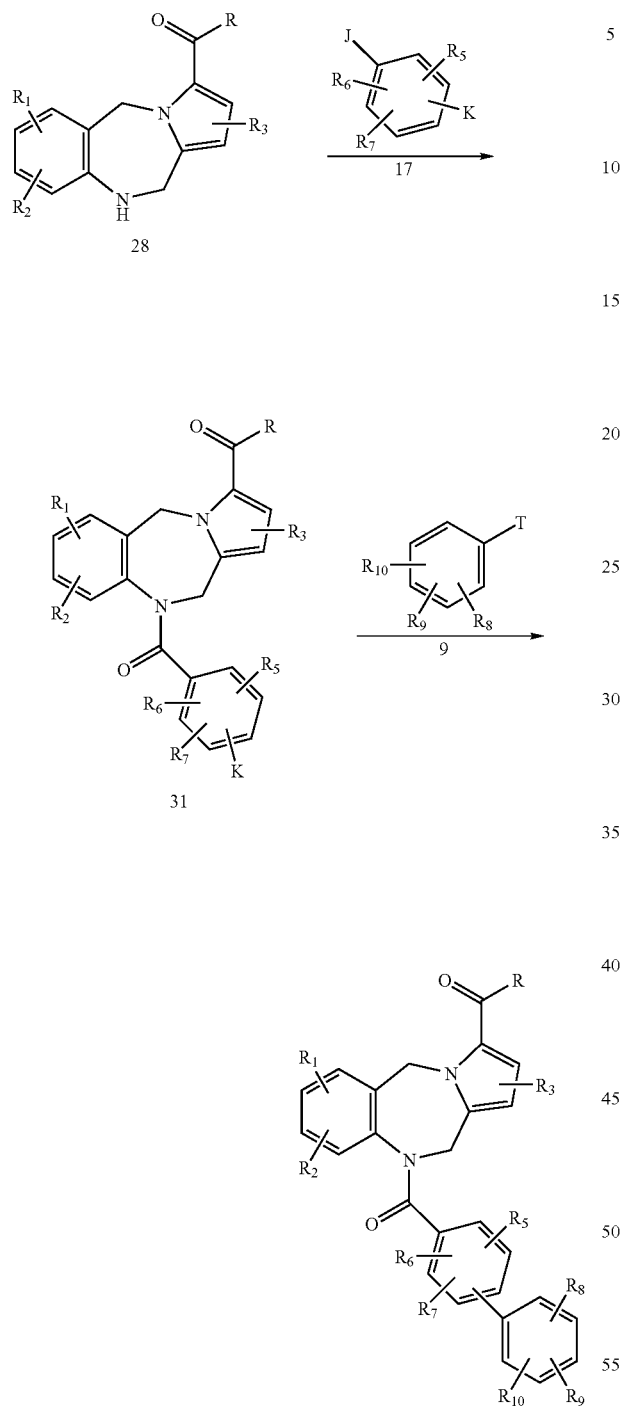

Scheme XV

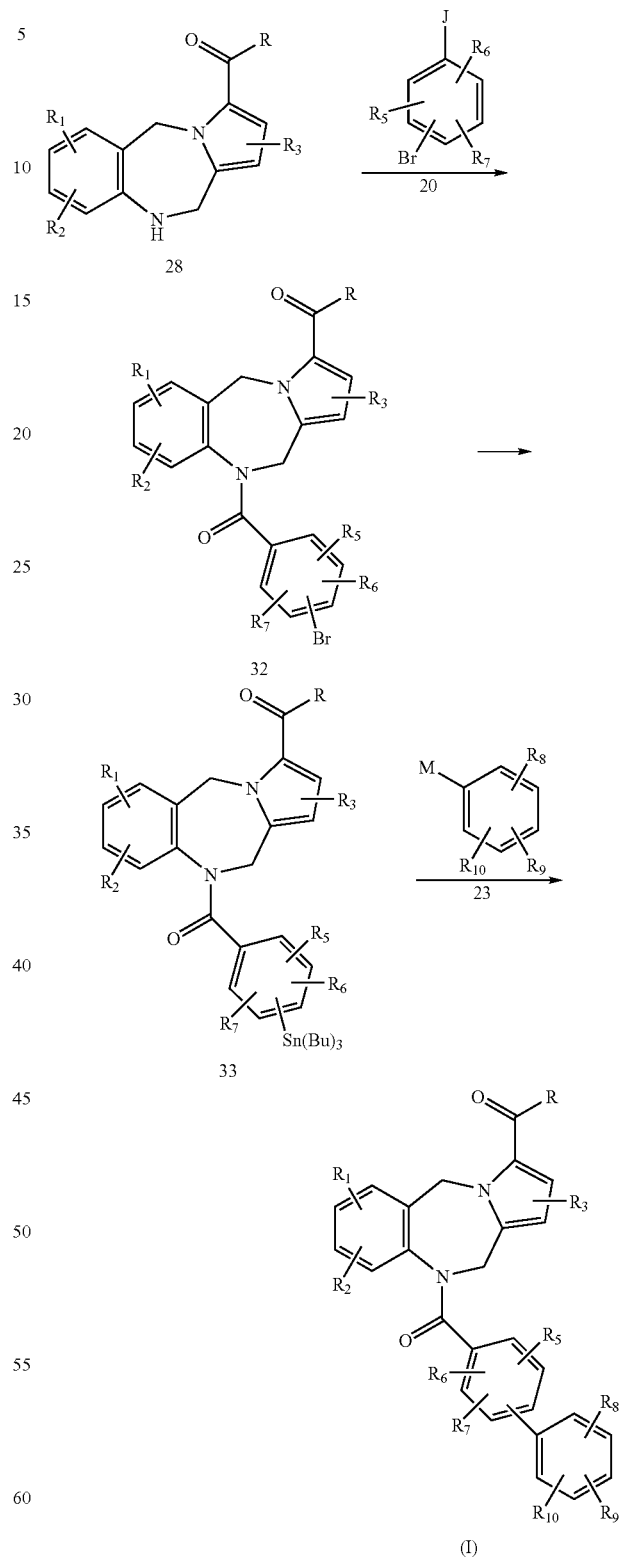

Alternatively, the compounds of formula (I) of Scheme I wherein B is (a), and $R_1$, $R_2$, $R_3$, $R_5$, $R_6$, $R_7$, $R_8$, $R_9$, and $R_{10}$ are defined hereinbefore, can be prepared as shown in Scheme XV by acylation of the amide intermediate (28) of Scheme XII with an acylating agent of formula (20) of Scheme IX.

Alternatively, the compounds of formula (I) of Scheme I wherein A is —C═O and B is (a) and $R_1$, $R_2$, $R_3$, $R_5$, $R_6$, $R_7$, $R_8$, $R_9$, and $R_{10}$ are defined hereinbefore, can be prepared by acylation of the amide intermediate (28) of Scheme XII with an acylating agent of formula (7) of Scheme V, wherein J is hereinbefore defined, as shown in Scheme XVI.

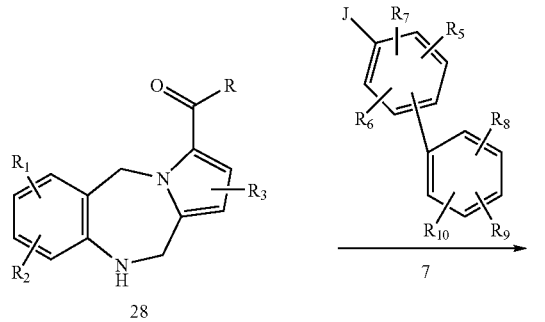

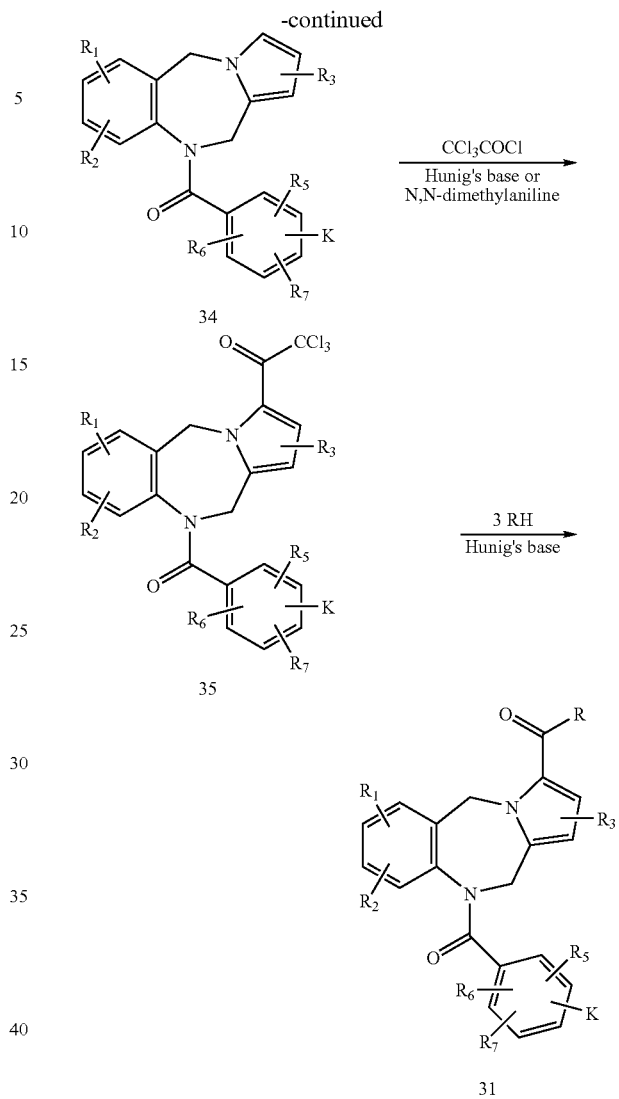

A process for the preparation of the amide intermediate (31) of Scheme XIV is shown in Scheme XVII. A tricyclic benzodiazepine of formula (6) is acylated with an acylating agent (17, K=Br or I) to provide the intermediate (34). This in turn is reacted with a perhaloalkanoyl halide such as trichloroacetyl chloride under the conditions of Scheme I to provide the trichloroacetyl intermediate of formula (35). Subsequent reaction of (35) with an appropriate primary or secondary amine also under the conditions of Scheme I provides the desired product (31).

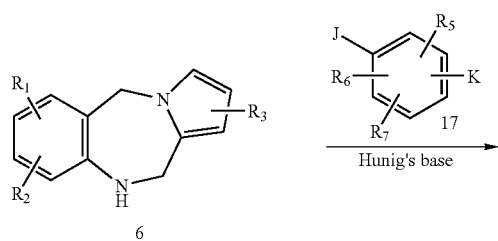

EXAMPLES

Compound Examples

The following examples are presented to illustrate rather than limit the scope of the present invention.

Example 1

2,2,2-TRICHLORO-1-{10-[(2'-METHOXY-1,1'-BIPHENYL-4-YL)CARBONYL]-10,11-DIHYDRO-5H-PYRROLO[2,1-C][1,4]BENZODIAZEPIN-3-YL}ETHANONE

Trichloroacetyl chloride (2.63 mL, 23.6 mmol) was added dropwise over five minutes to a solution of (2'-methoxy-1-1'-biphenyl-4-yl)-(5H,11H-pyrrolo[2,1-c][1,4]benzodiazepin-10-yl)-methanone (3.0 g, 7.60 mmol) and N,N-diisopropyl-ethyl amine (2.65 mL, 15.2 mmol) in dichloromethane (60 mL). The reaction was stirred under nitrogen at room temperature overnight and then quenched with water. The organic layer was extracted with 0.1N hydrochloric acid and water, dried over anhydrous magnesium sulfate, filtered and concentrated to a green oil. The oil was purified by flash chromatography over silica gel Merck-60 using a gradient of 0 to 5% ethyl acetate in dichloromethane to give the title compound (2.34 g) as a yellow foam. MS [(+)ESI, m/z]: 539 [M+H]$^+$ Anal. Calcd for $C_{28}H_{21}C_{13}N_2O_3$.0.2$C_4H_8O_2$: C, 62.05; H, 4.09; N, 5.03. Found: C, 62.28; H, 4.47; N, 4.86

Example 2

N-[2-(DIMETHYLAMINO)-2-PHENYLETHYL]-10-[(2'-METHOXY-1,1'-BIPHENYL-4-YL)CARBONYL]-10,11-DIHYDRO-5H-PYRROLO[2,1-C][1,4]BENZODIAZEPINE-3-CARBOXAMIDE

To a suspension of 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (1.21 g, 2.25 mmole) in acetonitrile (25 mL) was added a solution of (2-amino-1-phenylethyl) dimethylamine (0.250 g, 1.52 mmole) in acetonitrile (5 mL), followed by dimethylsulfoxide (5 equivalents) and triethylamine (2.2 equivalents). The mixture was stirred at 82° C. under nitrogen for 18 hours. The solvent was evaporated, and the residue diluted with dichloromethane. The solution was washed with brine, dried over anhydrous magnesium sulfate and evaporated. The residue was flash chromatographed over silica gel Merck-60 using a gradient of 30 to 80% ethyl acetate in dichloromethane to provide the title compound as a light brown amorphous solid (0.777 g). MS [(+)ESI, m/z]: 585.19 [M+H]$^+$ Anal. Calcd for $C_{37}H_{36}N_4O_3$.0.2 $C_4H_8O_2$: C, 75.38; H, 6.29; N, 9.30. Found: C, 75.42; H, 6.38; N, 9.04.

Example 3

N-(2-CHLORO-6-PHENOXYBENZYL)-10-[(2'-METHOXY-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared according to the procedure of Example 2 starting from 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (0.562 g, 1.04 mmole), 2-chloro-5-phenoxy benzylamine (0.203 g, 0.86 mmole), dimethylsulfoxide (5 equivalents), triethylamine (2.2 equivalents) and acetonitrile (3 mL). Purification was carried out by HPLC (75% acetonitrile-25% water, 0.1% trifluoracetic acid). Pooled fractions containing pure material were neutralized with ammonium hydroxide and extracted with dichloromethane after removal of the acetonitrile. The extracts were washed with water, dried over anhydrous magnesium sulfate and evaporated to provide 0.188 g of desired material as an amorphous solid.

MS [(+)ESI, m/z]: 654.1 [M+H]$^+$ Anal. Calcd for $C_{40}H_{32}CIN_3O_4$.0.6 $H_2O$: C, 72.25; H, 5.03; N, 6.32. Found: C, 72.26; H, 5.36; N, 6.08.

Example 4

N-[(1R)-2-HYDROXY-1-PHENYLETHYL]-10-[(2'-METHOXY-1,1'-BIPHENYL-4-YL)CARBONYL]-10,11-DIHYDRO-5H-PYRROLO[2,1-C][1,4]BENZODIAZEPINE-3-CARBOXAMIDE

A mixture of 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (0.517 g, 0.985 mmole) and (R)-(–)-2-amino-2-phenylethanol (0.276 g, 20 mmole), dimethylsulfoxide (2.8 mmole) and triethylamine (0.213 g, 2.1 mmole) in acetonitrile (10 mL) was heated at 80-85° C. for 22 hours. The residue left upon removal of the solvent was taken up in 15 mL of dichloromethane, washed with brine, dried over anhydrous magnesium sulfate and concentrated to give a tan solid. Purification by flash chromatography on silica gel Merck-60 using a gradient of 0 to 25% ethyl acetate in dichloromethane provided a light yellow solid (0.283 g). Recrystallization from ethyl acetate/hexane gave the title compound as off-white needles, m.p. 195-196° C. MS [(+)ESI, m/z]: 558.14 [M+H]$^+$ Example 5

N-[(1S)-2-HYDROXY-1-PHENYLETHYL]-10-[(2'-METHOXY-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared using the procedure of Example 4 using (S)-(+)-2-amino-2-phenylethanol (0.277 g, 2.0 mmole). Flash chromatography (gradient of 0-30% ethyl acetate in dichloromethane) provided a white solid (0.250 g). Recrystallization from ethyl acetate/hexane gave an off-white solid, m.p. 196-197° C. MS [(+)ESI, m/z]: 558.14 [M+H]$^+$ Example 6

2,2,2-TRICHLORO-1-{10-[(2,2'-DIMETHYL-1,1'-BIPHENYL-4-YL)CARBONYL]-10,11-DIHYDRO-5H-PYRROLO[2,1-C][1,4]BENZODIAZEPIN-3-YL}ETHANONE

Step A. Methyl 2,2'-dimethyl-1,1'-biphenyl-4-carboxylate

A mixture of methyl 4-bromo-3-methylbenzoate (25.0 g, 110 mmol), o-tolylboronic acid (16.5 g, 120 mmol) and potassium carbonate (50 g, 360 mmol) in dioxane/water (300 mL:200 mL) was purged with nitrogen for 1 hour. [1,-bis(Diphenylphosphino) ferrocene]dichloropalladium [II] (4.5 g, 5.5 mmol) was added. The reaction mixture was heated to 100° C. with vigorous stirring for 3.5 hours, then cooled and filtered through Celite® (Celite Corp., Santa Barbara, Calif.). The cake was washed with ethyl acetate (500 mL). The combined organic phases were washed with 1N sodium hydroxide (500 mL) and brine (500 mL), dried over anhydrous potassium carbonate, and concentrated in vacuo to afford a dark oil (28.6 g). Purification by flash chromatography using 2% ethyl acetate in hexanes as solvent provided the title compound (24.7 g, 93%) as a pale yellow oil. MS [(+)ESI, m/z]: 241 [M+H]$^+$ HRMS [(+)ESI, m/z]: 241.12205 [M+H]$^+$. Calcd for $C_{16}H_{17}O_2$: 241.12286 Anal. Calcd for $C_{16}H_{16}O_2$: C, 79.97; H, 6.71. Found: C, 79.67; H, 6.61.

Step B. 2,2'-Dimethyl-biphenyl-4-carboxylic acid

To a solution of methyl 2,2'-dimethyl-1,1'-biphenyl-4-carboxylate of Step A (24.7 g, 103 mmol) in tetrahydrofuran:methanol (5:1, 200 mL) was added 1N sodium hydroxide (108 mL, 108 mmol) and the reaction mixture was heated at reflux for 1 hour. The cooled reaction mixture was then concentrated in vacuo to remove organic solvents. The resulting aqueous solution was cooled to 0° C. and 2N hydrochloric acid (60 mL, 120 mmol) was added slowly followed by water (60 mL) to facilitate stirring of the precipitated product. The suspension was stirred for 1 hour at 0° C., then filtered to afford the title compound (22.6 g, 97%) as a white solid, m.p. 140-143° C. MS [(−)ESI, m/z]: 225 [M−H]⁻.

Step C. (10,11-Dihydro-5H-pyrrolo[2,1-c][1,4]benzodiazepin-10-yl)-(2,2'-dimethyl-biphenyl-4-yl)-methanone To a suspension of 2,2'-dimethyl-biphenyl-4-carboxylic acid of Step B (22.4 g, 99.0 mmol) in dry dichloromethane (500 mL) at room temperature under nitrogen was added dry N,N-dimethylformamide (5 mL) followed by the dropwise addition of a 2.0 M solution of oxalyl chloride in dichloromethane (60 mL, 120 mmol). The reaction mixture was stirred at room temperature for 2 hours, then concentrated in vacuo and the residue redissolved in dry dichloromethane (200 mL). The solution was concentrated in vacuo to afford the crude acid chloride as a brown oil. The acid chloride was dissolved in dichloromethane (500 mL), 10,11-dihydro-5H-pyrrolo[2,1-c][1,4]benzodiazepine (21.9 g, 119 mmol) was added, followed by N,N-diisopropylethylamine (87 mL, 500 mmol) and the reaction mixture was stirred at room temperature under nitrogen for 16 hours. The reaction mixture was then washed with 1N hydrochloric acid (5×1 L), 10% aqueous sodium hydroxide (1 L) and brine (500 mL), dried over anhydrous magnesium sulfate, filtered and concentrated in vacuo to give a dark foam. Purification by flash chromatography using a solvent gradient of 2.5 to 40% ethyl acetate in hexane gave a tan solid that was recrystallized from ethyl acetate/hexane to afford the title compound (12.4 g, 32%) as a pale orange solid. Purification of the mother liquors by flash chromatography yielded additional title compound (11.5 g, 30%) as a white solid, m.p. 145-148° C. MS [(+)ESI, m/z]: 393 [M+H]⁺.

Step D. 2,2,2-Trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone To a solution of (10,11-dihydro-5H-pyrrolo[2,1-c][1,4]benzodiazepin-10-yl)-(2,2'-dimethyl-biphenyl-4-yl)-methanone of Step C (12.4 g, 31.6 mmol) and N,N-dimethylaniline (6.4 mL, 50.5 mmol) in dry dichloromethane (90 mL) at 0° C. under nitrogen, was added trichloroacetyl chloride (5.3 mL, 47.5 mmol). The reaction was then allowed to warm slowly to room temperature while stirring overnight. The reaction mixture then was washed with 2N hydrochloric acid (2×100 mL), water (100 mL) and brine (100 mL), dried over anhydrous magnesium sulfate, filtered and concentrated in vacuo to give a dark foam. Purification by filtration through a plug of silica gel (60 g) eluting with dichloromethane afforded the title compound (15.9 g, 94%) as a light orange solid, m.p. 212-214° C. MS [(+)ESI, m/z]: 537 [M+H]⁺.

Anal. Calcd for $C_{29}H_{23}Cl_3N_2O_2$: C, 64.76; H, 4.31; N, 5.21. Found: C, 64.70; H, 4.35; N, 4.96.

Example 7

10-[(2,2'-DIMETHYL-1,1'-BIPHENYL-4-YL)CARBONYL]-N-(3-METHOXYBENZYL)-10,11-DIHYDRO-5H-PYRROLO[2,1-C][1,4]BENZODIAZEPINE-3-CARBOXAMIDE

To a suspension of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 (0.538 g, 1.0 mmol) and dimethyl sulfoxide (0.35 mL, 4.9 mmol, 5 eq.) in acetonitrile (6 mL) was added 3-methoxybenzylamine (0.26 mL, 2.0 mmol, 2 eq.) and the reaction mixture was heated to reflux for 45 hours. The cooled reaction mixture was then concentrated in vacuo to remove acetonitrile. The oily residue was dissolved in ethyl acetate (25 mL), washed with 1N sodium hydroxide (25 mL), water (25 mL) and brine (25 mL), dried over anhydrous magnesium sulfate, filtered and concentrated in vacuo to give the crude product (0.59 g) as a brown foam. Purification by flash chromatography using a solvent gradient of 20 to 40% ethyl acetate in hexane gave the title compound (330 mg, 59%) as a pale yellow solid. MS [(+)ESI, m/z]: 556 (M+H)⁺.HRMS [(+)ESI, m/z]: 556.25884 [M+H]⁺. Calcd for $C_{36}H_{34}N_3O_3$: 556.26002. Anal. Calcd for $C_{36}H_{33}N_3O_3$: C, 77.81; H, 5.99; N 7.56. Found: C, 77.50; H, 6.10; N 7.43.

Example 8

10-[(2,2'-DIMETHYL-1,1'-BIPHENYL-4-YL)CARBONYL]-N-(4-METHOXYBENZYL)-10,11-DIHYDRO-5H-PYRROLO[2,1-C][1,4]BENZODIAZEPINE-3-CARBOXAMIDE

Prepared in the manner of Example 7, replacing 3-methoxybenzylamine with 4-methoxybenzylamine. Recrystallization from diethyl ether/hexane provided the title compound as pale yellow needles (0.269 g, 48%), m.p. 127-128° C. MS [(−)ESI, m/z]: 554 [M−H]⁻. Anal. Calcd for $C_{36}H_{33}N_3O_3$: C, 77.81; H, 5.99; N, 7.56. Found: C, 77.65; H, 6.37; N, 7.25.

Example 9

10-[(2,2'-DIMETHYL-1,1'-BIPHENYL-4-YL)CARBONYL]-N-(4-HYDROXYBENZYL)-10,11-DIHYDRO-5H-PYRROLO[2,1-C][1,4]BENZODIAZEPINE-3-CARBOXAMIDE

To a solution of 10-[(2,2'-dimethyl-1,1'-biphenyl-4-yl)carbonyl]-N-(4-methoxybenzyl)-10,11-dihydro-5H-pyrrolo[2,1-c][1,4]benzodiazepine-3-carboxamide of Example 8 (243 mg, 0.437 mmol) in dichloromethane (1.5 mL) at 0° C. under nitrogen was added a solution of boron tribromide in dichloromethane (1.0 M, 1.5 mL, 1.5 mmol) dropwise over 5 minutes. After 10 minutes at 0° C. the cooling bath was removed and the solution allowed to warm slowly to room temperature over 1.5 hours. The reaction was quenched by the addition of saturated aqueous sodium hydrogen carbonate solution (20 mL) and extracted with ethyl acetate (3×20 mL). The combined organic extracts were washed with a saturated aqueous sodium hydrogen carbonate solution (20 mL) and brine (20 mL), dried over anhydrous magnesium sulfate, filtered and concentrated in vacuo to give a reddish oil (305 mg). Purification by flash chromatography using a solvent gradient of 0 to 2% methanol in dichloromethane gave the title compound (119 mg, 52%) as a white solid. MS [(+)ESI, m/z]: 542 [M+H]⁺.HRMS [(+)ESI, m/z]: 542.24405. Calcd for $C_{35}H_{32}N_3O_3$: 542.24437. Anal. Calcd for $C_{35}H_{31}N_3O_3$: C, 77.61; H, 5.77; N, 7.76. Found: C, 77.54; H, 5.79; N, 7.72.

Example 10

10-[(2,2'-DIMETHYL-1,1'-BIPHENYL-4-YL)CARBONYL]-N-(3-HYDROXYBENZYL)-10,11-DIHYDRO-5H-PYRROLO[2,1-C][1,4]BENZODIAZEPINE-3-CARBOXAMIDE

Prepared in the manner of Example 9 by replacing 10-[(2,2'-dimethyl-1,1'-biphenyl-4-yl)carbonyl]-N-(4-methoxybenzyl)-10,11-dihydro-5H-pyrrolo[2,1-c][1,4]benzodiazepine-3-carboxamide of Example 8 with 10-[(2,2'-dimethyl-1,1'-biphenyl4-yl)carbonyl]-N-(3-methoxybenzyl)-10,11- dihydro-5H-pyrrolo[2,1-c][1,4]benzodiazepine-3-carboxamide of Example 7. Purification by trituration with dichloromethane gave the title compound (0.168 g, 66%) as a white solid.

HRMS [(+)ESI, m/z]: 542.24351. Calcd for $C_{35}H_{32}N_3O_3$: 542.24437.

Example 11

N-[4-(AMINOMETHYL)BENZYL]-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

Prepared in the manner as Example 7 by replacing 3-methoxybenzylamine with p-xylenediamine. Purification by flash chromatography using a solvent gradient of 1 to 4% ammonia saturated methanol in dichloromethane gave the title compound (0.210 g, 38%) as a white solid. MS [(+)ESI, m/z]: 555 [M+H]$^+$. HRMS [(+)ESI, m/z]: 555.27582. Calcd for $C_{36}H_{35}N_4O_2$: 555.27600.

Example 12

N-[3-(AMINOMETHYL)BENZYL]-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

Prepared in the manner of Example 7 by replacing 3-methoxybenzylamine with m-xylenediamine. Purification by flash chromatography using a solvent gradient from 1 to 4% ammonia saturated methanol in dichloromethane gave the title compound (0.320 g, 58%) as a white foam. MS [(+)ESI, m/z]: 555 [M+H]$^+$. HRMS [(+)ESI, m/z]: 555.27495. Calcd for $C_{36}H_{35}N_4O_2$: 555.27600.

Example 13

10-[(2,2'-DIMETHYL-1,1'-BIPHENYL-4-YL)CARBONYL]-N-(1-PHENYLETHYL)-10,11-DIHYDRO-5H-PYRROLO[2,1-C][1,4]BENZODIAZEPINE-3-CARBOXAMIDE

A solution of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 (2 mmol), α-methylbenzylamine (4.2 mmol) in dimethylsulfoxide (7 mmol) and acetonitrile (15 mL) was stirred at 80° C. for 18 hours. The solvents were evaporated and the residue was dissolved in dichloromethane, washed with water, dried over anhydrous sodium sulfate and evaporated. The compound was purified by HPLC (normal phase, Luna® CN bonded packing (Phenomenex, Torrance, Calif.)) and crystallized from ethyl acetate/hexane. (0.93 g), m.p. 118-124°C. MS [(+)ESI, m/z]: 538 [M+H]$^+$Anal. Calcd for $C_{36}H_{33}N_2O_2$: C, 80.12; H, 6.16; N, 7.79. Found: C, 79.97; H, 6.27; N, 7.78.

Example 14

10-[(2,2'-DIMETHYL-1,1'-BIPHENYL-4-YL)CARBONYL]-N-(4-METHYLBENZYL)-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-methylbenzylamine, m.p. 179-181° C. MS [(+)ESI, m/z]: 538 [M+H]$^+$Anal. Calcd for $C_{36}H_{33}N_3O_2$: C, 80.12; H, 6.16; N, 7.79. Found: C, 79.87; H, 5.95; N, 7.71.

Example 15

N-BENZYL-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and benzylamine, m.p. 138-141° C. MS [(+)ESI, m/z]: 524 [M+H]$^+$

Example 16

10-[(2,2'-DIMETHYL-1,1'-BIPHENYL-4-YL)CARBONYL]-N-[3-(TRIFLUOROMETHYL)BENZYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3-trifluoromethylbenzylamine, m.p. 171-173° C. MS [(+)ESI, m/z]: 592 [M+H]$^+$ Anal. Calcd for $C_{36}H_{30}F_3N_3O_2$: C, 72.84; H, 5.09; N, 7.08. Found: C, 72.73; H, 5.10; N, 7.03.

EXAMPLE 17

10-[(2,2'-DIMETHYL-1,1'-BIPHENYL-4-YL)CARBONYL]-N-(2-METHYLBENZYL)-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 2-methylbenzylamine, m.p. 128-130° C. MS [(+)ESI, m/z]: 538 [M+H]$^+$ Anal. Calcd for $C_{36}H_{33}N_3O_2$: C, 80.12; H, 6.16; N, 7.79. Found: C, 79.70; H, 6.40; N, 7.57.

Example 18

N-(4-CHLOROBENZYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-chlorobenzylamine, m.p. 196-197° C. MS [(+)ESI, m/z]: 558 [M+H]$^+$ Anal. Calcd for $C_{35}H_{30}ClN_3O_2$: C, 75.06; H, 5.40; N, 7.50. Found: C, 74.76; H, 5.43; N, 7.44.

Example 19

10-[(2,2'-DIMETHYL-1,1'-BIPHENYL-4-YL)CARBONYL]-N-[4-(TRIFLUOROMETHOXY)BENZYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-trifluoromethoxy benzylamine, m.p. 147-149° C. MS [(+)ESI, m/z]: 608 [M+H]$^+$ Anal. Calcd for $C_{36}H_{30}F_3N_3O_3$: C, 70.94; H, 4.96; N, 6.89. Found: C, 70.75; H, 5.13; N, 6.74.

Example 20

N-(3,5-DIMETHOXYBENZYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3,5-dimethoxybenzylamine, m.p. 183-184° C. MS [(+)ESI, m/z]: 584 [M+H]$^+$

Example 21

N-(2,4-DIMETHYLBENZYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 2,4-dimethylbenzylamine, m.p. 159-161° C. MS [(+)ESI, m/z]: 552 [M+H]$^+$ Anal. Calcd for $C_{37}H_{35}N_3O_2$: C, 80.26; H, 6.37; N, 7.59. Found: C, 79.84; H, 6.12; N, 7.41.

Example 22

10-[(2,2'-DIMETHYL-1,1'-BIPHENYL-4-YL)CARBONYL]-N-(3-METHYLBENZYL)-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3-methylbenzylamine, m.p. 130-132° C. MS [(+)ESI, m/z]: 538 [M+H]$^+$ Anal. Calcd for $C_{36}H_{33}N_3O_2$: C, 80.12; H, 6.16; N, 7.79. Found: C, 80.01; H, 6.33; N, 7.61.

Example 23

N-(1,3-BENZODIOXOL-5-YLMETHYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and piperonylamine, m.p. 149-151° C. MS [(+)ESI, m/z]: 568 [M+H]$^+$ Anal. Calcd for $C_{36}H_{31}N_3O_4$: C, 75.90; H, 5.49; N, 7.38. Found: C, 75.77; H, 5.36; N, 7.19.

Example 24

10-[(2,2'-DIMETHYL-1,1'-BIPHENYL-4-YL)CARBONYL]-N-[2-(TRIFLUOROMETHYL)BENZYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 2-trifluoromethoxybenzylamine, m.p. 126-128°C. MS [(+)ESI, m/z]: 592 [M+H]$^+$ Anal. Calcd for $C_{36}H_{30}F_3N_3O_2$: C, 72.84; H, 5.09; N, 7.08. Found: C, 72.59; H, 5.23; N, 6.99.

Example 25

10-[(2,2'-DIMETHYL-1,1'-BIPHENYL-4-YL)CARBONYL]-N-(3-PHENYLPROPYL)-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3-phenyl-1-propylamine, m.p. 183-184° C. MS [(+)ESI, m/z]: 554 [M+H]$^+$ Anal. Calcd for $C_{37}H_{35}N_3O_2$: C, 80.26; H, 6.37; N, 7.59. Found: C, 80.18; H, 6.37; N, 7.51.

Example 26

N-[2-(3-CHLOROPHENYL)ETHYL]-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3-chlorophenethylamine, m.p. 174-176°C. MS [(+)ESI, m/z]: 574 [M+H]$^+$ Anal. Calcd for $C_{36}H_{32}ClN_3O_2$: C, 75.31; H, 5.62; N, 7.32. Found: C, 75.19; H, 5.55; N, 7.22.

Example 27

N-[2-(4-CHLOROPHENYL)ETHYL]-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-chlorophenethylamine, m.p. 169-171° C. MS [(+)ESI, m/z]: 574 [M+H]$^+$ Anal. Calcd for $C_{36}H_{32}ClN_3O_2$: C, 75.31; H, 5.62; N, 7.32. Found: C, 75.32; H, 5.48; N, 7.23.

Example 28

N-[2-(3,4-DIMETHOXYPHENYL)ETHYL]-10-[(2, 2'-DIMETHYL-1,1'-BIPHENYL-4-YL)CARBONYL]-10,11- DIHYDRO-5H-PYRROLO[2,1-C][1, 4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 3,4-dimethoxyphenethylamine, m.p. 130-136° C. MS [(+)ESI, m/z]: 600 [M+H]$^+$

Example 29

10-[(2,2'-DIMETHYL-1,1'-BIPHENYL-4-YL)CARBONYL]-N-[2-(4-METHYLPHENYL)ETHYL]-10, 11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-methylphenethylamine, m.p. 161-163° C. MS [(+)ESI, m/z]: 554 [M+H]$^+$

Example 30

10-[(2,2'-DIMETHYL-1,1'-BIPHENYL-4-YL)CARBONYL]-N-[2-(4-METHOXYPHENYL)ETHYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 4-methoxyphenethylamine, m.p. 170-172° C. MS [(+)ESI, m/z]: 570 [M+H]$^+$ Anal. Calcd for $C_{37}H_{35}N_3O_3$: C, 78.01; H, 6.19; N, 7.38. Found: C, 77.93; H, 6.15; N, 7.30.

Example 31

10-[(2,2'-DIMETHYL-1,1'-BIPHENYL-4-YL)CARBONYL]-N-[2-(4-HYDROXYPHENYL)ETHYL]-10,11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and tyramine, m.p. 129-131° C. MS [(+)ESI, m/z]: 554 [M+H]$^+$

Example 32

10-[(2,2'-DIMETHYL-1,1'-BIPHENYL-4-YL)CARBONYL]-N-(1-METHYL-3-PHENYLPROPYL)-10, 11-DIHYDRO-5H-PYRROLO[2,1-C][1,4]BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 and 1-methyl-3-phenylpropylamine, m.p. 152-154° C. MS [(+)ESI, m/z]: 566 [M+H]$^+$ Anal. Calcd for $C_{36}H_{37}N_3O_2$: C, 80.39; H, 6.57; N, 7.40. Found: C, 80.27; H, 6.70; N, 7.27.

Example 33

N-[2-(1,3-BENZODIOXOL-5-YL)ETHYL]-10-[(2, 2'-DIMETHYL-1,1'-BIPHENYL-4-YL)CARBONYL]-10,11-DIHYDRO-5H-PYRROLO[2,1-C][1,4] BENZODIAZEPINE-3-CARBOXAMIDE

The title compound was synthesized in the manner of Example 13 from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6, 3,4-methylenedioxyphenethylamine hydrochloride and triethylamine (2.2 eq.), m.p. 154-157° C. MS [(+)ESI, m/z]: 582 [M+H]$^+$

Example 34

N-(3-AMINOBENZYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

A solution of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 6 (0.125 g; 0.275 mmol), and 3-aminobenzylamine (0.071 g; 0.577 mmol), in dimethylsulfoxide (5 mL) was stirred at 80° C. for 18 hours. The solution was diluted with water and extracted into dichloromethane. The extracts were dried over anhydrous sodium sulfate and evaporated to yield the title compound as an amorphous white solid (0.085 g; 57%), m.p. 105-115° C. MS [(+)ESI, m/z]: 541.2 [M+H]$^+$

Example 35

2,2,2-TRICHLORO-1-{10-[(2-METHOXY-2'-METHYL-1,1'-BIPHENYL-4-YL)CARBONYL]-10,11-DIHYDRO-5H-PYRROLO[2,1-C][1,4]BENZODIAZEPIN-3-YL}ETHANONE

Step A. Methyl 4-bromo-3-hydroxybenzoate

To a solution of 4-bromo-3-hydroxybenzoic acid (30 mmol) in methanol (100 mL) was added concentrated sulfuric acid (2.6 mL). The solution was heated at reflux for 5 hours, cooled to 0° C., and then brought to pH 7 by adding saturated aqueous sodium carbonate. The solution was evaporated to one-third the original volume. Water was added and the product was extracted into ethyl acetate. The organic extracts were washed with water and brine and dried over anhydrous sodium sulfate. Evaporation gave 6.15 g (89%) of the product as a white solid, m.p. 130-132° C.

Step B. Methyl 4-bromo-3-methoxybenzoate

A solution of methyl 4-bromo-3-hydroxybenzoate of Step A (27 mmol), potassium carbonate (33 mmol), and dimethyl sulfate (32 mmol) in acetone (40 mL) was stirred at reflux temperature under nitrogen atmosphere for three hours. The mixture was cooled and 5 mL of water was added. The acetone was evaporated and 30 mL of water was added. The product was extracted into dichloromethane. The organic solution was dried over anhydrous magnesium sulfate, filtered and evaporated to give the title compound (6.5 g, 99%) as a hard, white crystalline solid.

Step C. 2-Methoxy-2'-methyl-biphenyl-4-carboxylic acid methyl ester

A solution consisting of toluene (100 mL), ethanol (50 mL), and water (50 mL) was sparged with dry nitrogen for 45 minutes. To the mixture was added methyl 4-bromo-3-methoxybenzoate of step B (26.5 mmol), o-tolylboronic acid (29.1 mmol), and sodium carbonate (112.5 mmol). The mixture was sparged with nitrogen for an additional ten minutes. Terakis(triphenylphosphine)palladium(0) (1 mmol) was added to the mixture, which was then heated at 105° C. for 6 hours. The mixture was cooled and the organic phase was washed three times in sequence with saturated aqueous sodium carbonate and brine. The organics were dried over anhydrous sodium sulfate, filtered, and evaporated to an oil. Flash chromatography of the residue on silica gel using dichloromethane/hexane (3:1) yielded the title compound as a clear oil (6.7 g, 99%).

Step D. 2-Methoxy-2'-methyl-biphenyl-4-carboxylic acid

To the 2-methoxy-2'-methyl-biphenyl-4-carboxylic acid methyl ester of step C (26 mmol) was added methanol (10 mL), tetrahydrofuran (45 mL) and 1 N sodium hydroxide (33 mL). The solution was refluxed vigorously in an oil bath at 105° C. for one hour. The volatile solvents were evaporated and the solution was chilled in ice. 2N hydrochloric acid was added until the pH was ~1. The product was extracted into ethyl acetate, dried with anhydrous magnesium sulfate, and evaporated to a white solid. This was recrystallized from ethyl acetate/hexane to afford 5.5 g of title compound (86%).

Step E. 10-[(2-Methoxy-2'-methyl-1,1'-biphenyl-4-yl)carbonyl]-10,11-dihydro-5H-pyrrolo[2,1-c][1,4]benzodiazepine To a solution of 2-methoxy-2'-methyl-biphenyl-4-carboxylic acid of step D (23 mmol) in dichloromethane (50 mL) was added a drop of N,N-dimethylformamide. Oxalyl chloride (36 mmol) then was added dropwise to the solution, which then was stirred at reflux temperature for 2 hours. The solvents were evaporated and the resulting acid chloride was dissolved in 20 mL dichloromethane. This was added dropwise to a stirred mixture of 10,11-dihydro-5H-pyrrolo[2,1-c][1,4]benzodiazepine (25 mmol) and triethylamine (34 mmol) in dichloromethane (30 mL) at 0° C. under nitrogen atmosphere. After 20 hours the mixture was quenched with water and washed with 0.5 N hydrochloric acid, 1.0 N sodium hydroxide, and brine. The solution was dried over anhydrous sodium sulfate, and evaporated to a solid. The product was purified by flash chromatography using ethyl acetate/hexane (1:3) to yield 8.77 g (95%) of the title compound as a white solid.

Step F. 2,2,2-Trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone A solution of 10-[(2-methoxy-2'-methyl-1,1'-biphenyl-4-yl)carbonyl]-10,11-dihydro-5H-pyrrolo[2,1-c][1,4]benzodiazepine of Step E (21 mmol) and triethylamine (43 mmol) in anhydrous dichloromethane (45 mL) was cooled in an ice bath. To the stirred solution was added, dropwise, trichloroacetyl chloride (65 mmol). The mixture was allowed to stir at ambient temperature for 72 hours, then was washed with 0.1 N hydrochloric acid and brine, and dried over anhydrous sodium sulfate. Evaporation yielded a foam that solidified by heating with ethyl acetate and chloroform to provide 10.2 g (85%) of the title compound as a white solid, m.p. 221-222° C. MS [(+)ESI, m/z]: 553 [M+H]$^+$

Example 36

N-(4-METHOXYBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

In a glass tube was weighed 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 (0.32 mmol), acetonitrile (2.5 mL), 4-methoxybenzylamine (0.66 mmol), and dimethylsulfoxide (1.11 mmol). The stirred solution was heated at 80° C. for 20 hours. The solvent was evaporated and the residue was dissolved in dichloromethane (5 mL), washed twice with water, dried over anhydrous sodium sulfate, and evaporated. Flash chromatography on silica gel using hexane/ethyl acetate/dichloromethane (3:1:1) provided 0.155 g (86%) of the title compound as a white solid, which was recrystallized from ethyl acetate/hexane, m.p. 178-179° C. MS [(+)ESI, m/z]: 570 [M+H]$^+$Anal. Calcd for $C_{36}H_{33}N_3O_4$: C, 75.64; H, 5.82; N, 7.35. Found: C, 75.31; H, 5.83; N, 7.27.

Example 37

10-[(2-METHOXY-2'-METHYL-1,1'-BIPHENYL-4-YL)CARBONYL]-N-(3-METHYLBENZYL)-10,11-DIHYDRO-5H-PYRROLO[2,1-C][1,4]BENZODIAZEPINE-3-CARBOXAMIDE

The title compound was prepared in 78% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 3-methyl benzylamine, m.p. 165-166° C. MS [(+)ESI, m/z]: 556 [M+H]$^+$ Anal. Calcd for $C_{36}H_{33}N_3O_3$: C, 77.81; H, 5.99; N, 7.56. Found: C, 77.72; H, 5.96; N, 7.54.

Example 38

10-[(2-METHOXY-2'-METHYL-1,1'-BIPHENYL-4-YL)CARBONYL]-N-(4-METHYLBENZYL)-10,11-DIHYDRO-5H-PYRROLO[2,1-C][1,4]BENZODIAZEPINE-3-CARBOXAMIDE

The title compound was prepared in 84% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-methylbenzylamine, m.p. 179-180° C. MS [(+)ESI, m/z]: 556 [M+H]$^+$ Anal. Calcd for $C_{36}H_{33}N_3O_3$: C, 77.81; H, 5.99; N, 7.56. Found: C, 77.57; H, 6.01; N, 7.50.

Example 39

10-[(2-METHOXY-2'-METHYL-1,1'-BIPHENYL-4-YL)CARBONYL]-N-[2-(TRIFLUOROMETHYL)BENZYL]-10,11-DIHYDRO-5H-PYRROLO[2,1-C][1,4]BENZODIAZEPINE-3-CARBOXAMIDE

The title compound was prepared in 75% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-trifluoromethylbenzylamine, m.p. 165-167° C. MS [(+)ESI, m/z]: 610 [M+H]$^+$ Anal. Calcd for $C_{36}H_{30}F_3N_3O_3$: C, 70.93; H, 4.96; N, 6.89. Found: C, 70.70; H, 4.89; N, 6.81.

Example 40

N-(1,3-BENZODIOXOL-5-YLMETHYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in 68% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and C-benzo[1,3]dioxol-5-yl-methylamine, m.p. 167-168° C. MS [(+)ESI, m/z]: 586 [M+H]$^+$ Anal. Calcd for $C_{36}H_{31}N_3O_5$: C, 73.83; H, 5.34; N, 7.17. Found: C, 73.41; H, 5.43; N, 7.12.

Example 41

10-[(2-METHOXY-2'-METHYL-1,1'-BIPHENYL-4-YL)CARBONYL]-N-(2-METHYLBENZYL)-10,11-DIHYDRO-5H-PYRROLO[2,1-C][1,4]BENZODIAZEPINE-3-CARBOXAMIDE

The title compound was prepared in 68% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-methylbenzylamine, m.p. 204° C. MS [(+)ESI), m/z]: 556 [M+H]$^+$ Anal. Calcd for $C_{36}H_{33}N_3O_3$: C, 77.81; H, 5.99; N, 7.56. Found: C, 77.73; H, 5.95; N, 7.55.

Example 42

10-[(2-METHOXY-2'-METHYL-1,1'-BIPHENYL-4-YL)CARBONYL]-N-[3-(TRIFLUOROMETHYL)BENZYL]-10,11-DIHYDRO-5H-PYRROLO[2,1-C][1,4]BENZODIAZEPINE-3-CARBOXAMIDE

The title compound was prepared in 79% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 3-trifluoromethylbenzylamine, m.p. 176-177° C. MS [(+)ESI, m/z]: 610 [M+H]$^+$ Anal. Calcd for $C_{36}H_{30}F_3N_3O_3$: C, 70.93; H, 4.96; N, 6.89. Found: C, 70.89; H, 5.02; N, 6.80.

Example 43

N-(4-CHLOROBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in 86% yield in the manner of Example 36 from 2,2,2-trichloro-1-{10-[(2-methoxy-2'-methyl-1,1'-biphenyl4-yl)carbonyl]-10,11-dihydro-5H-pyrrolo[2,1-c][1,4]benzodiazepin-3-yl}ethanone of Example 35 and 4-chlorobenzylamine, m.p. 218-219° C. MS (+)ESI, m/z]: 576 [M+H]$^+$ Anal. Calcd for $C_{35}H_{30}ClN_3O_3$: C, 72.97; H, 5.25; N, 7.29. Found: C, 72.67; H, 5.34; N, 7.11.

Example 44

N-BENZYL-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in 78% yield in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and benzylamine, m.p. m.p. 170-174° C. MS [(+)ESI, m/z]: 542 [M+H]$^+$ Anal. Calcd for $C_{35}H_{31}N_3O_3$: C, 77.61; H, 5.77; N, 7.76. Found: C, 77.51; H, 5.74; N, 7.58.

Example 45

10-[(2-METHOXY-2'-METHYL-1,1'-BIPHENYL-4-YL)CARBONYL]-N-[4-(TRIFLUOROMETHOXY)BENZYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-trifluoromethoxybenzylamine, m.p. 145-149° C. MS [(+)ESI, m/z]: 626 [M+H]$^+$ Anal. Calcd for $C_{36}H_{30}F_3N_3O_4$: C, 69.11; H, 4.83; N, 6.72. Found: C, 69.08; H, 4.95; N, 6.53.

Example 46

N-(2,4-DIMETHYLBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2,4-dimethyl benzylamine, m.p. 161-162° C. MS [(+)ESI, m/z]: 570 [M+H]$^+$ Anal. Calcd for $C_{37}H_{35}N_3O_3$: C, 78.01; H, 6.19; N, 7.38. Found: C, 77.86; H, 6.40; N, 7.20.

Example 47

10-[(2-METHOXY-2'-METHYL-1,1'-BIPHENYL-4-YL)CARBONYL]-N-[2-(4-METHOXYPHENYL)ETHYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2,4-dimethyl benzylamine. Purification was performed using HPLC with a normal phase column. Elution with a mixture of ethoxynonafluorobutane and methanol gave the title compound in 87% yield, m.p. 193-195° C. MS [(+)ESI, m/z]: 586 [M+H]$^+$

Example 48

10-[(2-METHOXY-2'-METHYL-1,1'-BIPHENYL-4-YL)CARBONYL]-N-[2-(4-METHYLPHENYL)ETHYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-(p-tolyl)-ethylamine. Purification was performed using HPLC with a normal phase column. Elution with a mixture of etoxynonafluorobutane and methanol gave the title compound, m.p. 190-192° C. MS [(+)ESI, m/z]: 570 [M+H]$^+$

Example 49

10-[(2-METHOXY-2'-METHYL-1,1'-BIPHENYL-4-YL)CARBONYL]-N-(4-PHENYLBUTYL)-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-phenylbutylamine. Purification was performed using HPLC with a normal phase column. Elution with a mixture of etoxynonafluorobutane and methanol gave the title compound (61% yield) as a yellow powder, m.p. 154-159° C. MS [(+)ESI, m/z]: 584 [M+H]$^+$

Example 50

N-(2,2-DIPHENYLETHYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2,2-diphenylethylamine. Purification was performed using HPLC with a normal phase column. Elution with a mixture of etoxynonafluorobutane and methanol gave the title compound (61% yield) as a yellow powder, m.p. 129-132° C. MS [(+)ESI, m/z]: 632 [M+H]$^+$

Example 51

N-[2-(3-CHLOROPHENYLETHYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-(3-chloro-phenyl)-ethylamine. Purification was performed using HPLC with a normal phase column. Elution with a mixture of etoxynonafluorobutane and methanol gave the title compound in 74% yield, m.p. 159-160° C. MS [(+)ESI, m/z]: 588 [M+H]$^+$

Example 52

N-[2-(3,4-DIMETHOXYPHENYL)ETHYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl4-yl)carbonyl]-10,11-dihydro-5H-pyrrolo[2,1-c][1,4]benzodiazepin-3-yl}ethanone of Example 35 and 2-(3,4-dimethoxyphenyl)-ethylamine. Purification was performed using HPLC with a normal phase column. Elution with a mixture of etoxynonafluorobutane and methanol gave the title compound in 97% yield, m.p. 150-154° C. MS [(+)ESI,m/z]: 616.26 [M+H]$^+$

Example 53

N-[2-(4-CHLOROPHENYL)ETHYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-(4-chlorophenyl)-ethylamine. Purification was performed using HPLC with a normal phase column. Elution with a mixture of etoxynonafluorobutane and methanol gave the title compound in 61% yield, m.p. 195-196° C. MS [(+)ESI, m/z]: 590.20 [M+H]$^+$

Example 54

10-[(2-METHOXY-2'-METHYL-1,1'-BIPHENYL-4-YL)CARBONYL]-N-(3-PHENYLPROPYL)-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 3-phenylpropylamine. Purification was performed using HPLC with a normal phase column. Elution with a mixture of etoxynonafluorobutane and methanol gave the title compound in 87% yield, m.p. 191° C. MS [(+)ESI, m/z]: 570 [M+H]$^+$

Example 55

N-[2-(4-HYDROXYPHENYL)ETHYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-(2-aminoethyl)-phenol. Purification was performed using HPLC with a normal phase column. Elution with a mixture of etoxynonafluorobutane and methanol gave the title compound in 90% yield, m.p. 190-194° C. MS [(+)ESI, m/z]: 572 [M+H]$^+$

Example 56

10-[(2,2'-DIMETHYL-1,1'-BIPHENYL-4-YL)CARBONYL]-N-(4-PHENYLBUTYL)-10,11-DIHYDRO-5H-PYRROLO[2,1-C][1,4]-BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-phenylbutylamine, m.p. 129-131° C. MS [(+)ESI, m/z]: 568 [M+H]$^+$ Anal. Calcd for $C_{38}H_{37}N_3O_2$: C, 80.39; H, 6.57; N, 7.40. Found: C, 80.18; H, 6.66; N, 7.34.

Example 57

N-[4-(DIMETHYLAMINO)BENZYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and (4-aminomethylphenyl)-dimethylamine dihydrochloride in the presence of two equivalents of triethylamine. Purification was performed using HPLC with a normal phase column. Elution with a mixture of etoxynonafluorobutane and methanol gave the title compound in 37% yield, m.p. 148-150° C. MS [(+)ESI, m/z]: 585 [M+H]$^+$

Example 58

10-[(2-METHOXY-2'-METHYL-1,1'-BIPHENYL-4-YL)CARBONYL]-N-(1-PHENYLETHYL)-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and (±)-1-phenylethylamine. Purification was performed using HPLC with a normal phase column by eluting with a two phase solvent system (A=hexane, B=dichloromethane/methanol, 4:1) that gave the title compound in 63% yield, m.p. 211° C. MS [(+)ESI, m/z]: 554 [M+H]$^+$ Anal. Calcd for $C_{36}H_{33}N_3O_3$: C, 77.81; H, 5.99; N, 7.56. Found: C, 77.65; H, 6.01; N, 7.45.

Example 59

N-(3,3-DIPHENYLPROPYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 3,3-diphenylpropylamine. Purification was performed using HPLC with a normal phase column by eluting with a two phase solvent system (A=hexane, B=dichloromethane/methanol, 4:1), m.p. 214° C.; MS [(+)ESI, m/z]: 644 [M+H]$^+$

Example 60

N-(4-FLUOROBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 4-fluorobenzylamine. Purification was performed using HPLC with a normal phase column. Elution with a two phase solvent system (A=hexane, B=dichloromethane/methanol, 4:1) gave the title compound in 80% yield, m.p. 214-215° C.; MS [(+)ESI, m/z]: 558 [M+H]$^+$

Example 61

N-(2,4-DILUOROBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2,4-difluorobenzylamine. Purification was performed using HPLC with a normal phase column. Elution with a two phase solvent system (A=hexane, B=dichloromethane/methanol, 4:1) gave the title compound in 69% yield, m.p. 196-197° C.; MS [(+)ESI, m/z]: 576 [M+H]$^+$ Anal. Calcd for $C_{35}H_{29}F_2N_3O_3$: C, 72.78; H, 5.06; N, 7.27. Found: C, 72.65; H, 5.04; N, 7.14.

Example 62

N-[2-(1,3-BENZODIOXOL-5-YL)ETHYL]-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and 2-benzo[1,3]dioxol-5-yl-ethylamine. Purification was performed using HPLC with a normal phase column. Elution with a two phase solvent system (A=hexane, B=dichloromethane/methanol, 4:1) gave the title compound in 75% yield, m.p. 178-179° C.; MS [(+)ESI, m/z]: 600 [M+H]$^+$

Example 63

N-(2-HYDROXY-2-PHENYLETHYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and (±)-2-amino-1-phenylethanol. Purification was performed using HPLC with a normal phase column. Elution with a two phase solvent system (A=hexane, B=dichloromethane/methanol, 4:1) gave the title compound in 77% yield, m.p. 214-215° C. MS [(+)ESI, m/z]: 572 [M+H]$^+$

Example 64

N-(2,3-DIHYDRO-1,4-BENZODIOXIN-6-YLMETHYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and C-(2,3-dihydrobenzo[1,4]dioxin-6-yl)-methylamine. Purification was performed using HPLC with a normal phase column and eluting with a two phase solvent system (A=hexane, B=dichloromethane/methanol, 4:1), m.p. 153-155° C. MS [(+)ESI, m/z]: 600 [M+H]$^+$

Example 65

N-(2,3-DIHYDRO-1H-INDEN-2-YL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared in the manner of Example 36 from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Example 35 and indan-2-ylamine hydrochloride in the presence of one equivalent of triethylamine. Purification was performed using HPLC with a normal phase column. Elution with a two phase solvent system (A=hexane, B=dichloromethane/methanol, 4:1) gave the title compound in 45% yield, m.p. 230-231° C. MS [(+)ESI, m/z]: 568 [M+H]$^+$

Example 66

N-[2-(4-HYDROXYPHENYL)ETHYL]-10-[(2'-METHOXY-2-METHYL-1,1'-BIPHENYL-4-YL)CARBONYL]-10,11-DIHYDRO-5H-PYRROLO[2,1-C][1,4]BENZODIAZEPINE-3-CARBOXAMIDE

Step A. (2-Methyl-2'-methoxy-[1,1'-biphenyl]-4-yl) carboxylic acid methyl ester

A mixture of 3-methyl-4-bromobenzoic acid methyl ester (2.0 g, 8.7 mmol), 2-methoxyphenyl boronic acid (1.32 g, 8.7 mmol) and sodium carbonate (4.1 g, 38.7 mmol) in toluene:ethanol:water (50 mL:25 mL: 25 mL) was purged with nitrogen for 1 hour. After addition of the tetrakis(triphenylphosphine) palladium(0) catalyst (0.50 g, 0.43 mmol), the reaction mixture was heated at 100° C. overnight. After cooling, the reaction was filtered through Celite® and the cake washed with ethyl acetate. The organic layer was washed with water, dried over anhydrous sodium sulfate, filtered and concentrated in vacuo to give a brown oil. Purification by flash chromatography on silica gel with a solvent gradient from 20% to 50% dichloromethane in hexane gave 2.0 g of product as a colorless oil. MS [(+)APCI, m/z]: 257 [M+H]$^+$. Anal. Calcd. for $C_{16}H_{16}O_3$: C, 74.98; H, 6.29. Found: C, 74.06; H, 6.17.

Step B. 2'-Methoxy-2-methyl-biphenyl-4-carboxylic acid

The (2-methyl-2'-methoxy-[1,1'-biphenyl]-4yl)carboxylic acid methyl ester of Step A (1.9 g, 7.4 mmol) was dissolved in tetrahydrofuran (30 mL) and 1 N sodium hydroxide (15 mL, 15 mmol) was added. The reaction mixture was heated at reflux overnight, then cooled and acidified with 2 N hydrochloric acid. The aqueous layer was extracted with ethyl acetate. The combined organic layers were dried over anhydrous sodium sulfate, filtered and concentrated in vacuo to give 1.6 g of product as a white solid, m.p. 160-162° C. MS [(−)APCI, m/z]: 241 [M−H]$^−$. Anal. Calcd. for $C_{15}H_{14}O_3$: C, 74.36; H, 5.82. Found: C, 73.93; H, 5.71.

Step C. (10,11-Dihydro-5H-pyrrolo[2,1-c][1,4]benzodiazepin-10-yl)-(2'-methoxy-2-methyl-[1,1'-biphenyl]-4-yl)-methanone To a stirred solution of 2'-methoxy-2-methyl-biphenyl-4-carboxylic acid (0.250 g; 1.032 mmol) in dichloromethane (20 mL) was added one drop of N,N-dimethylformamide followed by dropwise addition of oxalyl chloride (0.144 mL; 1.65 mmol). After stirring for one hour, the mixture was thoroughly evaporated to give the crude acid chloride as a brown oil. The acid chloride then was dissolved in dichloromethane (5 mL) and slowly added to a solution of 10,11-dihydro-5H-pyrrolo [2,1-c][1,4] benzodiazepine (0.57 g, 3.10 mmol) and N,N-diisopropylethyl amine (0.79 mL, 4.53 mmol) in dichloromethane (15 mL). After stirring for 1 hour, the reaction was quenched with water. The organic layer was washed with 1 N hydrochloric acid, 1 N sodium hydroxide and brine, dried over anhydrous sodium sulfate, filtered and concentrated in vacuo to give a yellow foam. Purification by flash chromatography using a solvent gradient of 5 to 15% ethyl acetate in hexane yielded a white foam which crystallized upon sonication in ethanol/hexane to give 0.42 g of the desired title product as a white solid, m.p. 133-135° C. MS [(+)ESI, m/z]: 409 [M+H]$^+$. Anal. Calcd. for $C_{27}H_{24}N_2O_2$: C, 79.39; H, 5.92; N, 6.86. Found: C, 79.16; H, 5.87; N, 6.90.

Step D. 2,2,2-Trichloro-1-{10-[(2'-methoxy-2-methyl-[1,1'-biphenyl]-4-yl)carbonyl]-10,11-dihydro-5H-pyrrolo [2,1-c][1,4]benzodiazepin-3-yl}ethanone To a solution of (10,11-dihydro-5H-pyrrolo [2,1-c][1,4] benzodiazepin-10-yl)-(2'-methoxy-2-methyl-[1,1'-biphenyl]-4-yl)-methanone of Step C (1.5 g, 3.67 mmol) in dichloromethane (20 mL) was added N,N-diisopropylethylamine (1.28 mL, 7.35 mmol) followed by slow addition of trichloroacetyl chloride (1.23 mL, 11.0 mmol). The reaction mixture was stirred overnight at room temperature then quenched with water. The organic phase was washed with 0.1 N hydrochloric acid followed by water, then dried over anhydrous sodium sulfate, filtered and concentrated in vacuo to give a green oil. Purification by flash chromatography on silica gel using a solvent system of 20% ethyl acetate in hexane provided 2.1 g of title compound. The material was redissolved in dichloromethane and evaporated to dryness to provide a yellow foam, which was used in the next step. MS [(+)APCI, m/z]: 553 [M+H]$^+$ Anal. Calcd. for $C_{29}H_{23}Cl_3N_2O_3$+0.13 $C_4H_8O_2$+0.13 $CH_2Cl_2$:C, 61.79; H, 4.25; N, 4.86. Found: C, 60.43; H, 4.50; N, 4.80.

Step E. N-[2-(4-Hydroxyphenyl)ethyl]-10-[(2'-methoxy-2-methyl-1,1'-biphenyl-4-yl)carbonyl]-10,11-dihydro-5H-pyrrolo[2,1-c][1,4]benzodiazepine-3-carboxamide The 2,2,2-trichloro-1-[10-(2'-methoxy-2-methyl-biphenyl-4-carbonyl)-10,11-dihydro-5H-benzo[e]pyrrolo[1,2-a][1,4]diazepin-3-yl]-ethanone of step D (0.175 g; 0.316 mmol) and tyramine (0.087 g; 0.632 mmol) were stirred in 3 mL of dimethylsulfoxide under a nitrogen atmosphere at 80° C. for 18 hours. The solution was cooled and 15 mL water were added. The resulting solid was filtered and dried to provide the title compound (0.171 g, 94%), m.p. 138-147° C. MS [(+)ESI, m/z]: 572.2 [M+H]$^+$

Example 67

2,2,2-TRICHLORO-1-{10-[(4-CHLOROPHENOXY)ACETYL]-10,11-DIHYDRO-5H-PYRROLO[2,1-C][1,4]BENZODIAZEPIN-3-YL}ETHANONE

Step A. 10-[(4-Chlorophenoxy)acetyl]-10,11-dihydro-5H-pyrrolo[2,1-c][1,4]benzodiazepine This compound was prepared from 10,11-dihydro-5H-pyrrolo[2,1-c][1,4]benzodiazepine and 4-chlorophenoxyacetyl chloride in the manner of Example 75, step B, m.p. 120-122° C. MS [(+)ESI, m/z]: 353 [M+H]$^+$ Anal. Calcd for $C_{20}H_{17}ClN_2O_2$: C, 68.09; H, 4.86; N, 7.94. Found: C, 67.82; H, 4.87; N, 7.87.

Step B. 2,2,2-Trichloro-1-{10-[(4-chlorophenoxy)acetyl]-10,11-dihydro-5H-pyrrolo[2,1-c][1,4]benzodiazepin-3-yl}ethanone This compound was prepared from 10-[(4-chlorophenoxy)acetyl]-10,11-dihydro-5H-pyrrolo[2,1-c][1,4]benzodiazepine of Step A in the manner of Example 75, step C, m.p. 165-167° C. MS [(+)ESI, m/z]: 497 [M+H]$^+$ Anal. Calcd for $C_{22}H_{16}Cl_4N_2O_3$: C, 53.04; H, 3.24; N, 5.62. Found: C, 53.10; H, 3.39; N, 5.36.

Example 68

10-[(4-CHLOROPHENOXY)ACETYL]-N-[2-(4-HYDROXYPHENYL)ETHYL]-10,11-DIHYDRO-5H-PYRROLO[2,1-C][1,4]BENZODIAZEPINE-3-CARBOXAMIDE

A solution of 2,2,2-trichloro-1-{10-[(4-chlorophenoxy)acetyl]-10,11-dihydro-5H-pyrrolo[2,1-c][1,4]benzodiazepin-3-yl}ethanone of Example 67 (0.3 mmol) and tyramine (0.62 mmol) in dimethylsulfoxide (0.2 mL) and acetonitrile (4 mL) was stirred at 80° C. for 18 hours. The solvents were evaporated and the residue was dissolved in dichloromethane, washed with water, dried over anhydrous sodium sulfate and evaporated. The compound was purified by HPLC (normal phase, Luna® CN bonded packing) and crystallized from ethyl acetate/hexane (0.12 g), m.p. 206-207 ° C. MS [(+)ESI, m/z]: 516 [M+H]$^+$ Anal. Calcd for $C_{29}H_{26}ClN_3O_4$: C, 67.50; H, 5.08; N, 8.14. Found: C, 67.35; H, 5.07; N, 8.08.

Example 69

N-(1,3-BENZODIOXOL-5-YLMETHYL)-10-[(4-CHLOROPHENOXY)ACETYL]-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy) acetyl]-10,11-dihydro-5H-pyrrolo[2,1-c][1,4]benzodiazepin-3-yl}ethanone of Example 67 (0.3 mmol) and piperonylamine (2.2 eq.) in the manner of Example 68, m.p. 168-169° C. MS [(+)ESI, m/z]: 530 [M+H]$^+$ Anal. Calcd for $C_{29}H_{24}ClN_3O_5$: C, 65.72; H, 4.56; N, 7.93. Found: C, 65.79; H, 4.59; N, 7.89.

Example 70

10-[(4-CHLOROPHENOXY)ACETYL]-N-(4-METHYLBENZYL)-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy) acetyl]-10,11-dihydro-5H-pyrrolo[2,1-c][1,4]benzodiazepin-3-yl}ethanone of Example 67 (0.3 mmol) and 4-methylbenzylamine (2.2 eq.) in the manner of Example 68, m.p. 174-176° C. MS [(+)ESI, m/z]: 500 [M+H]$^+$ Anal. Calcd for $C_{29}H_{26}ClN_3O_3$: C, 69.66; H, 5.24; N, 8.40. Found: C, 69.56; H, 5.35; N, 8.37.

Example 71

10-[(4-CHLOROPHENOXY)ACETYL]-N-(3-METHYLBENZYL)-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy)acetyl]-10,11-dihydro-5H-pyrrolo[2,1-c][1,4]benzodiazepin-3-yl}ethanone of Example 67 (0.3 mmol) and 3-methylbenzylamine (2.2 eq.) in the manner of Example 68, m.p. 130-131° C. MS [(+)ESI, m/z]: 500 [M+H]$^+$ Anal. Calcd for $C_{29}H_{26}ClN_3O_3$: C, 69.66; H, 5.24; N, 8.40. Found: C, 69.80; H, 5.30; N, 8.42.

Example 72

10-[(4-CHLOROPHENOXY)ACETYL]-N-[3-(TRIFLUOROMETHYL)BENZYL]-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy) acetyl]-10,11-dihydro-5H-pyrrolo[2,1-c][1,4]benzodiazepin-3-yl}ethanone of Example 67 (0.3 mmol) and 3-trifluoromethylbenzylamine (2.2 eq.) in the manner of example 68, m.p.143-145° C. MS [(+)ESI, m/z]: 554 [M+H]$^+$ Anal. Calcd for $C_{29}H_{23}ClF_3N_3O_3$: C, 62.88; H, 4.18; N, 7.59. Found: C, 62.87; H, 4.08; N, 7.52.

Example 73

10-[(4-CHLOROPHENOXY)ACETYL]-N-(2-HYDROXY-2-PHENYLETHYL)-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy)acetyl]-10,11-dihydro-5H-pyrrolo[2,1-c][1,4]benzodiazepin-3-yl}ethanone of Example 67 (0.3 mmol) and 2-amino-1-phenylethanol (2.2 eq.) in the manner of Example 68, m.p. 157-158° C. MS [(−)ESI, m/z]: 514.3 [M−H]⁻

Example 74

N-(1,1'-BIPHENYL-4-YL)-10-[(4-CHLOROPHENOXY)ACETYL]-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chlorophenoxy)acetyl]-10,11-dihydro-5H-pyrrolo[2,1-c][1,4]benzodiazepin-3-yl}ethanone of Example 67 (0.3 mmol) and biphenyl-4-ylamine (2.2 eq.) in the manner of Example 68, m.p. 201-202° C. MS [(+)ESI, m/z]: 548 [M+H]⁺

Example 75

2,2,2-TRICHLORO-1-{10-[(4-CHLORO-2-METHYLPHENOXY)ACETYL]-10,11-DIHYDRO-5H-PYRROLO[2,1-C][1,4]BENZODIAZEPIN-3-YL}ETHANONE

Step A. 4-Chloro-o-tolyloxyacetic acid chloride

To a cold suspension of 4-chloro-o-tolyloxyacetic acid (17.4 mmol) in 40 mL of dry dichloromethane was added oxalyl chloride (39.15 mmol) followed by one drop of N,N-dimethylformamide. Bubbling immediately began. After 30 minutes, the reaction mixture was warmed in a 45° oil bath for 1.5 hours. The solution was cooled to room temperature and all volatiles were removed by evaporation. Dry nitrogen gas was introduced into the evaporator and more dry dichloromethane was added. This was evaporated again in vacuo. Finally, dry toluene was added to the residue and this was evaporated at reduced pressure. The prepared acid chloride was used without further purification in the following step.

Step B. 10-[(4-Chloro-2-methylphenoxy)acetyl]-10,11-dihydro-5H-pyrrolo[2,1-c][1,4]benzodiazepine To a solution of 4-chloro-o-tolyloxyacetic acid chloride of step A (17.4 mmol) in dichloromethane (25 mL) was added a solution of 10,11-dihydro-5H-pyrrolo[2,1-c][1,4]benzodiazepine (17.4 mmol) and triethylamine (19.14 mmol) in dichloromethane (25 mL) in a rapid dropwise fashion. The mixture was stirred for one hour at room temperature. The reaction mixture was washed with 0.1 N hydrochloric acid (2×) and water (1×), dried over anhydrous sodium sulfate and evaporated. The product was isolated by crystallization from hot ethyl acetate/t-butyl methyl ether (2/1), m.p. 166-167° C. MS [(+)ESI, m/z]: 367 [M+H]⁺ Anal. Calcd for $C_{21}H_{19}ClN_2O_2$: C, 68.76; H, 5.22; N, 7.64. Found: C, 68.53; H, 5.18; N, 7.53.

Step C. 2,2,2-Trichloro-1-{10-[(4-chloro-2-methylphenoxy)acetyl]-10,11-dihydro-5H-pyrrolo[2,1-c][1,4]benzodiazepin-3-yl}ethanone To a cold (0° C.) solution of 10-[(4-chloro-2-methylphenoxy)acetyl]-10,11-dihydro-5H-pyrrolo[2,1-c][1,4]benzodiazepine of step B (2.70 mmol) and triethylamine (0.76 mL) in dichloromethane (15 mL) was added trichloroacetyl chloride (0.90 mL). This was stirred and allowed to warm to room temperature overnight. The reaction mixture was washed with water (2×), 0.1N hydrochloric acid (2×), dilute aqueous sodium bicarbonate (2×) and finally, with water (1×). The organic phase was dried over anhydrous sodium sulfate and evaporated. The product was purified by crystallization from warm ethyl acetate/hexane (3/1), m.p. 156-158° C. MS [(+)ESI, m/z]: 511 [M+H]⁺ Anal. Calcd for $C_{23}H_{18}Cl_4O_3$: C, 53.93; H, 3.54; N, 5.47. Found: C, 53.90; H, 3.45; N, 5.40.

Example 76

N(1,3-BENZODIOXOL-5-YLMETHYL)-10-[(4-CHLORO-2-METHYLPHENOXY-ACETYL]-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chloro-2-methylphenoxy)acetyl]-10,11-dihydro-5H-pyrrolo[2,1-c][1,4]benzodiazepin-3-yl}ethanone of Example 75 (0.3 mmol) and piperonylamine (2.2 eq.) in the manner of Example 68, m.p.181-183° C. MS [(+)ESI, m/z]: 544 [M+H]⁺

Example 77

METHYL 4-{[({10-[(4-CHLORO-2-METHYLPHENOXY)ACETYL]-10,11-DIHYDRO-5H-PYRROLO[2, 1-C][1,4]BENZODIAZEPIN-3-YL}CARBONYL)AMINO]METHYL}BENZOATE

The title compound was synthesized from 2,2,2-trichloro-1-{10-[(4-chloro-2-methylphenoxy)acetyl]-10,11-dihydro-5H-pyrrolo[2,1-c][1,4]benzodiazepin-3-yl}ethanone of Example 75 (0.3 mmol), methyl 4-(aminomethyl)benzoate hydrochloride (2.2 eq.) and triethylamine (2.4 eq.) in the manner of Example 68, m.p.165-167° C. MS [(+)ESI, m/z]: 558 [M+H]⁺ Anal. Calcd for $C_{31}H_{28}ClN_3O_5$: C, 66.72; H, 5.06; N, 7.53. Found: C, 66.46; H, 5.26; N, 7.24.

Example 78

10-[(4-CHLORO-2-METHYLPHENOXY)ACETYL]-N-(4-HYDROXY-3-METHOXYBENZYL)-10,11-DIHYDRO-5H-PYRROLO[2,1-C][1,4]BENZODIAZEPINE-3-CARBOXAMIDE

The title compound was synthesized from 2,2,2-trichloro-1-{10-[(4-chloro-2-methylphenoxy)acetyl]-10,11-dihydro-5H-pyrrolo[2,1-c][1,4]benzodiazepin-3-yl}ethanone of Example 75 (0.3 mmol), 4-hydroxy-3-methoxybenzylamine hydrochloride (2.2 eq.) and triethylamine (2.4 eq.) in the manner of Example 68, m.p. 167-168° C. MS [(+)ESI, m/z]: 546 [M+H]⁺

Example 79

10-[(4-CHLOROPHENOXY)ACETYL]-N-(2',3-DIMETHYL-1,1'-BIPHENYL-4-YL)-10,11-DIHYDRO-5H-PYRROLO[2,1-C][1,4]BENZODIAZEPINE-3-CARBOXAMIDE

Step A. 10-[(4-Chlorophenoxy)acetyl]-10,11-dihydro-5H-pyrrolo[2,1-c][1,4]benzodiazepine-3-carboxylic acid To a stirred solution of 2,2,2-trichloro-1-{10-[(4-chlorophenoxy)acetyl]-10,11-dihydro-5H-pyrrolo[2,1-c][1,4]benzodiazepin-3-yl}ethanone (0.20 mmol) in acetone (1.2 mL) was added 0.15 mL of 2.5 N sodium hydroxide. After stirring for 20 hours the mixture was acidified with 2.0 N hydrochloric acid, extracted into ethyl acetate, washed with brine, and dried over anhydrous sodium sulfate. The solution was then evaporated and the residue purified by trituration with diethylether. The solid (0.066 g, 83%) was collected and dried, m.p. 168° C. MS [(+)ESI, m/z]: 395 [M+H]$^+$ Anal. Calcd for $C_{21}H_{17}ClN_2O_4$: C, 63.56; H, 4.32; N, 7.06. Found: C, 63.66; H, 4.48; N, 6.86

Step B. 10-[2-(4-Chloro-phenoxy)-acetyl]-10,11-dihydro-5H-benzo[e]pyrrolo[1,2-a][1,4]diazepine-3-carbonyl chloride To a solution of 10-[(4-chlorophenoxy)acetyl]-10,11-dihydro-5H-pyrrolo[2,1-c][1,4]benzodiazepine-3-carboxylic acid of step A (0.33 mmol) in dichloromethane (3 mL) was added a drop of N,N-dimethylformamide followed by oxalyl chloride (0.532 mmol). After stirring for 0.5 hour at room temperature, the solution was heated to reflux for three hours. The solvent and excess oxalyl chloride were evaporated to yield the crude product, which was used without further purification.

Step C. 10-[(4-Chlorophenoxy)acetyl]-N-(2',3-dimethyl-1,1'-biphenyl-4-yl)-10,11-dihydro-5H-pyrrolo[2,1-c][1,4]benzodiazepine-3-carboxamide To a stirred solution of 10-[2-(4-chloro-phenoxy)-acetyl]-10,11-dihydro-5H-benzo[e]pyrrolo[1,2-a][1,4]diazepine-3-carbonyl chloride of step B (0.415 mmol) in anhydrous tetrahydrofuran (3 mL) was added triethylamine (0.829 mmol) and 3,2'-dimethylbiphen-4-ylamine hydrochloride (0.415 mmol). The solution was stirred for 18 hours at ambient temperature. The solvent was evaporated, the residue was taken up in dichloromethane, washed with water, dried over anhydrous sodium sulfate, and evaporated. Chromatography on silica gel using 55:23:22 hexane/ethyl acetate/dichloromethane as eluant gave the title compound as an amorphous solid. This was crystallized from ethyl acetate/hexane to afford 0.17 g of the title product (71% yield), m.p. 159-161° C. MS [(+)ESI, m/z]: 576 [M+H]$^+$ Anal. Calcd for $C_{35}H_{30}ClN_3O_3$: C, 72.97; H, 5.25; N, 7.29. Found: C, 72.59; H, 5.28; N, 7.24.

Example 80

2,2,2-TRICHLORO-1-[10-{[(4-BROMOPHENYL)THIO]ACETYL}-10,11-DIHYDRO-5H-PYRROLO[2,1-C][1,4]BENZODIAZEPINE-3-YL]-ETHANONE

Step A. 10-{[2-(4-Bromophenyl)thio]acetyl}-10,11-dihydro-5H-pyrrolo[2,1-c][1,4]benzodiazepine The title compound was synthesized from (4-bromo-phenylsulfanyl)-acetic acid and 10,11-dihydro-5H-pyrrolo[2,1-c][1,4]benzodiazepine in the manner of Example 35, step E.

Step B. 2,2,2-Trichloro-1-[10-{[(4-bromophenyl)thio]acetyl}-10,11-dihydro-5H-pyrrolo[2,1-c][1,4]benzodiazepine-3-yl]-ethanone The title compound is synthesized from 10-{[2-(4-bromophenyl)thio]acetyl}-10,11-dihydro-5H-pyrrolo[2,1-c][1,4]benzodiazepine of step B in the manner of Example 35, step F.

Example 81

10-{[(4-BROMOPHENYL)THIO]ACETYL}-N-(3,4-DICHLOROBENZYL)-10,11-DIHYDRO-5H-PYRROLO[2,1-C][1,4]BENZODIAZEPINE-3-CARBOXAMIDE

To an 18×150 mm reaction vessel was added 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 (0.23 mmol), acetonitrile (2.5 mL), 3,4-dichlorobenzylamine (0.49 mmol), and dimethylsulfoxide (0.81 mmol). The stirred solution was heated to 85° C. for 20 hours. The solvent was evaporated and the residue was dissolved in 5 mL dichloromethane. The solution was washed twice with water, dried over anhydrous sodium sulfate, and evaporated. The crude product was purified using normal phase HPLC with a two phase solvent system (A=hexane, B=dichloromethane/methanol, 4:1) to give the title product, m.p. 150° C. MS [(+)ESI, m/z]: 614 [M+H]$^+$ Anal. Calcd for $C_{28}H_{22}BrCl_2N_3O_2S$: C, 54.65; H, 3.60; N, 6.83. Found: C, 54.68; H, 3.50; N, 6.73.

Example 82

10-{[(4-BROMOPHENYL)THIO]ACETYL}-N-(4-HYDROXY-3-METHOXYBENZYL)-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and 4-aminomethyl-2-methoxyphenol hydrochloride in the presence of with one equivalent of triethylamine, m.p. 168° C. MS [(+)ESI, m/z]: 592 [M+H]$^+$ Anal. Calcd for $C_{29}H_{26}BrN_3O_4S$: C, 58.79; H, 4.42; N, 7.09. Found: C, 58.65; H, 4.46; N, 6.86.

Example 83

10-{[(4-BROMOPHENYL)THIO]ACETYL}-N-(4-METHYLBENZYL)-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and 4-methylbenzylamine, m.p. 131-132° C. MS [(+)ESI, m/z]: 560 [M+H]$^+$ Anal. Calcd for $C_{29}H_{26}BrN_3O_2S$: C, 62.14; H, 4.68; N, 7.50. Found: C, 62.23; H, 4.59; N, 7.37.

Example 84

N-(1,3-BENZODIOXOL-5-YLMETHYL)-10-{[(4-BROMOPHENYL)THIO]ACETYL}-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and C-benzo[1,3]dioxol-5-yl-methylamine, m.p. 154-155° C. MS [(+)ESI, m/z]: 590 [M+H]$^+$ Anal. Calcd for $C_{29}H_{24}BrN_3O_4S$: C, 58.99; H, 4.10; N, 7.12. Found: C, 58.96; H, 4.26; N, 7.03.

Example 85

10-{[(4-BROMOPHENYL)THIO]ACETYL}-N-[3-(TRIFLUOROMETHYL)BENZYL]-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and 3-trifluoromethylbenzylamine, m.p. 102° C. MS [(+)ESI, m/z]: 614 [M+H]$^+$ Anal. Calcd for $C_{29}H_{23}BrF_3N_3O_2S$: C, 56.69; H, 3.77; N, 6.84. Found: C, 56.79; H, 3.66; N, 6.76.

Example 86

10-{[(4-BROMOPHENYL)THIO]ACETYL}-N-[2-(4-HYDROXYPHENYL)ETHYL]-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and 4-(2-aminoethyl)-phenol, m.p. 168-169° C. MS [(+)ESI, m/z]: 574 [M+H]$^+$

Example 87

10-{[(4-BROMOPHENYL)THIO]ACETYL}-N-(1,2,3,4-TETRAHYDRONAPHTHALEN-1-YL)-10,11-DIHYDRO-5H-PYRROLO[2,1-C][1,4]BENZODIAZEPINE-3-CARBOXAMIDE

The title compound was synthesized in the manner of Example 81 from 2,2,2-trichloro-1-[10-{[(4-bromophenyl)thio]acetyl}-10,11-dihydro-5H-pyrrolo[2,1-c][1,4]benzodiazepine-3-yl]-ethanone of Example 80 and 1,2,3,4-tetrahydronaphthalen-1-ylamine, m.p. 163-165° C. MS [(+)ESI, m/z]: 586 [M+H]$^+$ The following Examples 88-104 were prepared by the processes described herein, and illustrated by Examples 1-87 above.

Example 88

N-(4-BENZOYLBENZYL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE mp 148-150° C.; MS (ESI) m/z 628.

Example 89

N-(3,5-DIMETHOXYBENZYL)-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE mp 175° C.; MS (ESI) m/z 602.

Example 90

10-[(2,2'-DIMETHYL-1,1'-BIPHENYL-4-YL)CARBONYL]-N-(2,2-DIPHENYLETHYL)-10,11-DIHYDRO-5H-PYRROLO[2,1-C][1,4]BENZODIAZEPINE-3-CARBOXAMIDE mp 126-128° C.; MS (ESI) m/z 616.

Example 91

N-[4-(DIMETHYLAMINO)BENZYL]-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE mp 154-155° C.; MS (ESI) m/z 569.

Example 92

N-(2,3-DIHYDRO-1H-INDEN-1-YL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE mp 122-124° C.; MS (ESI) m/z 550.

Example 93

N-(2,3-DIHYDRO-1H-INDEN-2-YL)-10-[(2,2'-DIMETHYL-1,1'-BIPHENYL-4-YL)CARBONYL]-10,11-DIHYDRO-5H-PYRROLO[2,1-C][1,4]BENZODIAZEPINE-3-CARBOXAMIDE mp 219-220° C.; MS (ESI) m/z 550.

Example 94

10-[(4-CHLOROPHENOXY)ACETYL]-N-(1,2,3,4-TETRAHYDRONAPHTHALEN-1-YL)-10,11-DIHYDRO-5H-PYRROLO[2,1-C][1,4]BENZODIAZEPINE-3-CARBOXAMIDE mp 199-200° C.; MS (ESI) m/z 526.

Example 95

METHYL 4-[({10-[(4-CHLOROPHENOXY)
ACETYL]-10,11-DIHYDRO-5H-PYRROLO[2,1-C]
[1,4]BENZODIAZEPIN-3-YL}CARBONYL)
AMINO]-2-METHOXYBENZOATE mp 172-174° C.; MS (ESI) m/z 560.

Example 96

ETHYL 4-[({10-[(4-CHLOROPHENOXY)
ACETYL]-10,11-DIHYDRO-5H-PYRROLO[2,1-C]
[1,4]BENZODIAZEPIN-3-YL}CARBONYL)
AMINO]BENZOATE mp 199-201° C.; MS (ESI) m/z 544.

Example 97

10-[(4-CHLOROPHENOXY)ACETYL]-N-(9-HY-
DROXY-9H-FLUOREN-2-YL)-10,11-DIHYDRO-
5H-PYRROLO[2,1-C][1,4]BENZODIAZEPINE-3-
CARBOXAMIDE mp 176-182° C.; MS (ESI) m/z 576.

Example 98

DIMETHYL 5-[({10-[(4-CHLOROPHENOXY)
ACETYL]-10,11-DIHYDRO-5H-PYRROLO[2,1-C]
[1,4]BENZODIAZEPIN-3-YL}CARBONYL)
AMINO]ISOPHTHALATE mp 213-217° C.; MS (ESI) m/z 588.

Example 99

ETHYL 3-[({10-[(4-CHLOROPHENOXY)
ACETYL]-10,11-DIHYDRO-5H-PYRROLO[2,1-C]
[1,4]BENZODIAZEPIN-3-YL}CARBONYL)
AMINO]BENZOATE mp 179-180° C.; MS (ESI) m/z 544.

Example 100

N-(1,1'-BIPHENYL-3-YL)-10-[(4-CHLOROPHE-
NOXY)ACETYL]-10,11-DIHYDRO-5H-PYR-
ROLO[2,1-C][1,4]BENZODIAZEPINE-3-CAR-
BOXAMIDE mp 185-189° C.; MS (ESI) m/z 548.

Example 101

10-[(4-CHLOROPHENOXY)ACETYL]-N-[3-
(DIMETHYLAMINO)PHENYL]-10,11-DIHY-
DRO-5H-PYRROLO[2,1-C][1,4]BENZODIAZ-
EPINE-3-CARBOXAMIDE mp 133-136° C.; MS (ESI) m/z 515.

Example 102

N-(4-TERT-BUTYLPHENYL)-10-[(4-CHLO-
ROPHENOXY)ACETYL]-10,11-DIHYDRO-5H-
PYRROLO[2,1-C][1,4]BENZODIAZEPINE-3-
CARBOXAMIDE mp 111-113° C.; MS (ESI) m/z 528.

Example 103

N-(7-BROMO-9-OXO-9H-FLUOREN-2-YL)-10-
[(4-CHLOROPHENOXY)ACETYL]-10,11-DIHY-
DRO-5H-PYRROLO[2,1-C][1,4]BENZODIAZ-
EPINE-3-CARBOXAMIDE mp 277-278° C.; MS (ESI) m/z 650.

Example 104

N-[2-(1,3-BENZODIOXOL-5-YL)ETHYL]-10-{
[(4-BROMOPHENYL)THIO]ACETYL}-10,11-
DIHYDRO-5H-PYRROLO[2,1-C][1,4]BENZODI-
AZEPINE-3-CARBOXAMIDE mp 143° C.; MS (ESI) m/z 604.

Biological Activity Examples

The subject compounds of the present invention were tested for biological activity according to the following procedures.

Pharmacology

The FSH antagonist activities of the compounds of this invention were demonstrated by evaluating representative compounds of this invention in the following test procedures.

Example 105

Follicle-Stimulating Hormone Receptor-Dependent
Cre-Luciferase Reporter Gene Assay for the
Identification of Follicle-Stimulating Hormone
(FSH) Antagonists A Chinese hamster ovarian cell line that stably produces the human FSH receptor and a luciferase reporter gene regulated by cAMP response elements was used to identify and determine the relative potencies of human FSH receptor antagonists. See for example, Kelton, C. A., et al. *Mol. Cell. Endocrinol.* 89:141-151 (1992), Tilly, J. L., et al. *Endocrinology* 131:799-806(1992), and George, S. E., et al. *J. Biomol. Screening* 2:235-240 (1997).

Materials and Methods: Reagents

Compound Vehicle: Stock compounds were solubilized in an appropriate vehicle, e.g., phosphate buffered saline (PBS) or dimethyl sulfoxide (DMSO), at 30 mM. The compounds were subsequently diluted in DMSO to working dilutions of 1 and 20 or 30 mM for 2-dose testing format and 1 μM-10 mM for dose-response format. The DMSO dilutions were diluted 500-fold in sterile growth medium [D-MEM/F-12 (GIBCO/BRL; Grand Island, NY) containing 15 mM HEPES, 2 mM 1-glutamine, pyridoxine hydrochloride, phenol red and 5% FetalClone® II (HyClone Laboratories, Inc; Logan, Utah), 0.2% DMSO, 100 units penicillin G/ml, and 100 μg streptomycin sulfate/ml (GIBCO/BRL)]. The concentration of the vehicle in each of the compound dilutions was the same.

Positive Controls: Purified human FSH (>98%) was purchased from Cortex Biochem, Inc. (San Leandro, Calif.) and 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-benzamide (an FSH-R thiazolidinone antagonist) was prepared by processes described by R. A. Scheuerman et al. in U.S. Pat. No. 6,426,357 (Affymax).

Preparation of Cells

The CHO FSH-R 6CRE-Luc cells (1D7 cells) were obtained from Affymax (Palo Alto, Calif.). These Chinese hamster ovary cells (CHO-K1) were engineered genetically to stably express the recombinant human FSH receptor gene and a luciferase reporter gene under the regulation of 6 copies of a cAMP response element. The cells were plated one day prior to treatment into 96-well white opaque plates at a density of 50,000 cells/100 μl/well in growth medium. On the day of treatment, the growth medium was removed from the wells by aspiration and 50 μl of fresh growth medium was added to each well. The cells were incubated at 37° C. in a humidified incubator with 5% $CO_2$/95% air.

Assay

Test compounds diluted to 2× final concentration in growth medium containing 2× EC50 purified human FSH (0.8 ng/ml) were added to the wells to achieve a final volume of 100 μl of medium containing 0.25% (v/v) vehicle. The treated cells were incubated for 4 hours at 37° C. in a humidified incubator with 5% $CO_2$/95% air. At the end of the incubation period, luciferase activity was measured by chemiluminescence using a commercially available kit (LucScreen, Tropix, Inc., Bedford, Mass.) according to the manufacturer's specifications, except that Buffer 1 and Buffer 2 were mixed together in equal proportion prior to the addition of 100 μl of the combined reagents to each well. Chemiluminescence was detected using a luminometer (EG & G Berthold Microlumat LB 96 P, Wallac, Gaithersburg, Md.) with chemiluminescence measured for 1 sec/well. Background luminescence was measured for each well prior to the addition of the LucScreen reagent.

Experimental Groups

In the 96-well 2-dose format, each compound was tested in duplicate at each dose. The controls also were tested in duplicate on each plate and consisted of vehicle control and 3 positive controls ($EC_{50}$ of phFSH (0.4 ng/ml), $EC_{100}$ of phFSH (1000 ng/ml), and $IC_{50}$ of 3-[(2S*,5R*)-5-{[2-(1H-Indol-3-yl)-ethylcarbamoyl]-methyl}-4-oxo-2-(5-phenylethynl-thiophen-2-yl)-thiazolidin-3-yl]-benzamide (2 μM) in the presence of $EC_{50}$ of purified human FSH). One plate was used to test a maximum of 22 compounds.

In the 96-well dose-response format, each compound was tested in triplicate at each of 6 doses in the presence of the $EC_{50}$ of purified human FSH. The $EC_{50}$ of purified human FSH alone was tested in triplicate with each test compound. The doses chosen to test each compound were extrapolated from the initial 2-dose screening process. Along with the test compounds, purified human FSH also was tested in a dose response (0.03, 0.1, 0.3, 1, 3, 10, and 30 ng/ml) for a positive control and quality control. One plate was used for 3 test compounds and the FSH positive control.

Analysis of the Results

Luciferase activity is expressed as relative light units/sec/well. Luciferase activity in antagonist was compared to the appropriate negative and positive controls. For 2-dose testing, results are reported as luciferase activity and are expressed as percent inhibition of the response obtained from the $EC_{50}$ of FSH. For dose-response testing, results are reported as $IC_{50}$ values. Data were analyzed statistically by one-way analysis of variance with appropriate weighting and transformation and relevant paired test as determined by Biometrics (Wyeth Research, Princeton, N.J.). $IC_{50}$ values were calculated using statistical software from SAS (SAS Institute, Inc., Cary, N.C.)

Reference Compounds

Test compounds were compared to the effect of purified human FSH and 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-benzamide in 2-dose format and $EC_{50}$ concentration of purified human FSH in dose-response format.

Example 106

In Vitro Bio-Assay, Selectivity and Dependency of Agonists and Antagonists to the FSH Receptor This assay was used to verify in vitro potency, efficacy, selectivity and receptor dependency of hits found to inhibit an FSH-R-CRE-luciferase driven reporter.

Methods: Reagents

Compound Vehicle: Stock compounds were solubilized in 100% DMSO (Sigma-Aldrich Chemical Co., St. Louis, Mo.) at a concentration of 30 mM. The compounds subsequently were diluted in sterile assay medium consisting of Opti-MEM® I (Invitrogen/Life Technologies, Carlsbad, Calif.) with 0.1% (w/v) BSA (Sigma-Aldrich) prior to use in the bio-assay. The final concentration of DMSO in the assay was 0.1%.

Preparation of CHO-3D2 Cells

The day prior to the experiment, CHO-3D2 cells (hFSH-R)(1) were plated into 96-well tissue culture plates (Falcon®, BD Biosciences, San Jose, Calif.) at a density of 30,000 cells/well in DMEM/F12 medium (Invitrogen/Life Technologies) supplemented with 5% Fetal Clone II (Hyclone), 2 mM L-glutamine (Invitrogen/Life Technologies) and penicillin/streptomycin (100 U/ml, Invitrogen/Life Technologies). Plated cells are then incubated at 37° C. in a humidified 5% $CO_2$/95% air atmosphere.

Assay: On the day of the assay, cells were washed three times with 100 μl/well of assay medium consisting of Opti-MEM® I (Invitrogen/Life Technologies) with 0.1% (w/v) BSA (Sigma-Aldrich). Medium was removed and 100 μl of assay medium was added to each well. Plates were incubated for an additional 30 minutes at 37° C. Medium was then removed and cells were challenged for 30 minutes at 37° C. in 50 μl of assay media containing vehicle, purified hFSH (>95% pure; Cortex Biochem, Inc., San Leandro, Calif.) in the presence or absence of test compounds. Reactions were terminated by the addition of 50 μl of 0.2N hydrochloric acid to each well and cAMP-accumulation was measured by radioimmunoassay (RIA) using a commercially available kit (Amersham Biosciences, Piscataway, N.J.).

Experimental Groups

All test compounds were evaluated in a dose-response paradigm ranging from 0.01 to 30 μM. Controls and test compounds were evaluated in quadruplicate in a 96-well format. Cells were treated with vehicle, hFSH at $EC_{20}$ (1.85 ng/mL=53 pM), or the compounds in the presence or absence of hFSH at its $EC_{20}$ dose. The ability of the compounds to inhibit the cAMP-accumulation induced by hFSH was evaluated by RIA.

In every assay, the $EC_{20}$ concentration was calculated and only those experiments in which the $EC_{20}$ concentrations were equal to 1.85±0.4 ng/mL were accepted as valid. In the 96-well format, the first column contained the negative control (assay media+0.1% DMSO), the second column contained the positive control, hFSH at its $EC_{20}$+0.1% DMSO (1.85 ng/ml or 53 pM), followed by six concentrations of the compound ranging from 0.03-30 μM in the presence of the hFSH at its $EC_{20}$ concentration (1.85 ng/ml or 53 pM).

Along with the test compounds, FSH also was run as a positive control in the agonist mode using concentrations ranging from 0.1-1000 ng/ml.

Selectivity Studies:

cAMP accumulation assays using CHO-25 (hTSH-R) cells were performed as described above for the CHO-3D2 cells with the following exceptions: CHO-25 cells were plated at a density of 50,000 cells/well (2). All test compounds were evaluated in a dose-response paradigm ranging from 0.01 to 30 μM. Controls and test compounds were evaluated in quadruplicate. Cells were treated with vehicle, hTSH at $EC_{20}$ (5 nM; hTSH >98% pure, Cortex Biochem, Inc.), or the compounds in the presence or absence of the hTSH at its $EC_{20}$ concentration. The ability of the compounds to inhibit cAMP-accumulation induced by hTSH was evaluated by RIA.

Along with the test compounds, hTSH was also run as a positive control in the agonist mode using concentrations ranging from 0.01 μM-1000 μM.

Non-Receptor Mediated Responses:

cAMP-accumulation assays using CHO-K1 cells (parental cell line) were performed as described above for the CHO-3D2 cells. All test compounds were evaluated in a dose-response paradigm ranging from 0.01 to 30 μM. Controls and test compounds were evaluated in quadruplicate. Cells were treated with vehicle, 5 μM forskolin that induces the equivalent fmol/ml concentration of cAMP-accumulation induced by the hFSH at its $EC_{20}$ (5 μM forskolin, Sigma-Aldrich Chemical Co, St. Louis, Mo.; previously calculated during characterization of the bio-assays), or the compounds in the presence or absence of the 5 μM forskolin. The ability of the compounds to inhibit the cAMP-accumulation induced by forskolin was evaluated by RIA.

Along with the test compounds, forskolin also was run as a positive control in agonist mode using concentrations ranging from 0.01 μM to 1000 μM.

Analysis of Results cAMP accumulation is expressed as fmol/ml. cAMP accumulation in the agonist mode, or the ability of the compound to inhibit hFSH-, hTSH-, or forskolin-induced cAMP-accumulation in the antagonist mode, was compared to the appropriate negative and positive controls. Data were analyzed by one-way analysis of variance and significant differences between treatments and control determined by Least Significant Difference test.

Reference Compounds

Test compounds were compared to the effect of purified human FSH. In the paradigm, hFSH induced a concentration-dependent increase in cAMP accumulation, with apparent $EC_{80}$=22.55 ng/ml, $EC_{50}$=6.03 ng/ml and $EC_{20}$=1.85 ng/ml, calculated using a four-parameter logistic equation. The same comparison was performed with hTSH and forskolin.

Biological Activity

Based on the results obtained in the standard pharmacological test procedures, the compounds of this invention were shown to block cellular function of FSH, in vitro, including the production of second messenger cAMP and estradiol in rat ovarian granulosa cells. Representative compounds of this invention were found to selectively interact with the FSH receptor, but not to antagonize binding of FSH to its receptor (Table 1). As such, the compounds of this invention can be useful as female contraceptive agents.

TABLE 1

| Example | CRE % inhibition (μM) | CRE IC50 μM | cAMP IC50 μM | cAMP % efficacy |
|---|---|---|---|---|
| 14 | | 1.71 | 2.6 | 86 |
| 15 | | 2.6 | 0.4 | 90 |
| 16 | | 8.5 | 14 | 65 |
| 8 | | 2.39 | 3.6 | 63 |
| 17 | | 6.39 | 2.6 | 88 |
| 18 | 58(30) | | >30 | |
| 19 | 30(30) | | | |
| 20 | | 12.01 | >30 | |
| 21 | | 6.2 | >30 | |
| 22 | | 2.88 | 3 | 62 |
| 23 | | 1.41 | 7.7 | 77 |
| 88 | | >30 | | |
| 36 | 60(30) | | | |
| 37 | | 4.03 | 0.7 | 80 |
| 38 | | 1.69 | 0.5 | 83 |
| 39 | | >30 | | |
| 40 | | 1.05 | 0.4 | 90 |
| 41 | 62(30) | | | |
| 42 | | 4.33 | 6.3 | 74 |
| 43 | 56(30) | | | |
| 44 | | 1.35 | >30 | |
| 45 | | >30 | | |
| 89 | | >30 | | |
| 46 | 44(30) | | | |
| 24 | | >30 | | |
| 47 | | >30 | | |
| 48 | | >30 | | |
| 49 | | >30 | | |
| 50 | | >30 | | |
| 51 | | >30 | | |
| 52 | | >30 | | |
| 53 | | >30 | | |
| 25 | 59(30) | | | |
| 26 | 62(30) | | | |
| 90 | | >30 | | |
| 27 | 52(30) | | | |
| 28 | | >30 | | |
| 29 | 52(30) | | | |
| 30 | 62(30) | | | |
| 54 | 46(30) | | | |
| 55 | | >30 | 13 | 60 |
| 91 | | >30 | | |
| 56 | | 30 | | |
| 57 | | >30 | | |
| 31 | | 0.8 | 0.2 | 100 |
| 58 | | >30 | | |
| 59 | | >30 | | |
| 60 | | 1.13 | 0.4 | 95 |
| 61 | | 4.23 | 2.8 | 82 |
| 32 | | ~30 | | |
| 33 | | 5.65 | >30 | |
| 92 | | >30 | | |
| 93 | | >30 | | |
| 13 | | 8.2 | 30 | |
| 61 | 50(30) | | | |
| 63 | | >30 | | |
| 64 | | 3.4 | 1.3 | 79 |
| 65 | | >30 | | |
| 4 | 9(30) | | | |
| 5 | 14(30) | | | |
| 2 | | 25.67 | 1.2 | 100 |
| 7 | | 2.25 | 0.3 | 89 |
| 9 | 37(30) | | | |
| 10 | | 4.14 | 0.9 | 97 |
| 3 | 8(30) | | | |
| 11 | | 14.87 | | |

TABLE 1-continued

| Example | CRE % inhibition (μM) | CRE IC50 μM | cAMP IC50 μM | cAMP % efficacy |
|---|---|---|---|---|
| 12 | | 11.92 | | |
| 34 | | 5.37 | 2.6 | |
| 66 | | >30 | | |
| 69 | 21(30) | | | |
| 70 | 17(30) | | | |
| 71 | 7(30) | | | |
| 72 | | >30 | | |
| 68 | | 13.24 | | |
| 94 | | >30 | | |
| 73 | | 25.07 | | |
| 76 | 15(30) | | | |
| 77 | 3.5(30) | | | |
| 74 | 6(30) | | | |
| 78 | 33(30) | | | |
| 79 | 13(30) | | | |
| 95 | | >30 | | |
| 96 | | >30 | | |
| 97 | | >30 | | |
| 98 | | >30 | | |
| 99 | | >30 | | |
| 100 | | >30 | | |
| 101 | | >30 | | |
| 102 | | >30 | | |
| 103 | | >30 | | |
| 81 | | >30 | | |
| 104 | | >30 | | |
| 82 | 37(30) | | | |
| 83 | 24(30) | | | |
| 84 | 27(30) | | | |
| 85 | 24(30) | | | |
| 86 | 35(30) | | | |
| 87 | 3(30) | | | |

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention. Each reference cited in the present application, including literature references, books, patents and patent applications, is incorporated herein by reference in its entirety.

What is claimed is:
1. A compound having the Formula I:

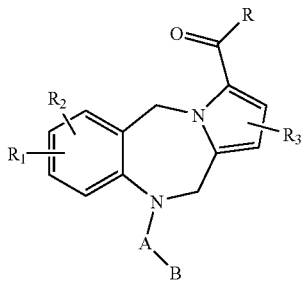

wherein
$R_1$ and $R_2$ are selected independently from the group consisting of hydrogen, $(C_1-C_6)$ alkyl, halogen, trifluoromethyl, hydroxyl, $(C_1-C_6)$ alkoxy, —$OCF_3$, carboxy, —CONH[$(C_1-C_6)$alkyl], —CON[$(C_1-C_6)$ alkyl]$_2$, amino, $(C_1-C_6)$ alkylamino and —NHCO[$(C_1-C_6)$ alkyl];
$R_3$ is selected from the group consisting of hydrogen, $(C_1-C_6)$ alkyl, $(C_1-C_6)$ alkoxy, hydroxyl, amino, $(C_1-C_6)$ alkylamino, —C(O) alkyl and halogen;
A is —C=O;
B is selected independently from the group consisting of

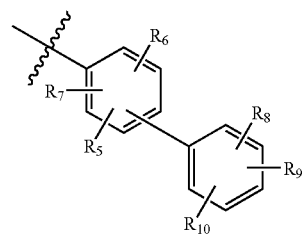

(a)

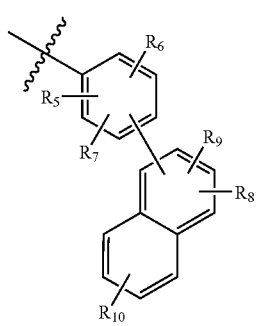

(b) and

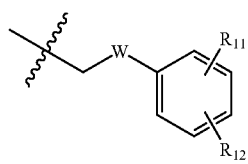

(c)

wherein $R_5$, $R_6$, $R_7$, $R_8$, $R_9$ and $R_{10}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{13}$, —$SO_2N(R_{13})_2$, —$(CH_2)_p CN$, —$(CH_2)_p COOR_{14}$, —$(CH_2)_p NR_{51}R_{52}$, —$(CH_2)_p CONR_{51}R_{52}$, —CH=NOH, —CH=NO—$(C_1-C_6)$ alkyl,

and —C(O)aryl wherein the aryl is optionally substituted by alkyl;
$R_{11}$ and $R_{12}$ are selected independently from the group consisting of hydrogen, alkyl and halogen;
W is O or S;
$R_{13}$ and $R_{14}$ are each independently hydrogen or alkyl;
$R_{51}$ and $R_{52}$ are each independently hydrogen or alkyl;
or $R_{15}$ and $R_{16}$ can be taken together with the nitrogen to which they are attached to form a 4-6 membered saturated ring optionally containing one or more O, S or N atoms;

p is 0 or 1;

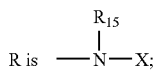

$R_{15}$ is hydrogen or alkyl;

X is —F-G

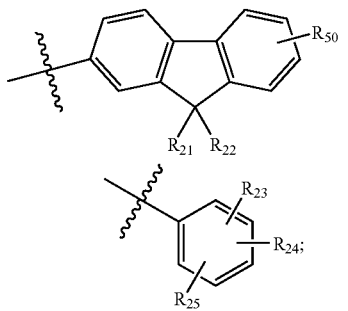

F is selected from the group consisting of

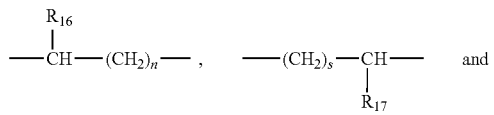

aryl optionally substituted by alkyl;

n is an integer from 0 to 3;

s is an integer from 1 to 3;

$R_{16}$ is selected from the group consisting of hydrogen, alkyl, and hydroxyalkyl;

$R_{17}$ is selected from the group consisting of hydroxy, dialkylamino and aryl;

G is

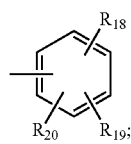

or F and G taken together can form a cycloalkyl group having an aryl group fused thereto;

and $R_{18}$, $R_{19}$ and $R_{20}$ are selected independently from the group consisting of hydrogen, alkyl, alkoxy, halogen, trifluoromethyl, hydroxy, trifluoromethoxy, aryloxy, —(CO)aryl, carboxy, carbalkoxy, amino, aminoalkyl, alkylamino, dialkylamino and aryl optionally substituted by alkyl; or when $R_{18}$ is hydrogen and $R_{19}$ and $R_{20}$ are on adjacent carbon atoms, then $R_{19}$ and $R_{20}$ can together form —O(—$CH_2$)$_m$—O— wherein m is 1 or 2;

$R_{21}$ and $R_{22}$ are each independently hydrogen or hydroxyl; or $R_{21}$ and $R_{22}$ taken together with the carbon to which they are attached can form a carbonyl group;

$R_{23}$, $R_{24}$ and $R_{25}$ are selected independently from the group consisting of hydrogen, alkyl, alkoxy, carbalkoxy, dialkylamino, $NH_2$ and phenyl optionally substituted with —$CH_3$; and $R_{50}$ is H or halogen;

or a salt thereof.

2. A compound of claim 1 or a salt thereof wherein $R_1$, $R_2$, $R_3$ and $R_{15}$ are each H.

3. A compound of claim 2 or a salt thereof wherein X is F-G.

4. A compound of claim 2 or a salt thereof wherein X is F-G, wherein F is selected from the group consisting of —$CH_2$—, —($CH_2$)$_2$—, —($CH_2$)$_3$—, —($CH_2$)$_4$—, —$CH_2$CH(phenyl)-, —CH($CH_3$)—, —($CH_2$)$_2$CH(phenyl)-, —CH($CH_3$)($CH_2$)$_2$—, —$CH_2$CH(OH)—, —CH($CH_2$OH)—, —$CH_2$CH(N($CH_3$)$_2$)— and phenyl optionally substituted with methyl.

5. A compound of claim 2 or a salt thereof wherein X is F-G, wherein each of said $R_{18}$, $R_{19}$ and $R_{20}$ of said G is selected from the group consisting of hydrogen, —$CH_3$, —$CF_3$, —$OCH_3$, —$OCF_3$, halogen, —CO-phenyl, OH, —N($CH_3$)$_2$, —$COOCH_3$, phenoxy, —$NH_2$ and —$CH_2NH_2$; or when $R_{18}$ is hydrogen and $R_{19}$ and $R_{20}$ are on adjacent carbon atoms, then $R_{19}$ and $R_{20}$ can together form —O(—$CH_2$)$_m$—O— wherein m is 1 or 2.

6. A compound of claim 2 or a salt thereof wherein X is F-G, wherein:

F is selected from the group consisting of —$CH_2$—, —($CH_2$)$_2$—, —($CH_2$)$_3$—, —($CH_2$)$_4$—, —$CH_2$CH(phenyl)-, —CH($CH_3$)—, —($CH_2$)$_2$CH(phenyl)-, —CH($CH_3$)($CH_2$)$_2$—, —$CH_2$CH(OH)—, —CH($CH_2$OH)—, —$CH_2$CH(N($CH_3$)$_2$)— and phenyl optionally substituted with methyl; and each of said $R_{18}$, $R_{19}$ and $R_{20}$ of said G is selected from the group consisting of hydrogen —$CH_3$, —$CF_3$, —$OCH_3$, —$OCF_3$, halogen, —CO-phenyl, OH, —N($CH_3$)$_2$, $COOCH_3$, phenoxy, —$NH_2$ and —$CH_2NH_2$; or when $R_{18}$ is hydrogen and $R_{19}$ and $R_{20}$ are on adjacent carbon atoms, then $R_{19}$ and $R_{20}$ can together form —O(—$CH_2$)$_m$—O— wherein m is 1 or 2.

7. A compound of claim 2 or a salt thereof wherein F and G taken together form a group of formula:

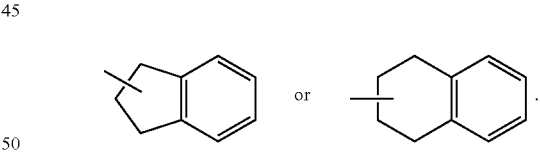

8. A compound of claim 2 or a salt thereof wherein X is:

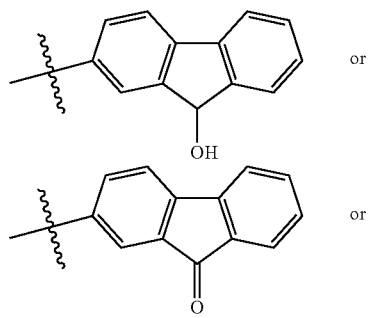

-continued

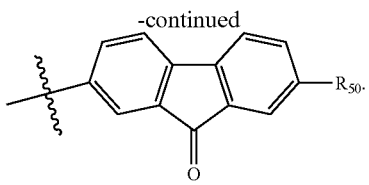

9. A compound of claim 2 or a salt thereof wherein X is

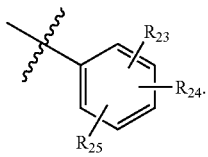

10. A compound of claim 2 or a salt thereof wherein X is

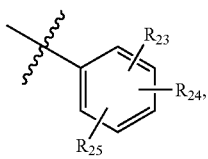

wherein $R_{23}$, $R_{24}$ and $R_{25}$ are each independently selected from the group consisting of —OCH$_3$, —COOCH$_3$, —COOCH$_2$CH$_3$, —C(CH$_3$)$_3$, —NH$_2$ and phenyl optionally substituted with —CH$_3$.

11. A compound of claim 2 or a salt thereof wherein B has the structure (a).

12. A compound of claim 11 or a salt thereof wherein said $R_5$, $R_6$, $R_7$, $R_8$, $R_9$ and $R_{10}$ of said structure (a) are each independently selected from the group consisting of H, alkyl, halogen and alkoxy.

13. A compound of claim 11 or a salt thereof wherein said $R_5$, $R_6$, $R_7$, $R_8$, $R_9$ and $R_{10}$ of said structure (a) are each independently selected from the group consisting of H, methyl, methoxy and fluorine.

14. A compound of claim 2 or a salt thereof wherein B is 2,2'-dimethyl-1,1'-biphenyl4-yl or 2-methoxy-2'-methyl-1, 1'-biphenyl-4-yl; and X is FG wherein F is —CH$_2$— or —(CH$_2$)$_2$—, and G is

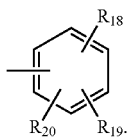

15. A compound of claim 14 or a salt thereof wherein each of said $R_{18}$, $R_{19}$ and $R_{20}$ of said G is independently selected from the group consisting of hydrogen, —CH$_3$, —CF$_3$, —OCH$_3$, F and OH; or when $R_{18}$ is hydrogen and $R_{19}$ and $R_{20}$ are on adjacent carbon atoms, then $R_{19}$ and $R_{20}$ can together form —O(—CH$_2$)$_m$—O— wherein m is 1 or 2.

16. A compound of claim 14 or a salt thereof wherein G is selected from the group consisting of 4-methylphenyl-1-yl, 2-trifluoromethylphenyl-1-yl, phenyl, 4-hydroxyphenyl-1-yl, 4-fluorophenyl-1-yl, 3-methoxyphenyl-1-yl and

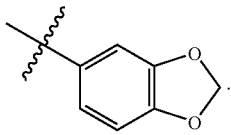

17. A compound of claim 1 or a salt thereof wherein B has the structure of (a) or (b).

18. A compound of claim 1 or a salt thereof wherein B has the structure of (c).

19. A compound of claim 1 that is:
   a) 10-[(2,2'-Dimethyl-1,1'-biphenyl-4-yl)carbonyl]-N-(3-methoxybenzyl)-10,11-dihydro-5H-pyrrolo[2,1-c][1,4]benzodiazepine-3-carboxamide;
   b) 10-[(2,2'-Dimethyl-1,1'-biphenyl-4-yl)carbonyl]-N-(4-methylbenzyl)-10,11-dihydro-5H-pyrrolo[2,1-c][1,4]benzodiazepine-3-carboxamide;
   c) N-(1,3-Benzodioxol-5-ylmethyl)-10-[(2,2'-dimethyl-1,1'-biphenyl-4-yl)carbonyl]-10,11-dihydro-5H-pyrrolo[2,1-c][1,4]benzodiazepine-3-carboxamide;
   d) 10-[(2,2'-Dimethyl-1,1'-biphenyl-4-yl)carbonyl]-N-[2-(4-hydroxyphenyl)ethyl]-10,11-dihydro-5H-pyrrolo[2,1-c][1,4]benzodiazepine-3-carboxamide;
   e) 10-[(2-Methoxy-2'-methyl-1,1'-biphenyl-4-yl)carbonyl]-N-(4-methylbenzyl)-10,11-dihydro-5H-pyrrolo[2,1-c][1,4]benzodiazepine-3-carboxamide;
   f) N-(1,3-Benzodioxol-5-ylmethyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;
   g) N-Benzyl-10-[(2-methoxy-2'-methyl-1,1'-biphenyl-4-yl)carbonyl]-10,11-dihydro-5H-pyrrolo[2,1-c][1,4]benzodiazepine-3-carboxamide; or
   h) N-(4-Fluorobenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide; or a pharmaceutically acceptable salt thereof.

20. A compound of claim 1 that is:
   b) N-[2-(Dimethylamino)-2-phenylethyl]-10-[(2'-methoxy-1,1'-biphenyl-4-yl)carbonyl]-10,11-dihydro-5H-pyrrolo[2,1-c][1,4]benzodiazepine-3-carboxamide;
   c) N-(2-Chloro-6-phenoxybenzyl)-10-[(2'-methoxy-1,1'-biphenyl-4-yl)carbonyl]-10,11-dihydro-5H-pyrrolo[2,1-c][1,4]benzodiazepine-3-carboxamide;
   d) N-[(1R)-2-hydroxy-1-phenylethyl]-10-[(2'-methoxy-1,1'-biphenyl-4-yl)carbonyl]-10,11-dihydro-5H-pyrrolo[2,1-c][1,4]benzodiazepine-3-carboxamide;
   e) N-[(1S)-2-Hydroxy-1-phenylethyl]-10-[(2'-methoxy-1,1'-biphenyl-4-yl)carbonyl]-10,11-dihydro-5H-pyrrolo[2,1-c][1,4]benzodiazepine-3-carboxamide;
   g) 10-[(2,2'-Dimethyl-1,1'-biphenyl-4-yl)carbonyl]-N-(4-methoxybenzyl)-10,11-dihydro-5H-pyrrolo[2,1-c][1,4]benzodiazepine-3-carboxamide;
   h) 10-[(2,2'-Dimethyl-1,1'-biphenyl-4-yl)carbonyl]-N-(4-hydroxybenzyl)-10,11-dihydro-5H-pyrrolo[2,1-c][1,4]benzodiazepine-3-carboxamide;
   i) 10-[(2,2'-Dimethyl-1,1'-biphenyl-4-yl)carbonyl]-N-(3-hydroxybenzyl)-10,11-dihydro-5H-pyrrolo[2,1-c][1,4]benzodiazepine-3-carboxamide;
   j) N-[4-(Aminomethyl)benzyl]-10-[(2,2'-dimethyl-1,1'-biphenyl-4-yl)carbonyl]-10,11-dihydro-5H-pyrrolo[2,1-c][1,4]benzodiazepine-3-carboxamide;
   k) N-[3-(Aminomethyl)benzyl]-10-[(2,2'-dimethyl-1,1'-biphenyl-4-yl)carbonyl]-10,11-dihydro-5H-pyrrolo[2,1-c][1,4]benzodiazepine-3-carboxamide;

l) 10-[(2,2'-Dimethyl-1,1'-biphenyl-4-yl)carbonyl]-N-(1-phenylethyl)-10,11-dihydro-5H-pyrrolo[2,1-c][1,4]benzodiazepine-3-carboxamide;

m) N-Benzyl-10-[(2,2'-dimethyl-1,1'-biphenyl-4-yl)carbonyl]-10,11-dihydro-5H-pyrrolo[2,1-c][1,4]benzodiazepine-3-carboxamide;

n) 10-[(2,2'-Dimethyl-1,1'-biphenyl-4-yl)carbonyl]-N-[3-(trifluoromethyl)benzyl]-10,11-dihydro-5H-pyrrolo[2,1-c][1,4]benzodiazepine-3-carboxamide;

o) 10-[(2,2'-Dimethyl-1,1'-biphenyl-4-yl)carbonyl]-N-(2-methylbenzyl)-10,11-dihydro-5H-pyrrolo[2,1-c][1,4]benzodiazepine-3-carboxamide;

p) N-(4-Chlorobenzyl)-10-[(2,2'-dimethyl-1,1'-biphenyl-4-yl)carbonyl]-10,11-dihydro-5H-pyrrolo[2,1-c][1,4]benzodiazepine-3-carboxamide;

q) 10-[(2,2'-Dimethyl-1,1'-biphenyl-4-yl)carbonyl]-N-[4-(trifluoromethoxy)benzyl]-10,11-dihydro-5H-pyrrolo[2,1-c][1,4]benzodiazepine-3-carboxamide;

r) N-(3,5-Dimethoxybenzyl)-10-[(2,2'-dimethyl-1,1'-biphenyl-4-yl)carbonyl]-10,11-dihydro-5H-pyrrolo[2,1-c][1,4]benzodiazepine-3-carboxamide;

s) N-(2,4-Dimethylbenzyl)-10-[(2,2'-dimethyl-1,1'-biphenyl-4-yl)carbonyl]-10,11-dihydro-5H-pyrrolo[2,1-c][1,4]benzodiazepine-3-carboxamide;

t) 10-[(2,2'-Dimethyl-1,1'-biphenyl-4-yl)carbonyl]-N-(3-methylbenzyl)-10,11-dihydro-5H-pyrrolo[2,1-c][1,4]benzodiazepine-3-carboxamide;

u) 10-[(2,2'-Dimethyl-1,1'-biphenyl-4-yl)carbonyl]-N-[2-(trifluoromethyl)benzyl]-10,11-dihydro-5H-pyrrolo[2,1-c][1,4]benzodiazepine-3-carboxamide;

v) 10-[(2,2'-Dimethyl-1,1'-biphenyl-4-yl)carbonyl]-N-(3-phenylpropyl)-10,11-dihydro-5H-pyrrolo[2,1-c][1,4]benzodiazepine-3-carboxamide;

w) N-[2-(3-Chlorophenyl)ethyl]-10-[(2,2'-dimethyl-1,1'-biphenyl-4-yl)carbonyl]-10,11-dihydro-5H-pyrrolo[2,1-c][1,4]benzodiazepine-3-carboxamide;

x) N-[2-(4-Chlorophenyl)ethyl]-10-[(2,2'-dimethyl-1,1'-biphenyl-4-yl)carbonyl]-10,11-dihydro-5H-pyrrolo[2,1-c][1,4]benzodiazepine-3-carboxamide;

y) N-[2-(3,4-Dimethoxyphenyl)ethyl]-10-[(2,2'-dimethyl-1,1'-biphenyl-4-yl)carbonyl]-10,11-dihydro-5H-pyrrolo[2,1-c][1,4]benzodiazepine-3-carboxamide;

z) 10-[(2,2'-Dimethyl-1,1'-biphenyl-4-yl)carbonyl]-N-[2-(4-methylphenyl)ethyl]-10,11-dihydro-5H-pyrrolo[2,1-c][1,4]benzodiazepine-3-carboxamide;

aa) 10-[(2,2'-Dimethyl-1,1'-biphenyl-4-yl)carbonyl]-N-[2-(4-methoxyphenyl)ethyl]-10,11-dihydro-5H-pyrrolo[2,1-c][1,4]benzodiazepine-3-carboxamide;

bb) 10-[(2,2'-Dimethyl-1,1'-biphenyl-4-yl)carbonyl]-N-(1-methyl-3-phenylpropyl)-10,11-dihydro-5H-pyrrolo[2,1-c][1,4]benzodiazepine-3-carboxamide;

cc) N-[2-(1,3-Benzodioxol-5-yl)ethyl]-10-[(2,2'-dimethyl-1,1'-biphenyl-4-yl)carbonyl]-10,11-dihydro-5H-pyrrolo[2,1-c][1,4]benzodiazepine-3-carboxamide;

dd) N-(3-Aminobenzyl)-10-[(2,2'-dimethyl-1,1'-biphenyl-4-yl)carbonyl]-10,11-dihydro-5H-pyrrolo[2,1-c][1,4]benzodiazepine-3-carboxamide;

ff) N-(4-Methoxybenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

gg) 10-[(2-Methoxy-2'-methyl-1,1'-biphenyl-4-yl)carbonyl]-N-(3-methylbenzyl)-10,11-dihydro-5H-pyrrolo[2,1-c][1,4]benzodiazepine-3-carboxamide;

hh) 10-[(2-Methoxy-2'-methyl-1,1'-biphenyl-4-yl)carbonyl]-N-[2-(trifluoromethyl)benzyl]-10,11-dihydro-5H-pyrrolo[2,1-c][1,4]benzodiazepine-3-carboxamide;

ii) 10-[(2-Methoxy-2'-methyl-1,1'-biphenyl-4-yl)carbonyl]-N-(2-methylbenzyl)-10,11-dihydro-5H-pyrrolo[2,1-c][1,4]benzodiazepine-3-carboxamide;

jj) 10-[(2-Methoxy-2'-methyl-1,1'-biphenyl-4-yl)carbonyl]-N-[3-(trifluoromethyl)benzyl]-10,11-dihydro-5H-pyrrolo[2,1-c][1,4]benzodiazepine-3-carboxamide;

kk) N-(4-Chlorobenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

ll) 10-[(2-Methoxy-2'-methyl-1,1'-biphenyl-4-yl)carbonyl]-N-[4-(trifluoromethoxy)benzyl]-10,11-dihydro-5H-pyrrolo[2,1-c][1,4]benzodiazepine-3-carboxamide;

mm) N-(2,4-Dimethylbenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

nn) 10-[(2-Methoxy-2'-methyl-1,1'-biphenyl-4-yl)carbonyl]-N-[2-(4-methoxyphenyl)ethyl]-10,11-dihydro-5H-pyrrolo[2,1-c][1,4]benzodiazepine-3-carboxamide;

oo) 10-[(2-Methoxy-2'-methyl-1,1'-biphenyl-4-yl)carbonyl]-N-[2-(4-methylphenyl)ethyl]-10,11-dihydro-5H-pyrrolo[2,1-c][1,4]benzodiazepine-3-carboxamide;

pp) 10-[(2-Methoxy-2'-methyl-1,1'-biphenyl-4-yl)carbonyl]-N-(4-phenylbutyl)-10,11-dihydro-5H-pyrrolo[2,1-c][1,4]benzodiazepine-3-carboxamide;

qq) N-(2,2-Diphenylethyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

rr) N-[2-(3-Chlorophenyl)ethyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

ss) N-[2-(3,4-Dimethoxyphenyl)ethyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

tt) N-[2-(4-Chlorophenyl)ethyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

uu) 10-[(2-Methoxy-2'-methyl-1,1'-biphenyl-4-yl)carbonyl]-N-(3-phenylpropyl)-10,11-dihydro-5H-pyrrolo[2,1-c][1,4]benzodiazepine-3-carboxamide;

vv) N-[2-(4-Hydroxyphenyl)ethyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

ww) 10-[(2,2'-Dimethyl-1,1'-biphenyl-4-yl)carbonyl]-N-(4-phenylbutyl)-10,11-dihydro-5H-pyrrolo[2,1-c][1,4]benzodiazepine-3-carboxamide;

xx) N-[4-(Dimethylamino)benzyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

yy) 10-[(2-Methoxy-2'-methyl-1,1'-biphenyl-4-yl)carbonyl]-N-(1-phenylethyl)-10,11-dihydro-5H-pyrrolo[2,1-c][1,4]benzodiazepine-3-carboxamide;

zz) N-(3,3-Diphenylpropyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

aaa) N-(2,4-Difluorobenzyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

bbb) N-[2-(1,3-Benzodioxol-5-yl)ethyl]-10-[(2-methoxy-2'-methyl-1,1'-biphenyl-4-yl)carbonyl]-10,11-dihydro-5H-pyrrolo[2,1-c][1,4]benzodiazepine-3-carboxamide;

ccc) N-(2-Hydroxy-2-phenylethyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

ddd) N-(2,3-Dihydro-1,4-benzodioxin-6-ylmethyl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

eee) N-(2,3-Dihydro-1H-inden-2-yl)-10-[(2-methoxy-2'-methyl-1,1'-biphenyl-4-yl)carbonyl]-10,11-dihydro-5H-pyrrolo[2,1-c][1,4]benzodiazepine-3-carboxamide;

fff) N-[2-(4-Hydroxyphenyl)ethyl]-10-[(2'-methoxy-2-methyl-1,1'-biphenyl-4-yl)carbonyl]-10,11-dihydro-5H-pyrrolo[2,1-c][1,4]benzodiazepine-3-carboxamide;

hhh) 10-[(4-Chlorophenoxy)acetyl]-N-[2-(4-hydroxyphenyl)ethyl]-10,11-dihydro-5H-pyrrolo[2,1-c][1,4]benzodiazepine-3-carboxamide;

iii) N-(1,3-Benzodioxol-5-ylmethyl)-10-[(4-chlorophenoxy)acetyl]-10,11-dihydro-5H-pyrrolo[2,1-c][1,4]benzodiazepine-3-carboxamide;

jjj) 10-[(4-Chlorophenoxy)acetyl]-N-(4-methylbenzyl)-10,11-dihydro-5H-pyrrolo[2,1-c][1,4]benzodiazepine-3-carboxamide;

kkk) 10-[(4-Chlorophenoxy)acetyl]-N-(3-methylbenzyl)-10,11-dihydro-5H-pyrrolo[2,1-c][1,4]benzodiazepine-3-carboxamide;

lll) 10-[(4-Chlorophenoxy)acetyl]-N-[3-(trifluoromethyl)benzyl]-10,11-dihydro-5H-pyrrolo[2,1-c][1,4]benzodiazepine-3-carboxamide;

mmm) 10-[(4-Chlorophenoxy)acetyl]-N-(2-hydroxy-2-phenylethyl)-10,11-dihydro-5H-pyrrolo[2,1-c][1,4]benzodiazepine-3-carboxamide;

nnn) N-(1,1'-Biphenyl-4-yl)-10-[(4-chlorophenoxy)acetyl]-10,11-dihydro-5H-pyrrolo[2,1-c][1,4]benzodiazepine-3-carboxamide;

ppp) N(1,3-Benzodioxol-5-ylmethyl)-10-[(4-chloro-2-methylphenoxy)-acetyl]-10,11-dihydro-5H-pyrrolo[2,1-c][1,4]benzodiazepine-3-carboxamide;

qqq) Methyl 4-{[({10-[(4-chloro-2-methylphenoxy)acetyl]-10,11-dihydro-5H-pyrrolo[2,1-c][1,4]benzodiazepin-3-yl}carbonyl)amino]methyl}benzoate;

rrr) 10-[(4-Chloro-2-methylphenoxy)acetyl]-N-(4-hydroxy-3-methoxybenzyl)-10,11-dihydro-5H-pyrrolo[2,1-c][1,4]benzodiazepine-3-carboxamide;

sss) 10-[(4-Chlorophenoxy)acetyl]-N-(2',3-dimethyl-1,1'-biphenyl-4-yl)-10,11-dihydro-5H-pyrrolo[2,1-c][1,4]benzodiazepine-3-carboxamide;

ttt) 2,2,2-Trichloro-1-[10-{[(4-bromophenyl)thio]acetyl}-10,11-dihydro-5H-pyrrolo[2,1-c][1,4]benzodiazepine-3-yl]-ethanone;

uuu) 10-{[(4-Bromophenyl)thio]acetyl)-N-(3,4-dichlorobenzyl)-10,11-dihydro-5H-pyrrolo[2,1-c][1,4]benzodiazepine-3-carboxamide;

vvv) 10-{[(4-Bromophenyl)thio]acetyl}-N-(4-hydroxy-3-methoxybenzyl)-10,11-dihydro-5H-pyrrolo[2,1-c][1,4]benzodiazepine-3-carboxamide;

www) 10-{[(4-Bromophenyl)thio]acetyl}-N-(4-methylbenzyl)-10,11-dihydro-5H-pyrrolo[2,1-c][1,4]benzodiazepine-3-carboxamide;

xxx) N-(1,3-Benzodioxol-5-ylmethyl)-10-{[(4-bromophenyl)thio]acetyl}-10,11-dihydro-5H-pyrrolo[2,1-c][1,4]benzodiazepine-3-carboxamide;

yyy) 10-{[(4-Bromophenyl)thio]acetyl}-N-[3-(trifluoromethyl)benzyl]-10,11-dihydro-5H-pyrrolo[2,1-c][1,4]benzodiazepine-3-carboxamide;

zzz) 10-{[(4-Bromophenyl)thio]acetyl}-N-[2-(4-hydroxyphenyl)ethyl]-10,11-dihydro-5H-pyrrolo[2,1-c][1,4]benzodiazepine-3-carboxamide;

aaaa) 10-{[(4-Bromophenyl)thio]acetyl}-N-(1,2,3,4-tetrahydronaphthalen-1-yl)-10,11-dihydro-5H-pyrrolo[2,1-c][1,4]benzodiazepine-3-carboxamide;

bbbb) N-(4-benzoylbenzyl)-10-[(2,2'-dimethyl-1,1'-biphenyl-4-yl)carbonyl]-10,11-dihydro-5H-pyrrolo[2,1-c][1,4]benzodiazepine-3-carboxamide;

cccc) N-(3,5-dimethoxybenzyl)-10-[(2-methoxy-2'-methyl-1,1'-biphenyl-4-yl)carbonyl]-10,11-dihydro-5h-pyrrolo[2,1-c][1,4]benzodiazepine-3-carboxamide;

dddd) 10-[(2,2'-dimethyl-1,1'-biphenyl-4-yl)carbonyl]-N-(2,2-diphenylethyl)-10,11-dihydro-5H-pyrrolo[2,1-c][1,4]benzodiazepine-3-carboxamide;

eeee) N-[4-(dimethylamino)benzyl]-10-[(2,2'-dimethyl-1,1'-biphenyl-4-yl)carbonyl]-10,11-dihydro-5H-pyrrolo[2,1-c][1,4]benzodiazepine-3-carboxamide;

ffff) N-(2,3-dihydro-1H-inden-1-yl)-10-[(2,2'-dimethyl-1,1'-biphenyl-4-yl)carbonyl]-10,11-dihydro-5H-pyrrolo[2,1-c][1,4]benzodiazepine-3-carboxamide;

gggg) N-(2,3-dihydro-1H-inden-2-yl)-10-[(2,2'-dimethyl-1,1'-biphenyl-4-yl)carbonyl]-10,11-dihydro-5H-pyrrolo[2,1-c][1,4]benzodiazepine-3-carboxamide;

hhhh) 10-[(4-chlorophenoxy)acetyl]-N-(1,2,3,4-tetrahydronaphthalen-1-yl)-10,11-dihydro-5H-pyrrolo[2,1-c][1,4]benzodiazepine-3-carboxamide;

iiii) Methyl 4-[({10-[(4-chlorophenoxy)acetyl]-10,11-dihydro-5H-pyrrolo[2,1-c][1,4]benzodiazepin-3-yl}carbonyl)amino]-2-methoxybenzoate;

jjjj) Ethyl 4-[({10-[(4-chlorophenoxy)acetyl]-10,11-dihydro-5H-pyrrolo[2,1-c][1,4]benzodiazepin-3-yl}carbonyl)amino]benzoate;

kkkk) 10-[(4-chlorophenoxy)acetyl]-N-(9-hydroxy-9H-fluoren-2-yl)-10,11-dihydro-5H-pyrrolo[2,1-c][1,4]benzodiazepine-3-carboxamide;

llll) Dimethyl 5-[({10-[(4-chlorophenoxy)acetyl]-10,11-dihydro-5H-pyrrolo[2,1-c][1,4]benzodiazepin-3-yl}carbonyl)amino]isophthalate;

mmmm) Ethyl 3-[({10-[(4-chlorophenoxy)acetyl]-10,11-dihydro-5H-pyrrolo[2,1-c][1,4]benzodiazepin-3-yl}carbonyl)amino]benzoate;

nnnn) N-(1,1'-biphenyl-3-yl)-10-[(4-chlorophenoxy)acetyl]-10,11-dihydro-5H-pyrrolo[2,1-c][1,4]benzodiazepine-3-carboxamide;

oooo) 10-[(4-chlorophenoxy)acetyl]-N-[3-(dimethylamino)phenyl]-10,11-dihydro-5H-pyrrolo[2,1-c][1,4]benzodiazepine-3-carboxamide pppp) N-(4-tert-butylphenyl)-10-[(4-chlorophenoxy)acetyl]-10,11-dihydro-5H-pyrrolo[2,1-c][1,4]benzodiazepine-3-carboxamide;

qqqq) N-(7-bromo-9-oxo-9H-fluoren-2-yl)-10-[(4-chlorophenoxy)acetyl]-10,11-dihydro-5H-pyrrolo[2,1-c][1,4]benzodiazepine-3-carboxamide; or rrrr) N-[2-(1,3-benzodioxol-5-yl)ethyl]-10-{[(4-bromophenyl)thio]acetyl}-10,11-dihydro-5H-pyrrolo[2,1-c][1,4]benzodiazepine-3-carboxamide; or a pharmaceutically acceptable salt thereof.

21. A composition comprising at least one compound of claim 1 or a pharmaceutically acceptable salt thereof.

22. A composition comprising at least one compound of claim 2 or a pharmaceutically acceptable salt thereof.

23. A composition comprising at least one compound of claim 6 or a pharmaceutically acceptable salt thereof.

24. A composition comprising at least one compound of claim 7 or a pharmaceutically acceptable salt thereof.

25. A composition comprising at least one compound of claim 8 or a pharmaceutically acceptable salt thereof.

26. A composition comprising at least one compound of claim 9 or a pharmaceutically acceptable salt thereof.

27. A composition comprising at least one compound of claim 19 or a pharmaceutically acceptable salt thereof.

28. A composition comprising at least one compound of claim 20 or a pharmaceutically acceptable salt thereof.

29. A method of inhibiting fertility in a mammal, said method comprising administering to said mammal an effective amount of at least one compound of claim 1 or a pharmaceutically acceptable salt thereof.

30. A method of inhibiting fertility in a mammal, said method comprising administering an effective amount of at least one compound of claim 2 to said mammal.

31. A method of inhibiting fertility in a mammal, said method comprising administering an effective amount of at least one compound of claim 6 to said mammal.

32. A method of inhibiting fertility in a mammal, said method comprising administering an effective amount of at least one compound of claim 7 to said mammal.

33. A method of inhibiting fertility in a mammal, said method comprising administering an effective amount of at least one compound of claim 8 to said mammal.

34. A method of inhibiting fertility in a mammal, said method comprising administering an effective amount of at least one compound of claim 9 to said mammal.

35. A method of inhibiting fertility in a mammal, said method comprising administering an effective amount of at least one compound of claim 19 to said mammal.

36. A method of inhibiting fertility in a mammal, said method comprising administering an effective amount of at least one compound of claim 20 to said mammal.

37. A method of preventing conception in a mammal, said method comprising administering an effective amount of at least one compound of claim 1 to said mammal.

38. A method of preventing conception in a mammal, said method comprising administering an effective amount of at least one compound of claim 2 to said mammal.

39. A method of preventing conception in a mammal, said method comprising administering an effective amount of at least one compound of claim 6 to said mammal.

40. A method of preventing conception in a mammal, said method comprising administering an effective amount of at least one compound of claim 7 to said mammal.

41. A method of preventing conception in a mammal, said method comprising administering an effective amount of at least one compound of claim 8 to said mammal.

42. A method of preventing conception in a mammal, said method comprising administering an effective amount of at least one compound of claim 9 to said mammal.

43. A method of preventing conception in a mammal, said method comprising administering an effective amount of at least one compound of claim 19 to said mammal.

44. A method of preventing conception in a mammal, said method comprising administering an effective amount of at least one compound of claim 20 to said mammal.

* * * * *